(12) United States Patent
Hanabata et al.

(10) Patent No.: US 7,534,547 B2
(45) Date of Patent: May 19, 2009

(54) OPTICALLY ACTIVE COMPOUND AND PHOTOSENSITIVE RESIN COMPOSITION

(75) Inventors: Makoto Hanabata, Kyoto (JP);
Masahiro Sato, Kyoto (JP); Junko Katayama, Kyoto (JP); Satsuki Kitajima, Kyoto (JP); Atsushi Niwa, Kyoto (JP)

(73) Assignee: Osaka Gas Company Limited, Osaka (JP)

( * ) Notice: Subject to any disclaimer, the term of this patent is extended or adjusted under 35 U.S.C. 154(b) by 1015 days.

(21) Appl. No.: 10/296,831

(22) PCT Filed: Mar. 29, 2002

(86) PCT No.: PCT/JP02/03140

§ 371 (c)(1),
(2), (4) Date: Nov. 27, 2002

(87) PCT Pub. No.: WO02/079131

PCT Pub. Date: Oct. 10, 2002

(65) Prior Publication Data

US 2003/0211421 A1  Nov. 13, 2003

(30) Foreign Application Priority Data

Mar. 29, 2001 (JP) ............................. 2001-97019
Mar. 29, 2001 (JP) ............................. 2001-97020

(51) Int. Cl.
*G03F 7/00* (2006.01)
*G03F 7/004* (2006.01)

(52) U.S. Cl. .................... 430/270.1; 430/325; 430/330; 430/913

(58) Field of Classification Search .............. 430/270.1, 430/325
See application file for complete search history.

(56) References Cited

U.S. PATENT DOCUMENTS 4,529,556 A * 7/1985 Bruza ......................... 558/423

(Continued)

FOREIGN PATENT DOCUMENTS

EP   249 139   12/1987

(Continued)

OTHER PUBLICATIONS

CAplus Abstract DN 117:80291 of JP 4089451, Mar. 1992.*

(Continued)

*Primary Examiner*—Amanda C. Walke
(74) *Attorney, Agent, or Firm*—Pillsbury Winthrop Shaw Pittman LLP

(57) ABSTRACT

A photoactive compound is used in combination with a photosensitizer, represented by the following formula (1):

$$A-[(J)_m-(X-Pro)]_n \qquad (1)$$

wherein A represents a hydrophobic unit comprising at least one kind of hydrophobic groups selected from a hydrocarbon group and a heterocyclic group, J represents a connecting group, X-Pro represents a hydrophilic group protected by a protective group Pro which is removable by light exposure, m represents 0 or 1, and n represents an integer of not less than 1.

The protective group Pro may be removable by light exposure in association with the photosensitizer (especially, a photo acid generator), or may be a hydrophobic protective group. The hydrophilic group may be a hydroxyl group or a carboxyl group. The photoactive compound has high sensitivity to a light source of short wavelength beams, for resist application, therefore, the photoactive compound is advantageously used for forming a pattern with high resolution.

22 Claims, 2 Drawing Sheets

U.S. PATENT DOCUMENTS

| | | | |
|---|---|---|---|
| 5,426,016 A | | 6/1995 | Fujioka et al. |
| 6,030,746 A | * | 2/2000 | Nagata et al. ............ 430/270.1 |
| 6,174,631 B1 | * | 1/2001 | French et al. .................. 430/5 |

FOREIGN PATENT DOCUMENTS

| | | | | |
|---|---|---|---|---|
| EP | 541 112 | | | 5/1993 |
| JP | 1311051 | A | | 12/1989 |
| JP | 3-289659 | | | 12/1991 |
| JP | 040509 47 | | * | 2/1992 |
| JP | 4089451 | | * | 3/1992 |
| JP | 4-158363 | | | 6/1992 |
| JP | 5-232704 | | | 9/1993 |
| JP | 06-073041 | | * | 3/1994 |
| JP | 6-167811 | | | 6/1994 |
| JP | 6301210 | A | | 10/1994 |
| JP | 710892 | A | | 4/1995 |
| JP | 2001312055 | A | | 11/2001 |

OTHER PUBLICATIONS

CA abstract DN 118:113113 for JP 04050947.*

Encapsulated Inorganic Resist Technology, Theodore H. Fedynyshyn et al. Processing XVII, Francis M. Houlihan, Editor, Proceedings of SPIE, vol. 3999(2000) pp. 627-637.

* cited by examiner

OPTICALLY ACTIVE COMPOUND AND PHOTOSENSITIVE RESIN COMPOSITION

CROSS REFERENCE TO RELATED APPLICATIONS

This is the U.S. National Phase of PCT/JP2002/03140, filed Mar. 29, 2002, which designates the U.S. which in turn claims priority to Japanese application Nos. 2001-97019 and 2001-97020, both filed on Mar. 29, 2001, the entire contents of all which are incorporated herein in their entirety by reference.

This application is the National Phase of International Application PCT/JP02/03140 filed Mar. 29, 2002 which designated the U.S. and that International Application was not published under PCT Article 21(2) in English.

TECHNICAL FIELD

The present invention relates to a photoactive compound used in combination with a photosensitizer, which is useful for forming minute patterns such as semiconductor integrated circuits using a beam, for example, ultraviolet rays or far-ultraviolet rays (including excimer lasers or the like), a photosensitive resin composition (resist composition) composed of the compound, and a process for forming a pattern using the composition.

BACKGROUND ART

In the field of semiconductor resists, with developing very large scale integrated circuits, higher minute processing techniques have been demanded. Thereupon, light sources of shorter wavelength beams such as KrF excimer laser (wavelength: 248 nm), ArF excimer laser (wavelength: 193 nm) and $F_2$ excimer laser (wavelength: 157 nm) are utilized instead of g-ray (wavelength: 436 nm) or i-ray (wavelength: 365 nm) of a conventional high-pressure mercury lamp.

Moreover, with rises in the integration level of semiconductor integrated circuits, there has been also demanded for resists with better resolution (formation of patterns in submicron order, quartermicron order or smaller) and for improvement of etching resistance in the process of dry development.

However, even when KrF excimer laser or ArF excimer laser is applied to a conventional resist material (such as a novolak resin/diazonaphthoquinone-based positive resist) in which g-ray or i-ray is employed, sensitivity and resolution of the conventional resist materials are considerably deteriorated owing to light absorption by the novolak resin.

Sondi and Matijevic disclose a film composed of a p-hydroxystyrene-t-butyl acrylate copolymer containing $SiO_2$ nanoparticles (silicasol) as a resist having applicability to an exposure light source of shorter wavelength beams (I. Sondi and E. Matijevic, Resist Technology and Processing XVII, Francis M. Houlihan, Editor, Proceedings of SPIE Vol. 3999 (2000), pp. 627-637), and this literature describes a resist including such a $SiO_2$ nanoparticle shows high resolution, and a resist system using a transparent $SiO_2$ nanoparticle is useful to wavelengths such as 157 nm. However, since difference in dissolution rate between exposed area and non-exposed area cannot be enlarged by this method, resolution of a resist cannot be sufficiently improved.

Accordingly, it is an object of the present invention to provide a photoactive compound that is helpful for improving sensitivity and resolution of a resist, concerning the combination with a photosensitizer; a photosensitive resin composition using the photoactive compound; and a process for forming a pattern using the photosensitive resin composition.

It is another object of the present invention to provide a photoactive compound which has high sensitivity even to short wavelength beams emitted from an exposure light source and which is useful for forming a minute pattern with high resolution, a photosensitive resin composition using the photoactive compound, and a process for forming a pattern using the photosensitive resin composition.

It is still another object of the present invention to provide a photoactive compound which is useful for enlarging difference in dissolution rate between exposed area and non-exposed area to a developer, a photosensitive resin composition using the photoactive compound, and a process for forming a pattern using the photosensitive resin composition.

DISCLOSURE OF INVENTION

The inventors of the present invention made intensive and extensive studies to achieve the above-mentioned objects and finally found that the combination use of a photosensitizer and a photoactive compound which is capable of hydrophilicity by deprotection owing to (or through) light exposure can simply improve sensitivity and resolution of a resist, even when a light source of short wavelength beams such as KrF excimer laser is used.

That is, a photoactive compound is usable in combination with a photosensitizer, represented by the following formula (1):

$$A\text{-}[(J)_m\text{-}(X\text{-}Pro)]_n \qquad (1)$$

wherein A represents a hydrophobic unit comprising at least one hydrophobic group selected from a hydrocarbon group and a heterocyclic group, J represents a connecting group, X-Pro represents a hydrophilic group protected by a protective group Pro which is removable (capable of removing or deprotecting) by (owing to) light exposure, m represents 0 or 1, and n represents an integer of not less than 1.

The protective group Pro may be removable (eliminable) by light exposure in association with the photosensitizer. Moreover, the protective group Pro may be a hydrophobic protective group, and the photoactive compound may be formable (capable of forming) a hydroxyl group or a carboxyl group by deprotection of the hydrophobic protective group. The protective group Pro may be (i) a protective group for a hydroxyl group, selected from the group consisting of an alkoxyalkyl group, an acyl group, an alkoxycarbonyl group, an oxacycloalkyl group, a crosslinked cyclic alicyclic group, and an alkylsilyl group; or (ii) a protective group for a carboxyl group, selected from the group consisting of an alkyl group, a crosslinked cyclic alicyclic hydrocarbon group, an oxacycloalkyl group, a lactone ring group, and a carbamoyl or N-substituted carbamoyl group. The hydrophobic unit A in the formula (1), may comprise an aliphatic hydrocarbon group, an alicyclic hydrocarbon group, or an aromatic hydrocarbon group.

The connecting group J may, for example, be an alkylene group, an alkenylene group, an alkynylene group, a cycloalkylene group, an arylene group, an oxyalkylene group, an alkyleneoxy group, a poly(oxyalkylene) group, an ether group, a thioether group, a carbonyl group, a carbonyloxy group, an oxycarbonyl group, an amide group, a urethane group, a urea group, or the like. Incidentally, n is about 1 to 10.

The photoactive compound includes a variety of compounds, for example, includes a compound represented by the following formula (3b):

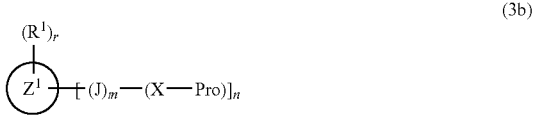

(3b)

wherein $Z^1$ represents, the same or different, a hydrocarbon ring or a heterocycle; $R^1$ represents, the same or different, a halogen atom, an alkyl group, an alkoxy group, an alkoxycarbonyl group, a cycloalkyl group, an aryl group, an aralkyl group, or a silicon-containing group; r represents an integer of 0 or not less than 1; and J, m, X, Pro and n have the same meanings defined above.

The $Z^1$ may, for example, be a $C_{4-40}$ alicyclic hydrocarbon ring or a $C_{6-40}$ aromatic hydrocarbon ring; $R^1$ may represent, the same or different, a halogen atom, an alkyl group, an alkoxy group, a cycloalkyl group, or a silicon-containing group; r may, for example, be about 0 to 4; J may be an alkylene group, an alkenylene group, or an alkynylene group; m is 0 or 1; and n is about 1 to 6.

The photoactive compound includes a compound represented by the following formula (4b):

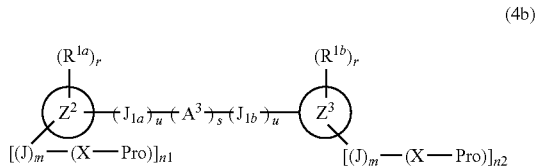

(4b)

wherein $Z^2$ and $Z^3$ are the same or different, each representing a hydrocarbon ring or a heterocycle; $A^3$ represents a connecting group selected from the group consisting of an alkylene group, an alkenylene group, an alkynylene group, a cycloalkylene group, an arylene group, an oxyalkylene group, an alkyleneoxy group, an ether group, a thioether group, a carbonyl group, a carbonyloxy group, a oxycarbonyl group, an amide group, a urethane group, a urea group and a sulfonyl group; s and u are 0 or 1; $J_{1a}$ and $J_{1b}$ are the same or different, each representing a connecting group different from $A^3$ $R^{1a}$ and $R^{1b}$ are the same or different, each representing a halogen atom, an alkyl group, an alkoxy group, an alkoxycarbonyl group, a cycloalkyl group, an aryl group, an aralkyl group or a silicon-containing group; each of the factors (elements), n1 and n2, independently represents 0 or an integer of not less than 1, and n1+n2≧1; and J, r, m, X and Pro have the same meanings defined above.

In the above-mentioned compound, in the case where the connecting group $A^3$ is direct bonding, an alkylene group, an alkenylene group, an alkynylene group, an oxyalkylene group, an alkyleneoxy group, an ether group, a thioether group, a carbonyl group, a carbonyloxy group, an oxycarbonyl group, an amide group, a urethane group, a urea group or a sulfonyl group, u may be 0; or in the case where the connecting group $A^3$ is a cycloalkylene group or an arylene group, u may be 1. Moreover, in the case where the connecting group $A^3$ is a cycloalkylene group or an arylene group, each of the connecting groups, $J_{1a}$ and $J_{1b}$, may be direct bonding or an alkylene group. Further, in the case where the connecting group $A^3$ is a cycloalkylene group or an arylene group, each of the connecting groups, $J_{1a}$ and $J_{1b}$, may be an alkylene group which may have a substituent selected from the group consisting of a halogen atom, an alkyl group, a cycloalkyl group, and an aryl group. In the formula, the hydrophobic unit represented by $Z^2$-$(J_{1a})_u$-$(A^3)_s$-$(J_{1b})_u$-$Z^3$ may be a hydrophobic unit corresponding to the compound selected from the group consisting of (a) a biphenol; (b) a bis(hydroxyaryl)$C_{1-10}$alkane; (c) a bis(hydroxyaryl)cycloalkane; (d) a bisphenol in which $A^3$ is a carbonyl group, an oxygen atom, an ester group, an alkyleneoxy group, an oxyalkylene group, an amide group or a sulfonyl group; (e) a bisphenol in which $A^3$ is a benzene ring, and $J_{1a}$ and $J_{1b}$ are an alkylene group; and (h) a bisphenol having a fluorene-core; and the summation of n1 and n2 may be 1 to 10.

The present invention includes a photosensitive resin composition which comprises a base resin, a photosensitizer and the photoactive compound. The photosensitive resin composition may be developable with water or an alkaline developer and may be a positive photosensitive resin composition. The base resin may comprise a resin which is formable a hydrophilic group by an action of an acid, and the photosensitizer comprises a photo acid generator (photoactive acid generator). The base resin may comprise a homo- or copolymer of a monomer having a hydrophilic group; and the hydrophilic group is, for example, selected from a hydroxyl group and a carboxyl group, and is protectable by a protective group removable by an action of an acid. In the composition, the weight ratio of the photoactive compound relative to the photosensitizer can be selected within the range of about 0.01/1 to 100/1. Moreover, relative to 100 parts by weight of a base resin, the amount of the photosensitizer may be 0.1 to 50 parts by weight and the amount of the photoactive compound may be 1 to 1000 parts by weight. Furthermore, the present invention includes a process for forming a pattern, which comprises applying or coating a photosensitive resin composition recited in claim 15 onto a substrate, exposing the coating layer to light, heat-treating the light-exposed layer, and developing the heat-treated layer to form a pattern.

BEST MODE FOR CARRYING OUT OF THE INVENTION

[Photoactive Compound]

Figure 1:
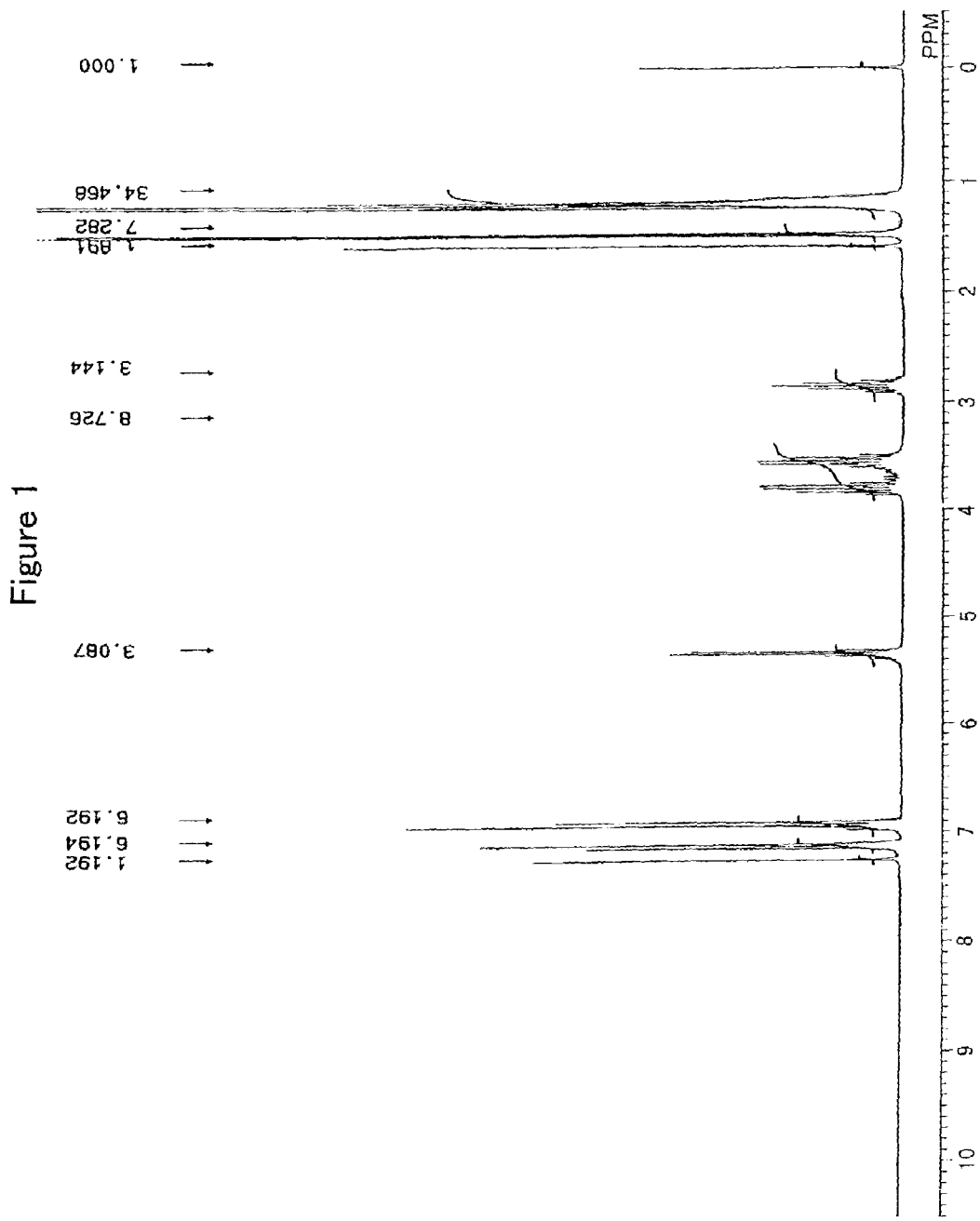
FIG. 1 shows $^1$H-NMR spectrum of 1-(1-ethoxy)ethoxy-4-isopropylbenzene obtained in Example 1.

The photoactive compound of the present invention is used in combination with a photosensitizer and represented by the following formula (1):

(1)

wherein A represents a hydrophobic unit comprising at least one kind of hydrophobic groups selected from a hydrocarbon group and a heterocyclic group, J represents a connecting group, X-Pro represents a hydrophilic group protected by a protective group Pro which is removable (capable of removing) by (owing to) light exposure, m represents 0 or 1, and n represents an integer of not less than 1 (e.g., about 1 to 10, preferably about 1 to 8).

As long as having the unit (1), the photoactive compound may be a homo- or copolymer, or a polymer (e.g., a dimer, a trimer or an oligomer), and the polymer may be represented, for example, by the following formula (2):

(2)

wherein, $A^1$, which as the same meaning as A, represents a hydrophobic unit comprising at least one kind of hydrophobic groups selected from a hydrocarbon group and a heterocyclic group; $A^2$ is a copolymerizable unit, in the same manner as the A, represents a hydrophobic unit comprising at least one kind of hydrophobic groups selected from a hydrocarbon group and a heterocyclic group; $A^1$ and $A^2$ may be the same or different; p is an integer of not less than 1; q is an integer of not less than 0; p/q=30/70 to 100/0; and J, X, Pro, m and n have the same meanings defined above.

In the formula (2), p is about 1 to 100, preferably about 1 to 50, and more preferably about 1 to 20. p/q is preferably about 50/50 to 100/0, and more preferably about 70/30 to 100/0. Moreover, p+q is about 2 to 100, preferably about 2 to 50, and more preferably about 2 to 20.

The preferable hydrophobic unit is a monomer represented by the formula (1), and a dimer (in the case of p=2 and q=0), trimer or oligomer represented by the formula (2).

The hydrocarbon group represented by the hydrophobic units A, $A^1$ and $A^2$ in the formulae (1) and (2) includes an aliphatic hydrocarbon group, an alicyclic hydrocarbon group, an aromatic hydrocarbon group, and the like. As an aliphatic hydrocarbon corresponding to the aliphatic hydrocarbon group (monovalent, bivalent or polyvalent group), there may be mentioned an alkane (for example, a $C_{1-30}$alkane such as butane and hexane (e.g., a $C_{1-10}$alkane), preferably a $C_{2-20}$alkane (e.g., a $C_{2-6}$alkane)], an alkene (for example, a $C_{2-30}$alkene such as ethene (e.g., a $C_{2-6}$alkene)], an alkyne (for example, a $C_{2-30}$alkyne such as ethyne (e.g., a $C_{2-6}$alkyne)].

The hydrophobic unit usually comprises at least one kind of hydrocarbon-ring groups (or hydrophobic groups) selected from an alicyclic hydrocarbon group and an aromatic hydrocarbon group. The alicyclic hydrocarbon group and the aromatic hydrocarbon group may be a monocyclic hydrocarbon group or a condensed cyclic hydrocarbon group. As an alicyclic hydrocarbon corresponding to the alicyclic hydrocarbon group, there may be mentioned a $C_{4-40}$alicyclic hydrocarbon, for example, a monocyclic hydrocarbon [e.g., a $C_{4-16}$cycloalkane such as cyclopentane, cyclohexane and cyclooctane (e.g., a $C_{5\text{-}hd\ 10}$cycloalkane, preferably a $C_{5-8}$cycloalkane), and a $C_{5-16}$cycloalkene such as cyclohexene (e.g., a $C_{5-10}$cycloalkene, preferably a $C_{5-8}$cycloalkene)]; and a crosslinked cyclic hydrocarbon [e.g., a bi- or tricycloalkane (a $C_{6-40}$bi- or tricycloalkane such as norbornane, adamantane and dekalin, for example, a $C_{6-16}$bi- or tricycloalkane), and a bi- or tricycloalkene (a $C_{6-40}$bi- or tricycloalkene such as norbornene, for example, a $C_{6-16}$bi- or tricycloalkene)]. As an aromatic hydrocarbon corresponding to the aromatic hydrocarbon group, there may be exemplified a $C_{6-40}$aromatic hydrocarbon such as benzene, naphthalene, anthracene, phenanthrene, pyrene and terphenylene (in particular, a $C_{6-16}$aromatic hydrocarbon such as benzene and naphthalene); an aromatic hydrocarbon (e.g., a $C_{12-40}$aromatic hydrocarbon) corresponding to a bisphenol (bisphenol, bisphenol A, AD, E, F, M, P, S, Z, etc.) and a polykisphenol; and an aromatic hydrocarbon (e.g., a $C_{12-40}$aromatic hydrocarbon) corresponding to a phenol having fluorene-core. As for the bisphenols and polykisphenols, for example, there may be referred "Methylol Compounds", "Formyl Compounds", "Symmetric Bisphenols", "Asymmetric Bisphenols", "Symmetric Bis (polyhydroxy benzene) Compounds (A)", "Symmetric Bis (polyhydroxy benzene) Compounds (B)", "Trisphenol Methane Compounds (A)", "Trisphenol Methane Compounds (B)", "Linear Trisphenols", "Linear Tetrakisphenols", "Radial Tetrakisphenols", "Linear Pentakisphenols", "Linear Hexakisphenols", "Radial Hexakisphenols", "Branched Hexakisphenols", "Trisphenols from Trimethylol phenol", "Asymmetric Radial Tetrakisphenols" described in "Catalog Handbook of Phenolic Derivatives (first edition)" published by Asahi Organic Chemicals Industry Co., Ltd. on Jan. 17, 2000, and "Bisphenols (seventh edition)" and "Polykisphenols (fifth edition)" published by Honshu Chemical Industry Co., Ltd. Moreover, as for the phenol having the fluorene-core, for example, "Bisphenols (seventh edition)" published by Honshu Chemical Industry Co., Ltd. and the like may be referred. Incidentally, the alicyclic hydrocarbon also includes a hydrocarbon in which the aromatic hydrocarbon is partially or wholly hydrogenated.

As a heterocycle corresponding to the heterocyclic group represented by the hydrophobic units A, $A^1$ and $A^2$, there may be mentioned a heterocycle containing at least one hetero atom selected from oxygen atom, nitrogen atom and sulfur atom (in particular, five- or six-membered heterocycle), for example, a five- or six-membered saturated or unsaturated oxygen-containing ring such as oxacyclohexane ring and pyran ring; and a five- or six-membered saturated or unsaturated nitrogen-containing ring such as pyrrole ring and pyridine ring; a five- or six-membered saturated or unsaturated sulfur-containing ring such as thiacyclohexane ring and thiapyrane ring. The heterocycle may be a condensed heterocycle of a five- or six-membered heterocycle and a hydrocarbon ring (e.g., benzene ring).

The hydrophobic unit need only comprise at least one hydrophobic group above mentioned, and may comprise the above-mentioned hydrophobic group alone, or may comprise a plurality of the hydrophobic groups bonded or connected to each other directly or through a connecting group.

The hydrophobic unit may have a substituent. The substituent includes a halogen atom (fluorine, chlorine, bromine and iodine atoms), an alkyl group [e.g., a $C_{1-18}$alkyl group such as methyl, ethyl, propyl, isopropyl, butyl, s-butyl, t-butyl, hexyl, octyl, decyl, and lauryl groups (preferably a $C_{1-10}$alkyl group, especially a $C_{1-6}$alkyl group)], a cycloalkyl group [e.g., a $C_{4-10}$alkyl group such as cyclopentyl, cyclohexyl and cycloheptyl groups (preferably a $C_{5-8}$alkyl group)], a hydroxyl group, a hydroxyalkyl group [e.g., a hydroxy$C_{1-6}$alkyl group such as hydroxymethyl group, hydroxyethyl group, 2-hydroxypropyl group and hydroxybutyl group], an alkoxy group [e.g., a $C_{1-18}$alkoxy group such as methoxy, ethoxy, propoxy, isopropoxy, butoxy, t-butoxy, hexyloxy, and octyloxy groups (preferably a $C_{1-10}$alkoxy group, especially a $C_{1-6}$alkoxy group], a carboxyl group, an alkoxycarbonyl group [e.g., a $C_{1-18}$alkoxy-carbonyl group such as methoxycarbonyl, ethoxycarbonyl, propoxycarbonyl, butoxycarbonyl, t-butoxycarbonyl, hexyloxycarbonyl and octyloxycarbonyl groups (preferably a $C_{1-10}$alkoxy-carbonyl group, especially a $C_{1-6}$alkoxy-carbonyl group)], a cycloalkyl group [e.g., a $C_{5-12}$cycloalkyl group such as cyclohexyl and cyclooctyl groups (preferably a $C_{5-10}$cycloalkyl group, especially a $C_{5-8}$cycloalkyl group)], an aryl group [e.g., a $C_{6-14}$aryl group such as phenyl and naphthyl groups (preferably a $C_{6-10}$aryl group)], an aralkyl group [e.g., a $C_{6-14}$aryl-$C_{1-6}$alkyl group such as benzyl and phenethyl groups (preferably a $C_{6-10}$aryl-$C_{1-4}$alkyl group)], an acyl group [e.g., a $C_{1-6}$alkylcarbonyl group such as formyl group, acetyl group, propionyl group and butyryl group, a $C_{6-10}$aryl-carbonyl group such as benzoyl group and toluoyl group], a siliconecontaining group such as an alkylsilyl group [e.g., a $C_{1-18}$alkylsilyl group such as methylsilyl, dimethylsilyl, trimethylsilyl, ethylsilyl, diethylsilyl, triethylsilyl, propylsilyl, butylsilyl, t-butylsilyl, and hexylsilyl groups (preferably a $C_{1-10}$alkylsilyl group, more preferably, a tri$C_{1-6}$alkylsilyl group, especially, a tri$C_{1-4}$alkylsilyl group), a $C_{1-18}$alkylsilyl$C_{1-4}$alkyl group (e.g., a tri$C_{1-6}$alkylsilyl$C_{1-4}$alkyl group), a $C_{1-18}$alkylsilyl$C_{2-4}$alkenyl group (e.g., a tri$C_{1-6}$alkylsilyl$C_{2-4}$alkenyl group), a $C_{1-8}$alkylsilyl$C_{2-4}$alkynyl group (e.g., a $C_{1-6}$alkylsilyl$C_{2-4}$alkynyl group)], a nitro group, a cyano group and the like. The substituent may be an alkylamino group, and as the alkylamino group, there may be exemplified an N-alkylamino group whose alkyl site(s) is(are) corresponding to the alkyl group (e.g., an N—$C_{1-18}$alkylamino group, preferably an N—$C_{1-10}$alkylamino group, and especially an N—$C_{1-6}$alkylamino group), and an N,N-dialkylamino group (e.g., an N,N—$C_{1-18}$alkylamino group, preferably an N,N—$C_{1-10}$alkylamino group, and especially an N,N—$C_{1-6}$alkylamino group).

The hydrophobic unit may bond or connect to the hydrophilic group (residue of a hydrophilic group) X through the connecting group J. In the formulae (1) and (2), the connecting group J may be, for example, an alkylene group [e.g., a linear- or branched alkylene group such as methylene, ethylene, dimethylmethylene, di(trifluoromethyl)methylene, propylene, trimethylene, tetramethylene, and t-butylene (e.g., a $C_{1-6}$alkylene group)], an alkenylene group [e.g., a $C_{2-4}$alkenylene group such as vinylene, isopropenylene and propenylene], an alkynylene group [e.g., a $C_{2-4}$alkynylene group such as ethynylene group], a cycloalkylene group [e.g., a $C_{4-8}$cycloalkylene group such as cyclohexylene group], or an arylene group [e.g., a $C_{6-10}$arylene group such as phenylene]. Further, the connecting group J may be an oxyalkylene group, an alkyleneoxy group, a poly(oxyalkylene) group, an ether group, a thioether group, a carbonyl group, an ester group (carbonyloxy group (—C(=O)O—), oxycarbonyl group (—OC(=O)—)), an amide group, a urethane group, a urea group and the like.

The connecting group J is usually an alkylene group [a linear- or branched alkylene group (e.g., a $C_{1-6}$alkylene group)], an alkenylene group [e.g., a $C_{2-4}$alkenylene group such as vinylene], an alkynylene group [e.g., a $C_{2-4}$alkynylene group such as ethynylene group], a cycloalkylene group [e.g., a $C_{4-8}$cycloalkylene group such as cyclohexylene group], an arylene group [e.g., a $C_{6-10}$arylene group such as phenylene], and the like.

Further, as a hydrophilic group corresponding to the group X protected by the protective group Pro (hereinafter, the group X may be simply referred as the hydrophilic group in some cases), there may be exemplified a water- or alkali-soluble group such as a hydroxyl group, a carboxyl group and an sulfur-containing derivative group corresponding to these hydrophilic groups (e.g., mercapto group, thiocarboxyl group and dithiocarboxyl group) in addition to an amino group and an N-substituted amino group (e.g., an N,N-di$C_{1-4}$alkylamino group). In particular, a hydroxyl group (e.g., phenolic hydroxyl group) and carboxyl group are preferable.

As the protective group for a hydroxyl group, there may be mentioned, for example, a $C_{1-12}$alkyl group which may have a substituent, such as methyl, ethyl, propyl, isobutyl, t-butyl, 2-cyclohexyl-2-propyl and hexyl groups (preferably a $C_{1-10}$alkyl group, more preferably a $C_{1-6}$alkyl group); a halo$C_{1-4}$alkyl group such as chloromethyl group, fluoromethyl group, trichloromethyl group, trifluorometyl group and pentafluoropropyl group (preferably a halo$C_{1-4}$alkyl group, more preferably a fluoro$C_{1-4}$alkyl group); a $C_{5-8}$cycloalkyl group which may have a substituent, such as cyclohexyl group and 1-methylcyclohexyl group (e.g., a $C_{5-6}$cycloalkyl group); a bicyclic to tetracyclic $C_{3-30}$hydrocarbon ring group (a crosslinked cyclic alicyclic hydrocarbon group (e.g., a bi- to tetracycloalkyl group) which may have a substituent, for example, a decalinyl or hydrogenated naphthyl group which may have a substituent (e.g., 1-decalinyl group, 2-decalinyl group, and 2-methyl-2-decalinyl group), an adamantyl group which may have a substituent (e.g., 1-adamantyl group, 2-adamantyl group, 1-methyl-2-adamantyl group, and 2-methyl-2-adamantyl group), an norbornyl group which may have a substituent (e.g., 1-norbornyl group, 2-norbornyl group and 2-methyl-2-norbornyl group), a bornyl group which may have a substituent (e.g., 2-bornyl group); a condensed polycyclic hydrocarbon group such as a naphthyl group (e.g., 2-naphthyl group) and a hydrogenated naphthyl group (e.g., 1,4-dihydro-2-naphthyl group); an aryl group such as 2,4-dinitrophenyl group (e.g., a nitro group-substituted phenyl group); an aralkyl group such as benzyl group, 2,6-dichlorobenzyl group, 2-nitrobenzyl group and triphenylmethyl group (e.g., a mono- to tri$C_{6-10}$aryl-$C_{1-4}$alkyl group which may have a substituent); an oxacycloalkyl group such as a tetrahydrofuranyl group and a tetrahydropyranyl group (e.g., a five- or eight-membered oxacycloalkyl group); an acetal-series protective group such as an alkoxyalkyl group (e.g., a $C_{1-6}$alkoxy-$C_{1-6}$alkyl group such as 1-methoxyethyl group, 1-ethoxyethyl group, 1-ethoxypropyl group and 1-methoxy-isopropyl group, preferably a $C_{1-4}$alkoxy-$C_{1-4}$alkyl group); an acyl group such as an alkylcarbonyl group (e.g., a $C_{1-10}$alkyl-carbonyl group such as formyl, acetyl, propionyl, isopropionyl, butyryl, t-butyryl, valeryl and isovaleryl, preferably a $C_{1-8}$alkyl-carbonyl group, more preferably a $C_{1-6}$alkyl-carbonyl group, especially a $C_{1-4}$alkyl-carbonyl group), a cycloalkylcarbonyl group (e.g., a $C_{5-8}$cycloalkyl-carbonyl group such as cyclohexylcarbonyl group, preferably a $C_{5-6}$cycloalkylcarbonyl group) and an arylcarbonyl group (e.g., a $C_{6-10}$aryl-carbonyl group such as benzoyl group); a $C_{1-6}$alkoxy-carbonyl group such as t-butoxycarbony (t-BOC) group (e.g., a $C_{1-4}$alkoxy-carbonyl group); an aralkyloxycarbonyl group such as benzyloxycarbonyl group (e.g., a $C_{6-10}$aryl-$C_{1-4}$alkyloxy-carbonyl group); and an alkylsilyl group such as trimethylsilyl group (e.g., a $C_{1-6}$alkylsilyl, especially a tri$C_{1-4}$alkylsilyl group).

Moreover, as the protective group for a carboxyl group, there may be mentioned, for example, a $C_{1-12}$alkyl group which may have a substituent, such as methyl, ethyl, 2-cyclohexyl-2-propyl, butyl, t-butyl, and hexyl groups (preferably a $C_{1-10}$alkyl group, more preferably a $C_{1-6}$alkyl group); a $C_{3-8}$cycloalkyl group which may have a substituent, such as cyclohexyl group and 1-methylcyclohexyl group; a bicyclic to tetracyclic $C_{3-30}$hydrocarbon ring group (a crosslinked cyclic alicyclic hydrocarbon group which may have a substituent, such as a decalinyl group which may have a substituent (e.g., 1-decalinyl group, 2-decalinyl group, and 2-methyl-2-decalinyl group), an adamantyl group which may have a substituent (e.g., 1-adamantyl group, 2-adamantyl group, 1-methyl-2-adamantyl group, and 2-methyl-2-adamantyl group), a norbornyl group which may have a substituent (e.g., 1-norbornyl group, 2-norbornyl group and 2-methyl-2-norbornyl group), and a bornyl group which may have a substituent (e.g., 2-bornyl group); an aryl group such as 2,4-dinitrophenyl group (e.g., a nitro group-substituted phenyl group); an aralkyl group such as benzyl group, 2,6-dichlorobenzyl group, 2-nitrobenzyl group and triphenylmethyl group (e.g., a mono to tri$C_{6-10}$aryl-$C_{1-4}$alkyl group which may have a substituent); an oxacycloalkyl group which may have a substituent (e.g., a five- or eight-membered oxacycloalkyl group), such as a tetrahydrofuranyl group which may have a substituent (e.g., tetrahydrofuran-3-yl group and 3-methyl-tetrahydrofuran-3-yl group) and a tetrahydropyranyl group which may have a substituent (e.g., tetrahydropyran-3-yl group and 3-methyltetrahydropyran-3-yl group); a lactone ring group which may have a substituent, such as a γ-butyrolactone ring group which may have a substituent (e.g., tetrahydro-2-furanone-4-yl group and 4-methyltetrahydro-2-furanone-4-yl group), a δ-valerolactone ring group which may have a substituent (e.g., tetrahydro-2-pyron-4-yl group and 4-methyltetrahydro-2-pyron-4-yl group); a carbamoyl group which may have a substituent (e.g., an alkyl group and an aryl group) [for example, carbamoyl group; an N—$C_{1-6}$alkyl-carbamoyl group such as N-methylcarbamoyl and N-ethylcarbamoyl groups (preferably an N—$C_{1-4}$alkyl-carbamoyl group); a $C_{6-10}$aryl-carbamoyl group such as phenylcarbamoyl group]; a $diC_{1-4}$alkylphosphinothioyl group such as dimethylphosphinothioyl group; and a $diC_{6-10}$arylphosphinothioyl group such as diphenylphosphinothioyl group.

In particular, as the protective group, a hydrophobic protective group which imparts hydrophobicity to a hydrophilic group is preferable. For example, as the protective group for a hydroxyl group, there may be preferably exemplified an acyl group (especially, a $C_{1-6}$alkyl-carbonyl group such as t-butylcarbonyl group, and 2,2-dimethyipropionyl group), an alkoxycarbonyl group (a $C_{1-6}$alkoxy-carbonyl group such as t-BOC group), a five- or six-membered oxacycloalkyl group (e.g., a tetrahydropyranyl group), a bi- or tricycloalkyl group which may have a substituent (e.g., a norbornyl group which may have a substituent, such as 2-norbomyl group and 2-methyl-2-norbomyl group, an adamantyl group which may have a substituent, such as 2-adamantyl group and 2-methyl-2-adamantyl group), an alkoxyalkyl group (e.g., a $C_{1-6}$alkoxy-$C_{1-6}$alkyl group such as 1-methoxyethyl group, 1-ethoxyethyl group, 1-ethoxypropyl group and 1-methoxy-isopropyl group (especially a $C_{1-4}$alkoxy-$C_{1-4}$alkyl group)), and a $C_{1-4}$alkylsilyl group. As the protective group for carboxyl group, there maybe preferably mentioned an alkyl group (a $C_{1-4}$alkyl group such as t-butyl group), a bi- or tricycloalkyl group which may have a substituent (e.g., a crosslinked cyclic alicyclic hydrocarbon group, for example, a norbomyl group which may have a substituent, such as 2-norbomyl group and 2-methyl-2-norbomyl group, an adamantyl group which may have a substituent, such as 2-adamantyl group and 2-methyl-2-adamantyl group), a five- or six-membered oxacycloalkyl group which may have a substituent, a lactone ring group which may have a substituent, and a carbamoyl or N-substituted carbamoyl group.

The photoactive compounds may have at least one hydrophilic group X (a hydrophilic group protected by a protective group, -X-Pro) or may have a plurality of hydrophilic groups X (or -X-Pro). That is, n of the unit in the formulae (1) and (2) need only be an integer of not less than 1, and can be usually selected within the range from about 1 to 10, preferably about 1 to 8 (e.g., about 1 to 4), more preferably about 1 to 7 (e.g., about 1 to 3) according to the structure of the hydrophobic unit.

With exemplifying compounds having hydroxyl group, carboxyl group or others as the hydrophilic group X, a compound corresponding to a unit (A-X) is exemplified below.

As a compound having hydroxyl group, there may be mentioned an aliphatic alcohol (a $C_{6-10}$alkanol such as hexanol and octanol), an aromatic hydroxy compound [a phenol such as phenol and an alkylphenol (e.g., a $C_{1-12}$alkyl-phenol such as a hydroxytoluene, a hydroxyxylene, an ethylphenol, a propylphenol, an isopropylphenol, an n-butylphenol, a s-butylphenol, a t-butylphenol, a hexylphenol, an octylphenol and a nonylphenol), a $C_{6-10}$aryl alcohol such as naphthol (especially a phenol); an aralkyl alcohol such as a benzyl alcohol and a phenethyl alcohol (e.g., a $C_{6-10}$aryl-$C_{1-4}$alkanol)], an alicyclic alcohol [e.g., a monocyclic alicyclic alcohol (e.g., a $C_{5-8}$cycloalkanol such as cyclohexanol; a $C_{5-8}$cycloalkenol such as cyclohexenyl alcohol; a $C_{5-8}$cycloalkyl-$C_{1-4}$alkanol such as cyclohexyl methanol), a crosslinked cyclic alicyclic alcohol (e.g., a bi- or tricycloalkanol such as a norbornyl alcohol and an adamantyl alcohol)], and a heterocyclic alcohol [e.g., a five- or six-membered unsaturated heterocyclic alcohol such as a hydroxypyridine; a five- or six-membered saturated heterocyclic alcohol such as a hydroxyoxacyclohexane (especially a hydroxyoxacycloalkane)]. The compound having hydroxyl group also includes the above mentioned bisphenols and polykisphenols, and phenols having fluorene-core, and others.

As a compound having carboxyl group, there may be exemplified an aliphatic carboxylic acid (e.g., a $C_{4-12}$aliphatic carboxylic acid such as butyric acid, valeric acid, pivalic acid and lauric acid, especially a $C_{6-12}$aliphatic carboxylic acid), an aromatic carboxylic acid (e.g., a $C_{6-10}$aryl-carboxylic acid such as benzoic acid and a naphthalenecarboxylic acid; a $C_{5-6}$cycloalkyl-$C_{6-10}$aryl-carboxylic acid such as cyclohexylbenzoic acid; a $C_{6-10}$arylester of a $C_{6-10}$aryl-carboxylic acid having a carboxyl group such as a phenyl carboxybenzoate and a phenylcarbonyloxybenzoic acid; a $C_{6-10}$aryl-carboxylic acid which has a heterocyclic group, such as a pyridylbenzoic acid, a pyrimidinylbenzoic acid, a pyridazinyl benzoic acid and a pyridylethynylbenzoic acid; a biphenylcarboxylic acid; and a carboxyphenylethynylbenzene), an alicyclic carboxylic acid (e.g., a carboxy$C_{5-6}$cycloalkane such as carboxycyclohexane and phenylcyclohexanecarboxylic acid), and a heterocyclic carboxylic acid (e.g., a pyridinecarboxylic acid).

The hydrophobic unit may be a chain unit, and the hydrophobic unit containing at least a ring unit (especially an alicyclic hydrocarbon unit and an aromatic hydrocarbon unit) can realize improvement in resistance for dry etching, and the hydrophobic unit containing an alicyclic hydrocarbon unit can attain improvement in sensitivity and resolution. The hydrophobic unit containing such a ring unit may be represented, for example, by the following formulae (3a) to (8a). Moreover, the photoactive compounds having the hydrophobic unit represented by the formulae (3a) to (8a) may be represented by the following formulae (3b) to (8b).

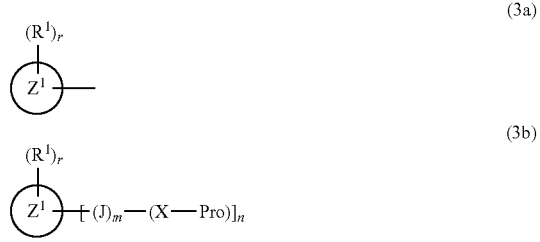

In the formulae (3a) and (3b), $Z^1$ is the same or different, each representing a hydrocarbon ring or a heterocycle, $R^1$ is the same or different, each representing a halogen atom, an alkyl group, an alkoxy group, an alkoxycarbonyl group, a cycloalkyl group, an aryl group, an aralkyl group, or a silicon-containing group, r represents an integer of 0 or not less than 1, and J, m, X, Pro and n have the same meanings defined above.

As the hydrocarbon ring represented by $Z^1$, there may be mentioned an alicyclic and aromatic hydrocarbon exemplified in the section (item) of A (a $C_{4-40}$alicyclic hydrocarbon and a $C_{6-40}$aromatic hydrocarbon), there may be preferably mentioned a cycloalkane ring (a $C_{4-8}$cycloalkane ring such as cyclohexane ring) and an aromatic hydrocarbon ring (a $C_{6-10}$arene ring such as benzene ring and a naphthalene ring). As the heterocycle, there may be mentioned a heterocycle exemplified in the section of A, there may be preferably mentioned a nonaromatic heterocycle (a nonaromatic nitrogen-containing heterocycle such as a pyrroline ring, a piperidine ring and a piperazine ring), an aromatic heterocycle (an aromatic nitrogen-containing heterocycle such as a pyrrole ring, a pyridine ring, a pyridazine ring, a pyrimidine ring and a pyrazine ring).

$R^1$ is comparable to a substituent of the hydrophobic unit, and there may be mentioned a halogen atom, an alkyl group, an alkoxy group, an alkoxycarbonyl group, a cycloalkyl group, an aryl group, an aralkyl group or a silicon-containing group which are exemplified in the section of the above-mentioned substituent. $R^1$ is usually the same or different, each representing a halogen atom, an alkyl group, an alkoxy group, a cycloalkyl group, or a silicon-containing group. When the substituent of the hydrophobic unit such as $R^1$ is a cycloalkyl group, an aryl group, fluorine atom, a silicon-containing group and the like, resistance for dry etching can be further improved. r represents 0 or an integer of not less than 1 (e.g., 1 to 6, preferably 1 to 4). The connecting group J is usually an alkylene group, an alkenylene group or an alkynylene group, and m is 0 or 1.

In the compounds represented by the formula (3b), n is usually about 1 to 10 (preferably about 1 to 6, more preferably about 1 to 4, and especially about 1 to 3).

As the compounds corresponding to the formula (3a), for example, there may be exemplified a monohydric phenol [e.g., a phenol, an alkylphenol (a $C_{1-12}$alkyl-phenol such as a cresol and a hydroxyxylene), a halogenated phenol (e.g., 4-bromophenol, 4-chlorophenol, and tetrafluorophenol), an alkoxyphenol (a $C_{1-12}$alkoxy-phenol), a nitrophenol, a naphthol, an alkylnaphthol (a $C_{1-12}$alkyl-naphthol), a halogenated naphthol, and an alkoxynaphthol], a dihydric phenol [catechol, resorcin (resorcinol), hydroquinone, a halogenated dihydric phenol (e.g., 2,4-difluorohydroquinone and 2,3,5,6-tetrafluorohydroquinone), a naphthalenediol], a trihydric phenol [e.g., pyrogallol, phloroglucin (phloroglucinol) and a naphthalenetriol], and an alicyclic alcohol corresponding to these phenols. The compound corresponding to the formula (3a) also includes the crosslinked cyclic alicyclic alcohol, the aralkyl alcohol and the heterocyclic alcohol. Further, the compound corresponding to the formula (3a) includes a carboxyl group-containing compound corresponding to the hydroxyl group-containing compound.

The compound corresponding to the formula (3a) also includes a compound having a hydroxyalkyl group, for example, a monohydroxymethyl-phenol (a $C_{1-10}$alkylphenol having a hydroxymethyl group such as 4-hydroxymethyl-2,5-dimethylphenol, 2-cyclohexyl-4-hydroxymethyl-5-methylphenol and 2-t-butyl-4-hydroxymethyl-5-methylphenol), a phenol having a plurality of hydroxymethyl groups (a $C_{1-10}$alkylphenol having a plurality of hydroxymethyl groups such as 2,6-dihydroxymethyl-4-methylphenol, 2,4-dihydroxymethyl-6-methylphenol, 2,6-dihydroxymethyl-3,4-dimethylphenol, 4-t-butyl-2,6-dihydroxymethylphenol, 4-cyclohexyl-2,6-dihydroxymethylphenol and 4,6-dihydroxymethyl-2-isopropylphenol.

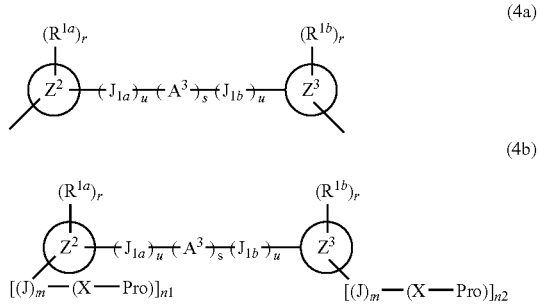

In the formulae (4a) and (4b), $Z^2$ and $Z^3$ are the same or different, each representing a hydrocarbon ring or a heterocycle, $A^3$ represents a connecting group selected from the group consisting of an alkylene group, an alkenylene group, an alkynylene group, a cycloalkylene group, an arylene group, an oxyalkylene group, an alkyleneoxy group, an ether group, a thioether group, a carbonyl group, an ester group (a carbonyloxy group and a oxycarbonyl group), an amide group, a urethane group, a urea group and a sulfonyl group, and s and u are the same or different, each denoting 0 or 1. $J_{1a}$ and $J_{1b}$ are the same or different, each representing a connecting group different from $A^3$, $R^{1a}$ and $R^{1b}$ are the same or different, each representing a halogen atom, an alkyl group, an alkoxy group, an alkoxycarbonyl group, a cycloalkyl group, an aryl group, an aralkyl group or a silicon-containing group, each of the factors, n1 and n2, independently represents 0 or an integer of not less than 1, and n1+n2≧1. J, r, m, X and Pro have the same meanings defined above.

As the rings $Z^2$ and $Z^3$, there may be exemplified the same hydrocarbon rings as the ring $Z^1$ (a $C_{4-40}$alicyclic hydrocarbon ring or a $C_{6-40}$aromatic hydrocarbon ring) or a heterocycle (especially a $C_{4-8}$cycloalkane ring such as cyclohexane ring, a $C_{6-10}$arene ring such as a benzene ring). The connecting group $A^3$ may be the same as the above-exemplified connecting group J. As the alkylene group as the connecting group $A^3$, there may be mentioned a linear- or branched alkylene group such as methylene, ethylene, dimethylmethylene, di(trifluoromethyl)methylene, isopropylene and t-butylene groups (e.g., a $C_{1-6}$alkylene group). As the alkenylene group, there may be mentioned a $C_{2-4}$alkenylene group such as vinylene group, and as the alkynylene group, there may be mentioned a $C_{2-4}$alkynylene group such as ethynylene group. As the cycloalkylene group, there may be exemplified a $C_{4-8}$cycloalkylene group such as cyclohexylene group. As the arylene group, there may be mentioned a $C_{6-10}$arylene group such as phenylene and naphthylene groups, and the arylene group includes a condensed hydrocarbon ring group such as a fluorene-9,9-diyl group. As the oxyalkylene group or an alkyleneoxy group, there may be mentioned a linear- or branched oxyalkylene group (e.g., an oxy$C_{1-6}$alkylene group), or a linear- or branched alkyleneoxy group (e.g., a $C_{1-6}$alkyleneoxy group) corresponding to the alkylene group. The connecting group $A^3$ (especially an alkylene group) may have a substituent such as the above-exemplified substituents, for example, a halogen atom such as a fluorine atom, an alkyl group (e.g., a $C_{1-6}$alkyl group), a cycloalkyl group (e.g., a $C_{5-8}$cycloalkyl group) and an aryl group (e.g., a phenyl group). Moreover, these substituents may further have a substituent, for example, may be a cycloalkyl group having a substituent, an aryl group having a substituent (e.g., a hydroxyphenyl group, an alkylphenyl group, an alkoxyphenyl group and a halophenyl group); the alkylphenyl group may be a tolyl group, a xylyl group or a t-butylphenyl group; the alkoxyphenyl group may be a methoxyphenyl group, an ethoxyphenyl group or a t-butoxyphenyl group; or the halophenyl group may be a bromophenyl group, a chlorophenyl group, or a fluoropheyl group. The aryl group (especially phenyl group) substituted to an alkylene group of the connecting group A does not usually have a hydroxyl group.

As the connecting groups $J_{1a}$ and $J_{1b}$, as far as they are different from each other, there may be mentioned the same connecting group as the connecting group $A^3$, for example, a linear- or branched alkylene group (e.g., a $C_{1-6}$alkylene group) such as methylene, ethylene, dimethylmethylene, di(trifluoromethyl)methylene, isopropylene and t-butylene groups. The connecting groups $J_{1a}$ and $J_{1b}$ may have a substituent (the same substituent as the $R^1$), for example, a halogen atom, an alkyl group (e.g., a $C_{1-6}$alkyl group), a cycloalkyl group (e.g., a $C_{5-8}$cycloalkyl group), and an aryl group (e.g., a phenyl group). Moreover, these substituents (an alkyl group, a cycloalkyl group and an aryl group) may further have a substituent; for example, an alkyl group having a substituent (an arylalkyl or cycloalkylalkyl group wherein a hydrocarbon ring may have at least one substituent selected from a hydroxyl group, an alkyl group and a halogen atom, for example, a phenyl$C_{1-6}$alkyl group, a hydroxyphenyl$C_{1-6}$alkyl group, an alkylphenyl$C_{1-6}$alkyl group, an alkylhydroxyphenyl$C_{1-6}$alkyl group, and a halophenyl$C_{1-6}$alkyl group), a cycloalkyl group having a substituent (a cycloalkyl group which may have at least one substituent selected from a hydroxyl group, an alkyl group and a halogen atom, for example, a hydroxycycloalkyl group, an alkylcyclohexyl group and an alkylhydroxycyclohexyl group), an aryl group having a substituent (an aryl group which may have at least one substituent selected from a hydroxyl group, an alkyl group and a halogen atom, for example, a hydroxyphenyl group, an alkylphenyl group and an alkylphenol group). The alkylphenyl group may be a tolyl group, a xylyl group and a t-butylphenyl group, and the alkylphenol group may be a methylhydroxyphenyl group, a dimethylhydroxyphenyl group and a t-butylhydroxyphenyl group.

s and u may be 0 all together (that is, the rings $Z^2$ and $Z^3$ may directly bond), may be s=1 and u=0, may be s=0 and u=1, or may be s=1 and u=1.

Further, as the $R^{1a}$ and $R^{1b}$, the same substituent as the $R^1$ may be exemplified. Concerning each of the rings, $Z^2$ and $Z^3$, the number r of the substituents $R^1$ may be 0 or about 1 to 6 (e.g., about 1 to 4) in a similar manner as the formula (3a).

Incidentally, in the case where the connecting group $A^3$ is direct bonding, an alkylene group, an alkenylene group, an alkynylene group, an oxyalkylene group, an alkyleneoxy group, an ether group, a thioether group, a carbonyl group, an ester group (a carbonyloxy group and an oxycarbonyl group), an amide group, a urethane group, a urea group or a sulfonyl group, u is usually 0, and in the case where the connecting group $A^3$ is a cycloalkylene group or an arylene group, u is usually 1. Moreover, when the connecting group $A^3$ is a cycloalkylene group or an arylene group, each of the connecting groups, $J_{1a}$ and $J_{1b}$, is usually direct bonding or an alkylene group.

In the compound represented by the formula (4b), the summation of n1 and n2 is about 1 to 10 (preferably about 1 to 6 (e.g., about 1 to 4), more preferably about 2 to 6 (e.g., about 2 to 4)).

As a compound corresponding to the formula (4a) (a compound having a hydrophobic unit represented by $Z^2$-$(J_{1a})_u$-$(A^3)_s$-$(J_{1b})_u$-$Z^3$), for example, the following compounds may be exemplified;

(a) a biphenol:
biphenol, bis(3-methyl-4-hydroxy)biphenyl, bis(2,3,5-trimethyl-4-hydroxy)biphenyl, bis(3,5-di-t-butyl-2-hydroxy)biphenyl, bis(3-allyl-4-hydroxy)biphenyl, bis(3-fluoro-4-hydroxy)biphenyl, bis(3,5-difluoro-4-hydroxy)biphenyl, 3-benzoimidazolyl-4,4'-dihydroxybiphenyl, bis(3-benzoimidazolyl-4-hydroxy)biphenyl, 3,3',5,5'-tetramethyl-4,4'-dihydroxybiphenyl, and 3,3',5,5'-tetra-t-butyl-4,4'-dihydroxybiphenyl;

(b) a bis(hydroxyaryl)alkane:
(b-1) a bis(hydroxyaryl)methane, for example, bis(4-hydroxyphenyl)methane, bis(2-hydroxyphenyl)methane, bis(4-hydroxy-3-methylphenyl)methane, bis(2-hydroxy-3-methylphenyl)methane, bis(3-ethyl-4-hydroxyphenyl)methane, bis(4-hydroxy-2-methylphenyl)methane, bis(2-hydroxy-5-methylphenyl)methane, bis(2-hydroxy-5-isopropylphenyl)methane, bis(4-hydroxy-2,3-dimethylphenyl)methane, bis(2-hydroxy-3,5-dimethylphenyl)methane, bis(4-hydroxy-3,5-dimethylphenyl)methane, bis(4-hydroxy-2,5-dimethylphenyl)methane, bis(4-hydroxy-3,5-di-isobutylphenyl)methane, bis(4-hydroxy-3,5-di-t-butylphenyl)methane, bis(4-hydroxy-2,6-dimethylphenyl)methane, bis(4-hydroxy-2,3,5-trimethylphenyl)methane, bis(4-phenyl-2-hydroxyphenyl)methane, bis(3-cyclohexyl-2-hydroxyphenyl)methane, bis(2-methyl-3-cyclohexyl-4-hydroxyphenyl)methane, bis(4,5-dihydroxy-2-methylphenyl)methane, bis(3-allyl-4-hydroxyphenyl)methane, 2',4-dihydroxydiphenylmethane, 4,4',5-trihydroxy-2-methyldiphenylmethane, 2',4-dihydroxy-3,5-dimethyldiphenylmethane, 2,3,4,4'-tetrahydroxy-3',5'-dimethyldiphenylmethane, 2,3,4,4'-tetrahydroxy-2',3',5'-trimethyldiphenylmethane, 2,3,4,4'-tetrahydroxydiphenylmethane, 2,4,4'-trihydroxy-3',5'-dimethyldiphenylmethane, 2,4,4'-trihydroxy-3,3',5'-trimethyldiphenylmethane, 4,4',5-trihydroxy-2,3',5'-trimethyldiphenylmethane, and 2,3,4,4'-tetrahydroxy-3',5'-dimethyldiphenylmethane;

(b-2) an aryl-bis(hydroxyaryl)methane, for example, 1-phenyl-1,1-bis(4-hydroxyphenyl)methane, 1-phenyl-1,1-bis(4-hydroxy-3-methylphenyl)methane, 1-phenyl-1,1-bis(3-cyclohexyl-4-hydroxyphenyl)methane, 1-biphenyl-1,1-bis(4-hydroxy-3-methylphenyl)methane, 1-(4-methylphenyl)-1,1-bis(4-hydroxy-2,3,5-trimethylphenyl)methane, 1-(4-methylphenyl)-1,1-bis(4-hydroxy-2,3,6-trimethylphenyl)methane, 1-(4-isopropylphenyl)-1,1-bis(4-hydroxy-2,3,5-trimethylphenyl)methane, 1-(2-methoxyphenyl)-1,1-bis(4-hydroxy-2,3,6-trimethylphenyl)methane, 1-(4-methoxyphenyl)-1,1-bis(4-hydroxy-2,3,6-trimethylphenyl)methane, 1-(4-methoxyphenyl)-1,1-bis(4-hydroxy-2,3,5-trimethylphenyl)methane, 1-(4-fluorophenyl)-1,1-bis(3-fluoro-4-hydroxyphenyl)methane, 1,1-diphenyl-1,1-bis(4-hydroxyphenyl)methane, bis(4,5-dihydroxy-2-methylphenyl)phenylmethane, bis(5-chloro-2,4-dihydroxyphenyl)phenylmethane, bis(5-chloro-2,4-dihydroxyphenyl)-4-ethylphenylmethane, bis(5-chloro-2,4-dihydroxyphenyl)-4-t-butylphenylmethane, and bis(4,5-dihydroxy-2-t-butylphenyl)phenylmethane;

(b-3) a bis(hydroxyaryl)ethane, for example, 1,1-bis(4-hydroxyphenyl)ethane, 1,2-bis(4-hydroxyphenyl)ethane, 1,2-bis(3,5-di-t-butyl-4-hydroxyphenyl)

ethane, 1,1-bis(4-hydroxy-3,5-dimethylphenyl)ethane, 1,1-bis(2-hydroxy-5-t-butylphenyl)ethane, 1,1-bis(4-hydroxy-3,5-di-t-butylphenyl)ethane, 1,1-bis(2-hydroxy-5-methylphenyl)ethane, 1,1-bis(2-methyl-5-cyclohexyl-4-hydroxyphenyl)ethane, 1,1-bis(3-allyl-4-hydroxyphenyl)ethane, and 1,1-bis(5-chloro-2,4-dihydroxyphenyl)ethane;

(b-4) an aryl-bis(hydroxyaryl)ethane, for example, 1-phenyl-1,1-bis(4-hydroxyphenyl)ethane, 1-phenyl-1,1-bis(4-hydroxy-3-methylphenyl)ethane, 1-phenyl-1,1-bis(4-hydroxy-3-isopropylphenyl)ethane, 1-phenyl-1,1-bis(4-hydroxy-3-t-butylphenyl)ethane, and 1-(4-nitrophenyl)-1,1-bis(4-hydroxyphenyl)ethane;

(b-5) a bis(hydroxyaryl)propane, for example, 2,2-bis(4-hydroxyphenyl)propane, 1,1-bis(4-hydroxyphenyl)propane, 2,2-bis(3-methyl-4-hydroxyphenyl)propane, 2,2-bis(3,5-dimethyl-4-hydroxyphenyl)propane, 2,2-bis(3,5-di-t-butyl-4-hydroxyphenyl)propane, 2,2-bis(3,5-dimethyl-2-hydroxyphenyl)propane, 2,2-bis(3-allyl-4-hydroxyphenyl)propane, 2,2-bis(3-allyl-4-hydroxy-5-methylphenyl)propane, 2,2-bis(3-(1-methylethyl)-4-hydroxyphenyl)propane, 2,2-bis(3-(1-methylpropyl)-4-hydroxyphenyl)propane, 2,2-bis(3-(1,1-dimethylethyl)-4-hydroxyphenyl)propane, 1,1-bis(3-cyclohexyl-4-hydroxyphenyl)propane, 2,2-bis(3-cyclohexyl-4-hydroxyphenyl)propane, t-butylated bisphenolA, 2,2-bis(3-fluoro-4-hydroxyphenyl)propane, 2,2-bis(4-hydroxyphenyl)hexafluoropropane, 2,2-bis(3-nitro-4-hydroxyphenyl)propane, 2-(4-hydroxyphenyl)-2-(2-hydroxyphenyl)propane, 2-(4-hydroxyphenyl)-2-(3-hydroxyphenyl)propane, 2-(4-hydroxyphenyl)-2-(2,4-dihydroxyphenyl)propane, 2-(4-hydroxyphenyl)-2-(2,4-dihydroxy-3-methylphenyl)propane, 2-(4-hydroxyphenyl)-2-(2,5-dihydroxyphenyl)propane, 2-(4-hydroxyphenyl)-2-(3-cyclohexyl-4-hydroxyphenyl)propane, 2-(4-hydroxyphenyl)-2-(5-cyclohexyl-4-hydroxy-2-methylphenyl)propane, 2,2-bis(2,4-dihydroxy-3-methylphenyl)propane, and 1,1-bis(5-chloro-2,4-dihydroxyphenyl)propane;

(b-6) a bis(hydroxyaryl)$C_{4-10}$alkane, for example, 1,1-bis(4-hydroxyphenyl)butane, 2,2-bis(4-hydroxyphenyl)butane, 2,2-bis(3-cyclohexyl-4-hydroxyphenyl)butane, 1,1-bis(5-cyclohexyl-4-hydroxy-2-methylphenyl)butane, 1,1-bis(4-hydroxyphenyl)-2-methylpropane, 1,1-bis(2-methyl-4-hydroxy-5-cyclohexylphenyl)-2-methylpropane, 1,1-bis(3,5-dimethyl-4-hydroxyphenyl)-2-methylpropane, 1,1-bis(4-hydroxy-3-methylphenyl)butane, 1,1-bis(5-chloro-2,4-dihydroxyphenyl)butane, 1,1-bis(4-hydroxyphenyl)pentane, 3,3-bis(4-hydroxyphenyl)pentane, 3,3-bis(4-hydroxy-3-methylphenyl)pentane, 2,2-bis(4-hydroxy-3-methylphenyl)-4,4-dimethylbutane, 2,2-bis(4-hydroxyphenyl)hexane, 1,1-bis(4-hydroxyphenyl)octane, 2,2-bis(4-hydroxyphenyl)octane, and 1,1-bis(4-hydroxyphenyl)decane;

(c) a bis(hydroxyaryl)cycloalkane:
1,1-bis(4-hydroxyphenyl)cyclopentane, 1,1-bis(4-hydroxy-3-methylphenyl)cyclopentane, 1,1-bis(4-hydroxy-3,5-dimethylphenyl)cyclopentane, 1,1-bis(4-hydroxy-3-isopropylphenyl)cyclopentane, 1,1-bis(4-hydroxy-3-t-butylphenyl)cyclopentane, 1,1-bis(4-hydroxyphenyl)cyclohexane, 1,1-bis(4-hydroxyphenyl)-4-methylcyclohexane, 1,1-bis(4-hydroxyphenyl)-4-isopropylcyclohexane, 1,1-bis(3-methyl-4-hydroxyphenyl)-4-isopropylcyclohexane, 1,1-bis(4-hydroxyphenyl)-4-butylcyclohexane, 1,1-bis(4-hydroxy-3-methylphenyl)cyclohexane, 1,1-bis(4-hydroxy-3-t-butylphenyl)cyclohexane, 1,1-bis(4-hydroxy-3,5-dimethylphenyl)cyclohexane, 1,1-bis(4-hydroxy-3,5-dimethylphenyl)-4-isopropylcyclohexane, 1,1-bis(4-hydroxy-3,5-dimethylphenyl)-3,3,5-trimethylcyclohexane, 1,1-bis(3-phenyl-4-hydroxyphenyl)cyclohexane, 1,1-bis(3-cyclohexyl-4-hydroxyphenyl)cyclohexane, 1,1-bis(3-allyl-4-hydroxyphenyl)cyclohexane, and the like;

(d) a compound (bisphenol) in which $A^3$ is carbonyl group (e.g., a dihydroxy aryl ketone such as 4,4'-dihydroxy diphenyl ketone, and (2,3,4-trihydroxy-phenyl)(4'-hydroxy-phenyl)ketone), a compound in which $A^3$ is oxygen atom (e.g., 4,4'-dihydroxy diphenyl ether), a compound in which $A^3$ is sulfonyl group (e.g., 4,4'-dihydroxy diphenyl sulfone), a bisphenol having an ester group, an alkyleneoxy group, an oxyalkylene group, an amide group, and others;

(e) a bisphenol in which $A^3$ is a benzene ring, and each of the connecting groups, $J_{1a}$ and $J_{1b}$, is an alkylene group (a bis[(hydroxyaryl)alkyl]arene), for example, 1,4-bis(2,4-dihydroxybenzyl)benzene, 1,3-bis[1-(2,4-dihydroxyphenyl)isopropyl]benzene, 1,3-bis[1-(3-methyl-4-hydroxyphenyl)isopropyl]benzene, 1,3-bis[1-(5-methyl-2-hydroxyphenyl)isopropyl]benzene, 1,3-bis[1-(3-methyl-4-hydroxyphenyl)isopropyl]benzene, 1,3-bis[1-(3,5-dimethyl-4-hydroxyphenyl)isopropyl]benzene, 1,3-bis[1-(2,3,5-trimethyl-4-hydroxyphenyl)isopropyl]benzene, 1,4-bis[1-(2,3,5-trimethyl-4-hydroxyphenyl)isopropyl]benzene, 1,3-bis[1-(2-methyl-5-cyclohexyl-4-hydroxyphenyl)isopropyl]benzene, 1,4-bis[1-(2-methyl-5-cyclohexyl-4-hydroxyphenyl)isopropyl]benzene, 1,3-bis[1-(3,4-dihydroxyphenyl)isopropyl]benzene, 1,3-bis[1-(3,4,5-trihydroxyphenyl)isopropyl]benzene, 1,3-bis[1-(3-methyl-2,4-dihydroxyphenyl)isopropyl]benzene, 1,3-bis[1-(3-chloro-2,6-dihydroxyphenyl)isopropyl]benzene, 1,4-bis[1-(2,4-dihydroxyphenyl)isopropyl]benzene, 1,4-bis[1-(3-methyl-2,4-dihydroxyphenyl)isopropyl]benzene, 1,4-bis[(3,5-dimethyl-4-hydroxyphenyl)methyl]benzene, 1,4-bis[(2,3,5-trimethyl-4-hydroxyphenyl)methyl]benzene, and 4,4'-bis(2,4-dihydroxybenzyl)biphenyl;

(f) a compound having a hydroxyalkyl group or a formyl group, for example, a bis- or tris(hydroxyaryl)alkane having a hydroxymethyl group and/or a formyl group such as bis(4-hydroxy-3-hydroxymethyl-5-methylphenyl)methane, bis(4-hydroxy-3-hydroxymethyl-2,5-dimethylphenyl)methane, bis(4-hydroxy-5-hydroxymethyl-2,3-dimethylphenyl)methane, bis(2-hydroxy-3-hydroxymethyl-4,5-dimethylphenyl)methane, bis(3-formyl-4-hydroxyphenyl)methane, bis(4-hydroxy-2,5-dimethylphenyl)formylmethane, 1,1-bis(4,5-dihydroxy-2-methylphenyl)-1-(4-formylphenyl)methane, and 2,2-bis(4-hydroxy-3,5-dihydroxymethylphenyl)propane;

(g) other compounds, for example, a compound having a heterocycle [1-(furan-2-yl)-1,1-bis(3,5-dimethyl-4-hydroxyphenyl)methane, 1,3-dihydro-3,3-bis(4-hydroxyphenyl)-2H-indole-2-one, 1,3-dihydro-3,3-bis(4-hydroxy-3-methylphenyl)-2H-indole-2-one, 4-(3,4-dihydro-7-hydroxy-2,4,4-trimethyl-2H-1-benzopyran-2-yl)-1,3-benzenediol], a compound having a silyl group [e.g., 4,4'-(dimethylsilylene)bisphenol], a compound having a bridge-ring [e.g., dicyclopentadienylbis(4-methylphenol)], and a compound having a spiro ring [e.g., 4-[1-[4-(4-hydroxyphenyl)-4-methyl-cyclohexyl]-1-methylethyl]phenol, 4-[1-[4-(4-hydroxy-3-methylphenyl)-4-methylcyclohexyl]-1-methylethyl]-2-methylphenol, 4-[1-[4-(4-hydroxy-3,5-dimethylphenyl)-4-methylcyclohexyl]-1-methylethyl]-2,6-dimethylphenol, and (1,1'-bicyclohexene-3,3'-yl)-4,4'-bis(2,5-dimethylphenol)]; and (h) a bisphenol having a condensed hydrocarbon ring group (e.g., fluorene-core): a 9,9-bis(hydroxyphenyl)fluorene, for example, 9,9-bis(4-hydroxyphenyl)fluorene, 9,9-bis(2-methyl-4-hydroxyphenyl)fluorene, 9,9-bis(3-methyl-4-hydroxyphenyl)fluorene, 9,9-bis(2-hydroxy-5-methylphenyl)fluorene, 9,9-bis(2,5-dimethyl-4-hydroxyphenyl)fluorene, 9,9-bis(3,5-dimethyl-4-hydroxyphenyl)fluorene, 9,9-bis(2,6-dimethyl-4-hydroxyphenyl)fluorene, 9,9-bis(3-isopropyl-4-hydroxyphenyl)fluorene, 9,9-bis(3-isobutyl-4-hydroxyphenyl)fluorene, 9,9-bis(3-t-butyl-4-hydroxyphenyl)fluorene, 9,9-bis(3-fluoro-4-hydroxyphenyl)fluorene, 9,9-bis(3-allyl-4-hydroxyphenyl)fluorene, and 9,9-bis(4-hydroxybiphenyl)fluorene.

class methane-type trisphenol) whose ring(s) may be substituted by at least one kind of substituents selected from a halogen atom, an alkyl group, a cycloalkyl group, and an alkoxy group, for example, tris(4-hydroxyphenyl)methane, a trisphenol having an alkyl group [e.g., bis(4-hydroxy-3-methylphenyl)-4-hydroxyphenylmethane, bis(4-hydroxy-3,5-dimethylphenyl)-4-hydroxyphenylmethane, bis(4-hydroxy-2,6-dimethylphenyl)-4-hydroxyphenylmethane, bis(4-hydroxy-2,3,6-trimethylphenyl)-4-hydroxyphenylmethane, bis(4,5-dihydroxy-2-methylphenyl)-4-hydroxyphenylmethane, bis(4-hydroxyphenyl)-3-hydroxyphenylmethane, bis(4-hydroxy-2-methylphenyl)-2-hydroxyphenylmethane, bis(4-hydroxyphenyl)-3,4-di-t-butyl-4-hydroxyphenylmethane, bis(4-hydroxy-3-methylphenyl)-3,5-di-t-butyl-4-hydroxyphenylmethane, and bis(4,5-dihydroxy-2-methylphenyl)-3,5-di-t-butyl-4-hydroxyphenylmethane], a trisphenol having a cycloalkyl group [e.g., bis(5-cyclohexyl-4-hydroxy-2-methylphenyl)-4-hydroxyphenylmethane, and bis(5-cyclohexyl-4-hydroxy-2-methylphenyl)-2-hydroxyphenylmethane], a trisphenol having a halogen atom [e.g., bis(5-chloro-2,4-dihydroxyphenyl)-4-hydroxyphenylmethane, and bis(5-chloro-2,4-dihydroxyphenyl)-2-hydroxyphenylmethane], and a trisphenol having an alkoxy group [e.g., bis(4-hydroxyphenyl)-4-hydroxy-3-methoxyphenylmethane, bis(4-hydroxy-3-methylphenyl)-4-hydroxy-3-methoxyphenylmethane, bis(4-hydroxy-3-methylphenyl)-2-hydroxy-6-methoxyphenylmethane, and bis(4-hydroxy-2,5-dimethylphenyl)-2-hydroxy-6-methoxyphenylmethane].

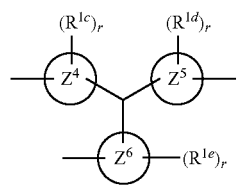

(5a)

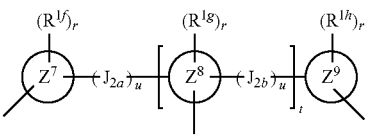

(6a)

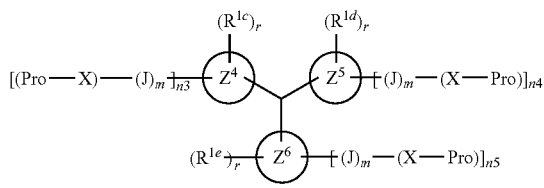

(5b)

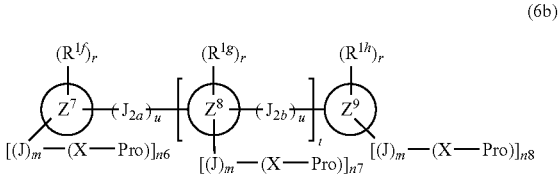

(6b)

In the formulae (5a) and (5b), $Z^4$ to $Z^6$ may be the same or different, each representing a hydrocarbon ring or a heterocycle; $R^{1c}$, $R^{1d}$ and $R^{1e}$ may be the same or different, each representing a halogen atom, an alkyl group, an alkoxy group, an alkoxycarbonyl group, a cycloalkyl group, an aryl group, an aralkyl group, or a silicon-containing group; each of the factors, n3, n4 and n5, represents 0 or an integer of not less than 1, $n3+n4+n5 \geqq 1$; and r, J, m, X and Pro have the same meanings defined above.

As the rings $Z^4$ to $Z^6$, there may be exemplified a hydrocarbon ring or a heterocycle in-line with the ring $Z^1$ in the formula (3a) (in particular, a $C_{4-8}$cycloalkane ring such as cyclohexane ring, and a $C_{6-10}$arene ring such as benzene ring). As the substituent groups $R^{1c}$, $R^{1d}$ and $R^{1e}$, there may be exemplified a substituent in-line with the $R^1$, the coefficient r of the substituents $R^{1c}$, $R^{1d}$ and $R^{1e}$ in each of the rings, $Z^4$ to $Z^6$ is the same as above.

In the compound represented by the formula (5b), summation of n3, n4 and n5 is about 1 to 10 (preferably about 1 to 9 (e.g., about 3 to 9), and more preferably about 2 to 6 (e.g., about 3 to 6)).

As the compound corresponding to the formula (5a), there may be exemplified a tris(4-hydroxyaryl)alkane (a methane- In the formulae (6a) and (6b), $Z^7$ to $Z^9$ may be the same or different, each representing a hydrocarbon ring or a heterocycle; $J_{2a}$ and $J_{2b}$ may be the same or different, each representing a connecting group; $R^{1f}$, $R^{1g}$ and $R^{1h}$ may be the same or different, each representing a halogen atom, an alkyl group, an alkoxy group, an alkoxycarbonyl group, a cycloalkyl group, an aryl group, an aralkyl group, or a silicon-containing group; t represents an integer of 1 to 5; each of the factors, n6, n7 and n8, is 0 or an integer of not less than 1, and $n6+n7 \times t+n8 \geqq 1$; and r, u, J, m, X and Pro have the same meanings defined above.

As the rings $Z^7$ to $Z^9$, there may be exemplified a hydrocarbon ring or a heterocycle in a similar manner as the formula (3a) (in particular, a $C_{4-8}$cycloalkane such as cyclohexane ring, and a $C_{6-10}$arene ring such as benzene ring). The connecting groups $J_{2a}$ and $J_{2b}$ may be exemplified as the same connecting group as the connecting group $A^3$ in the formula (4a), the connecting groups $J_1$, or the connecting groups $J_{1a}$ and $J_{1b}$, for example, a linear- or branched alkylene group (e.g., a $C_{1-6}$alkylene group), an alkenylene group (e.g., a $C_{2-4}$alkenylene group), a cycloalkylene group (e.g., a $C_{4-8}$cycloalkylene group), an arylene group (a $C_{6-10}$arylene group such as phenylene and naphthylene groups, a condensed hydrocarbon ring group such as fluorene-9,9-diyl group), carbonyl group, and sulfonyl group. The connecting groups $J_{2a}$ and $J_{2b}$ may have the same substituent as the $R^1$, for example, a halogen atom, an alkyl group (e.g., a $C_{1-6}$alkyl group), a cycloalkyl group (e.g., a $C_{5-8}$cycloalkyl group), and an aryl group (e.g., phenyl group). Moreover, these substituents (e.g., an alkyl group, a cycloalkyl group and an aryl group) may further have a substituent, as is the case with the connecting groups $J_{1a}$ and $J_{1b}$. For instance, the connecting groups $J_{2a}$ and $J_{2b}$ may be an alkyl group having a substituent (e.g., an arylalkyl or cycloalkylalkyl group whose hydrocarbon ring may have at least one kind of substituents selected from a hydroxyl group, an alkyl group and a halogen atom, for example, a phenyl$C_{1-6}$alkyl group, a hydroxyphenyl$C_{1-6}$alkyl group, an alkylphenyl$C_{1-6}$alkyl group, an alkylhydroxyphenyl$C_{1-6}$alkyl group, and a halophenyl$C_{1-6}$alkyl group), a cycloalkyl group having a substituent (e.g., a cycloalkyl group which may have at least one kind of substituents selected from a hydroxyl group, an alkyl group and a halogen atom, for example, a hydroxycycloalkyl group, an alkylcyclohexyl group, and an alkylhydroxycyclohexyl group), an aryl group having a substituent (e.g., an aryl group which may have at least one kind of substituents selected from a hydroxyl group, an alkyl group and a halogen atom, for example, a hydroxyphenyl group, an alkylphenyl group, and an alkylphenol group), and the alkylphenyl group may be a tolyl group, a xylyl group and a t-butylphenyl group, the alkylphenol group may be a methylhydroxyphenyl group, a dimethylhydroxyphenyl group and a t-butylhydroxyphenyl group.

The connecting groups $J_{2a}$ and $J_{2b}$ is usually a linear- or branched alkylene group (e.g., a $C_{1-6}$alkylene group); a linear- or branched alkylene group (e.g., a $C_{1-6}$alkylene group) which is substituted by a cycloalkyl group which may have a substituent (e.g., a hydroxycycloalkyl group), or an aryl group which may have a substituent (e.g., an alkylphenyl group, an alkoxyphenyl group and a halophenyl group).

t is about 1 to 5 (preferably about 1 to 4, especially about 1 to 3). u and m are 0 or 1, usually u=1. As the substituents $R^{1f}$, $R^{1g}$ and $R^{1h}$, there may be exemplified the same substituents as the $R^1$. r is the same as the formula (3a) concerning each of the rings, $Z^7$ to $Z^9$.

In the compound represented by the formula (6b), the value of "n6+n7xt+n8" is about 3 to 10 (e.g., about 3 to 8), preferably about 3 to 7 (e.g., about 3 to 6).

As the compound corresponding to the formula (6a), for example, the following compounds may be exemplified;

(i) a linear trisphenol:
a trisphenol in which phenol units are bonded or connected through connecting groups $J_{2a}$ and $J_{2b}$, and a ring may be substituted by at least one kind of substituents selected from a halogen atom, an alkyl group, a cycloalkyl group and an alkoxy group (e.g., a bis(hydroxybenzyl)-hydroxybenzene), for example, 1,5-bis(4-hydroxybenzyl)-2,4-dihydroxybenzene, a trisphenol having an alkyl group [e.g., 2,4-bis(4-hydroxybenzyl)-6-methylphenol, 2,4-bis(4-hydroxy-3-methylbenzyl)-6-methylphenol, 2,4-bis(4-hydroxy-2-methylbenzyl)-6-methylphenol, 2,4-bis(4-hydroxy-3,5-dimethylbenzyl)-6-methylphenol, 2,4-bis(2,4-dihydroxybenzyl)-6-methylphenol, 2,6-bis(4-hydroxybenzyl)-4-methylphenol, 2,6-bis(4-hydroxy-2-methylbenzyl)-4-methylphenol, 2,6-bis(4-hydroxy-2,5-dimethylbenzyl)-4-methylphenol, 2,6-bis(4-hydroxy-3,5-dimethylbenzyl)-6-methylphenol, 2,4-bis(4-hydroxybenzyl)-6-ethylphenol, 2,4-bis(4-hydroxy-3,5-dimethylbenzyl)-6-ethylphenol, 2,6-bis(4-hydroxybenzyl)-4-t-butylphenol, 2,6-bis(4-hydroxy-3-methylbenzyl)-4-t-butylphenol, 2,6-bis(2,4-dihydroxybenzyl)-4-methylphenol, 2,6-bis(2,3,4-trihydroxybenzyl)-4-methylphenol, 2,6-bis(2,4-dihydroxybenzyl)-4-t-butylphenol, 2,6-bis(4-hydroxybenzyl)-3,4-dimethylphenol, 2,4-bis(2,4-dihydroxybenzyl)-6-isopropylphenol, 2,6-bis(2,4-dihydroxybenzyl)-4-amylphenol, and 1,5-bis(4-hydroxy-3,5-dimethylbenzyl)-2,4-dihydroxy-3-methylbenzene], a trisphenol having a cycloalkyl group [e.g., 2,4-bis(4-hydroxybenzyl)-6-cyclohexylphenol, 2,4-bis(2,4-dihydroxybenzyl)-6-cyclohexylphenol, 2,6-bis(4-hydroxybenzyl)-4-cyclohexylphenol, 2,6-bis(4-hydroxy-2,5-dimethylbenzyl)-4-cyclohexylphenol, and 2,6-bis(2,4-dihydroxybenzyl)-4-cyclohexylphenol], an allyl group-containing trisphenol [e.g., 2,4-bis(3-allyl-4-hydroxybenzyl)-6-methylphenol], and a halogen-containing trisphenol [e.g., 2,6-bis(5-chloro-2,4-dihydroxybenzyl)-4-methylphenol];

(ii) a linear tetrakisphenol:
a tetrakisphenol in which phenol units are bonded or connected through the connecting groups $J_{2a}$ and $J_{2b}$, and a ring may be substituted by at least one kinds of substituents selected from a halogen atom, an alkyl group, a cycloalkyl group and an alkoxy group (e.g., a bis[hydroxy-(hydroxybenzyl)-phenyl]alkane), for example, bis[4-hydroxy-3-(4-hydroxybenzyl)-5-methylphenyl]methane, bis[4-hydroxy-3-(4-hydroxy-3-methylbenzyl)-5-methylphenyl]methane, bis[4-hydroxy-3-(2-hydroxy-3,5-dimethylbenzyl)-5-methylphenyl]methane, bis[4-hydroxy-3-(4-hydroxy-2,5-dimethylbenzyl)-5-methylphenyl]methane, bis[4-hydroxy-3-(4-hydroxy-3,5-dimethylbenzyl)-5-methylphenyl]methane, bis[4-hydroxy-3-(4-hydroxy-2,6-dimethylbenzyl)-5-methylphenyl]methane, bis[4-hydroxy-3-(4-hydroxy-2,3,6-trimethylbenzyl)-5-methylphenyl]methane, bis[4-hydroxy-3-(5-cyclohexyl-4-hydroxy-2-methylbenzyl)-5-methylphenyl]methane, bis[4-hydroxy-3-(3-cyclohexyl-4-hydroxybenzyl)-5-methylphenyl]methane, bis[4-hydroxy-3-(5-t-butyl-2-hydroxybenzyl)-5-methylphenyl]methane, bis[4-hydroxy-3-(2,4-dihydroxybenzyl)-5-methylphenyl]methane, bis[2-hydroxy-3-(4-hydroxybenzyl)-5-methylphenyl]methane, bis[2-hydroxy-3-(4-hydroxy-2-methylbenzyl)-5-methylphenyl]methane, bis[2-hydroxy-3-(2,4-dihydroxybenzyl)-5-methylphenyl]methane, bis[4-hydroxy-5-(4-hydroxybenzyl)-2,3-dimethylphenyl]methane, bis[4-hydroxy-5-(2-hydroxy-5-methylbenzyl)-2,3-dimethylphenyl]methane, bis[4-hydroxy-5-(4-hydroxy-2-methylbenzyl)-2,3-dimethylphenyl]methane, bis[4-hydroxy-5-(2,4-dihydroxybenzyl)-2,3-dimethylphenyl]methane, bis[4-hydroxy-3-(4-hydroxybenzyl)-2,5-dimethylphenyl]methane, bis[4-hydroxy-3-(4-hydroxy-3-methylbenzyl)-2,5-dimethylphenyl]methane, bis[4-hydroxy-3-(4-hydroxy-2-methylbenzyl)-2,5-dimethylphenyl]methane, bis[4-hydroxy-3-(2,4-dihydroxybenzyl)-2,5-dimethylphenyl]methane, 2,2-bis[4-hydroxy-3-(4-hydroxybenzyl)-5-methylphenyl]propane, 2,2-bis[4-hydroxy-3-(4-hydroxy-2-methylbenzyl)-5-methylphenyl]propane, 2,2-bis[4-hydroxy-3-(2-hydroxy-5-methylbenzyl)-5-methylphenyl]propane, 2,2-bis[4-hydroxy-3-(4-hydroxy-3,5-dimethylbenzyl)-5-methylphenyl]propane; 1,1-bis[4-hydroxy-3-(4-hydroxybenzyl)-5-methylphenyl]cyclohexane, 1,1-bis[4-hydroxy-3-(2-hydroxy-5-methylbenzyl)-5-methylphenyl]cyclohexane; bis[4-hydroxy-3-(4-hydroxybenzyl)-5-methylphenyl]sulfone; 2,2-bis[3-cyclohexyl-4-hydroxy-5-(4-hydroxybenzyl)phenyl] propane, 2,2-bis[3-cyclohexyl-4-hydroxy-5-(4-hydroxy-3-methylbenzyl)phenyl]propane, and 2,2-bis[3-cyclohexyl-4-hydroxy-5-(2-hydroxy-5-methylbenzyl)phenyl]propane;

(iii) a linear pentakisphenol:

a pentakisphenol in which phenol units are bonded or connected through the connecting groups $J_{2a}$ and $J_{2b}$, and a ring may be substituted by at least one kind of substituents selected from a halogen atom, an alkyl group, a cycloalkyl group and an alkoxy group, for example, a bis[hydroxy-(hydroxybenzyl)-benzyl]-phenol such as 2,6-bis[4-hydroxy-3-(4-hydroxybenzyl)-2,5-dimethylbenzyl]-4-methylphenol, 2,6-bis[4-hydroxy-3-(4-hydroxy-3-methylbenzyl)-2,5-dimethylbenzyl]-4-methylphenol, 2,6-bis[4-hydroxy-3-(2-hydroxy-5-methylbenzyl)-2,5-dimethylbenzyl]-4-methylphenol, 2,6-bis[4-hydroxy-3-(2,4-dihydroxybenzyl)-2,5-dimethylbenzyl]-4-methylphenol, 2,6-bis[4-hydroxy-3-(4-hydroxybenzyl)-5-methylbenzyl]-4-methylphenol, 2,6-bis[4-hydroxy-3-(4-hydroxy-3-methylbenzyl)-5-methylbenzyl]-4-methylphenol, 2,6-bis[4-hydroxy-3-(2-hydroxy-5-methylbenzyl)-5-methylbenzyl]-4-methylphenol, 2,6-bis[4-hydroxy-3-(2,4-dihydroxybenzyl)-5-methylbenzyl]-4-methylphenol, 2,6-bis[2-hydroxy-3-(4-hydroxybenzyl)-5-methylbenzyl]-4-methylphenol, 2,6-bis[2-hydroxy-3-(4-hydroxy-3-methylbenzyl)-5-methylbenzyl]-4-methylphenol, 2,6-bis[2-hydroxy-3-(2-hydroxy-5-methylbenzyl)-5-methylbenzyl]-4-methylphenol, and 2,6-bis[2-hydroxy-3-(2,4-dihydroxybenzyl)-5-methylbenzyl]-4-methylphenol;

(iv) a linear polykisphenol:

a polyphenol in which phenol units are bonded or connected through the connecting groups $J_{2a}$ and $J_{2b}$, and a ring may be substituted by at least one kind of substituents selected from a halogen atom, an alkyl group, a cycloalkyl group and an alkoxy group, for example, a bis{[hydroxy-(hydroxybenzyl)-benzyl]-hydroxyphenyl}alkane such as bis{3-[4-hydroxy-3-(4-hydroxy-5-methylbenzyl)-5-methylbenzyl]-4-hydroxy-5-methylphenyl}methane and 2,6-bis{3-[2-hydroxy-3-(2-hydroxy-5-methylbenzyl)-5-methylbenzyl]-2-hydroxy-5-methylphenyl}-4-methylphenol;

(v) a branched hexakisphenol:

a bis[hydroxy-bis(hydroxyaryl)aryl]alkane such as bis[4-hydroxy-3-bis(4-hydroxy-3-methylphenyl)methylphenyl]methane, bis[4-hydroxy-3-bis(2-hydroxy-5-methylphenyl)methylphenyl]methane, bis[4-hydroxy-3-bis(4-hydroxy-2,5-dimethylphenyl)methylphenyl]methane and bis[4-hydroxy-3-bis(4-hydroxy-3,5-dimethylphenyl)methylphenyl]methane; and (vi) a tetrakisphenol from a trimethylolphenol:

a tris(hydroxybenzyl)phenol, for example, 2,4,6-tris(4-hydroxybenzyl)phenol, 2,4,6-tris(4-hydroxy-3-methylbenzyl)phenol, 2,4,6-tris(4-hydroxy-2-methylbenzyl)phenol, 2,4,6-tris(2-hydroxy-5-methylbenzyl)phenol, 2,4,6-tris(4-hydroxy-2,5-dimethylbenzyl)phenol, 2,4,6-tris(4-hydroxy-3,5-dimethylbenzyl)phenol, 2,4,6-tris(3-tert-butyl-4-hydroxybenzyl)phenol and 2,4,6-tris(3-tert-butyl-4-hydroxy-3-methylbenzyl)phenol.

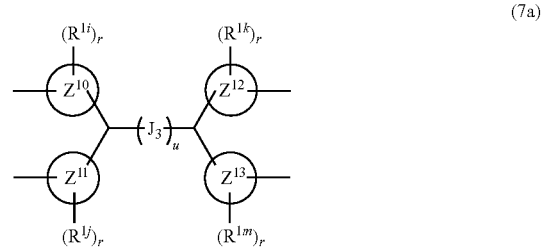

(7a)

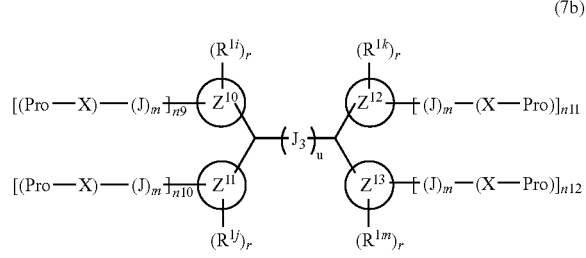

(7b)

In the formulae (7a) and (7b), $Z^{10}$ to $Z^{13}$ are the same or different, each representing a hydrocarbon ring or a heterocycle; $J_3$ represents a connecting group; $R^{1i}$, $R^{1j}$, $R^{1k}$ and $R^{1m}$ are the same or different, each representing a halogen atom, an alkyl group, an alkoxy group, an alkoxycarbonyl group, a cycloalkyl group, an aryl group, an aralkyl group or a silicon-containing group; each of the factors, n9, n10, n11 and n12, represents 0 or an integer of not less than 1, and n9+n10+n11+n12≧1; and u, r, J, m, X and Pro have the same meanings defined above.

As the rings $Z^{10}$ to $Z^{13}$, there may be exemplified a hydrocarbon ring or heterocycle in-line with the ring $Z^1$ in the formula (3a) (especially a $C_{4-8}$cycloalkane such as cyclohexane ring and a $C_{6-10}$arene ring such as benzene ring). As the substituents $R^{1i}$, $R^{1j}$, $R^{1k}$ and $R^{1m}$, a substituent in-line with the $R^1$ may be exemplified. r is the same as the formula (3a). The connecting group $J_3$ may be exemplified as a connecting group in-line with the connecting group $A^3$ in the formula (4a), the connecting group $J_1$, or the connecting groups $J_{1a}$ and $J_{1b}$, for example, a linear- or branched alkylene group (e.g., a $C_{1-6}$alkylene group), an alkenylene group (e.g., a $C_{2-4}$alkenylene group), a cycloalkylene group (e.g., a $C_{4-8}$cycloalkylene group such as cyclohexylene group), an arylene group (a $C_{6-10}$arylene group such as phenylene and naphthylene groups). m is 0 or 1.

In the compound represented by the formula (7b), summation of n9, n10, n11 and n12 is about 4 to 12 (e.g., about 4 to 10), preferably about 4 to 8 (e.g., about 4 to 6).

As the compound corresponding to the formula (7a) the following compounds may be exemplified;

(a) a radial tetrakisphenol:

a tetrakis(hydroxyphenyl)alkane, for example, 1,1,2,2-tetrakis(4-hydroxyphenyl)ethane, a radial tetrakisphenol having at least one substituent selected from an alkyl group, an alkoxy group and a halogen atom [e.g., 1,1,2,2-tetrakis(4-hydroxy-3-methylphenyl)ethane, 1,1,2,2-tetrakis(4-hydroxy-2,5-dimethylphenyl)ethane, 1,1,2,2-tetrakis(4-hydroxy-3,5-dimethylphenyl)ethane, 1,1,2,2-tetrakis(5-t-butyl-4-hydroxy-2-methylphenyl)ethane, 1,1,5,5-tetrakis(4-hydroxyphenyl)pentane, 1,1,5,5-tetrakis(4-hydroxy-3-methylphenyl)pentane and the like; a bis[bis (hydroxyphenyl)methyl]benzene, for example, 1,4-bis[1,1-bis(4-hydroxyphenyl)methyl]benzene, 1,4-bis[1,1-bis(4-hydroxy-3-methylphenyl)methyl] benzene, 1,4-bis[1,1-bis(2-hydroxy-5-methylphenyl) methyl]benzene, 1,4-bis[1,1-bis(4-hydroxy-2,5-dimethylphenyl)methyl]benzene, 1,4-bis[1,1-bis(4-hydroxy-3,5-dimethylphenyl)methyl]benzene, 1,4-bis[1,1-bis(4,5-dihydroxy-2-dimethylphenyl) methyl]benzene, and 1,4-bis[1,1-bis(4-hydroxyphenyl)ethyl]benzene];

(b) a radial phenol composed of different kinds of phenols:
4-[1,1-bis(4-hydroxyphenyl)methyl]-4'-[1,1-bis(4-hydroxy-2,5-dimethylphenyl)methyl]benzene, 4-[1,1-bis(4-hydroxy-3,5-dimethylphenyl)methyl]-4'-[1,1-bis(4-hydroxy-2,5-dimethylphenyl)methyl]benzene, 4-[1,1-bis(4-hydroxyphenyl)methyl]-4'-[1,1-bis(4-hydroxy-3,5-dimethylphenyl)methyl]benzene, 4-[1,1-bis(4-hydroxy-3-methylphenyl)methyl]-4'-[1,1-bis(4-hydroxy-3,5-dimethylphenyl)methyl]benzene, 4-[1,1-bis(2,4-dihydroxyphenyl)methyl]-4'-[1,1-bis (4-hydroxy-3,5-dimethylphenyl)methyl]benzene, 4-[1,1-bis(4-hydroxy-3,5-dimethylphenyl)methyl]-4'-[1,1-bis(4,5-dihydroxy-2-methylphenyl)methyl] benzene, 1,1-bis(4-hydroxy-2,5-dimethylphenyl)-2, 2-bis(2,3,4-trihydroxyphenyl)ethane and the like.

formula (3a) (especially a $C_{4-8}$ cycloalkane ring such as cyclohexane ring, a $C_{6-10}$ arene ring such as benzene ring) As the substituents $R^{1n}$, $R^{1p}$, $R^{1q}$ and $R^{1r}$, there may be exemplified the same substituents as the $R^1$. r is the same as the formula (3a) concerning each of the rings, $Z^{14}$ to $Z^{19}$. The connecting groups $R^2$ and $R^3$ may be exemplified as the connecting group $A^3$ in the formula (4a), or the same connecting groups as the connecting group $J_1$, for example, may be a linear- or branched alkylene group (e.g., a $C_{1-6}$ alkylene group), an alkenylene group (e.g., a $C_{2-4}$ alkenylene group).

In the compounds represented by the formula (8b), the summation of n13, n14, n15, n16, n17 and n18 is about 4 to 10 (e.g., about 4 to 8), preferably about 4 to 7 (e.g., about 4 to 6). Incidentally, each of the factors, n14 and n17, may be 0.

As the compounds corresponding to the formula (8a) there may be exemplified a radial hexakisphenol (a bis[hydroxy-bis(hydroxybenzyl)phenyl]alkane), for example, 2,2-bis[4-hydroxy-3,5-bis(4-hydroxybenzyl)phenyl]propane, a radial hexakisphenol having at least one kind of substituents selected from an alkyl group, a cycloalkyl group and a halogen atom, [e.g., 2,2-bis[4-hydroxy-3,5-bis(4-hydroxy-3-methylbenzyl)phenyl]propane, 2,2-bis[4-hydroxy-3,5-bis(4-hydroxy-2-methylbenzyl)phenyl]propane, 2,2-bis[4-hydroxy-3,5-bis(2-hydroxy-5-methylbenzyl)phenyl] propane, 2,2-bis[4-hydroxy-3,5-bis(4-hydroxy-2,5-

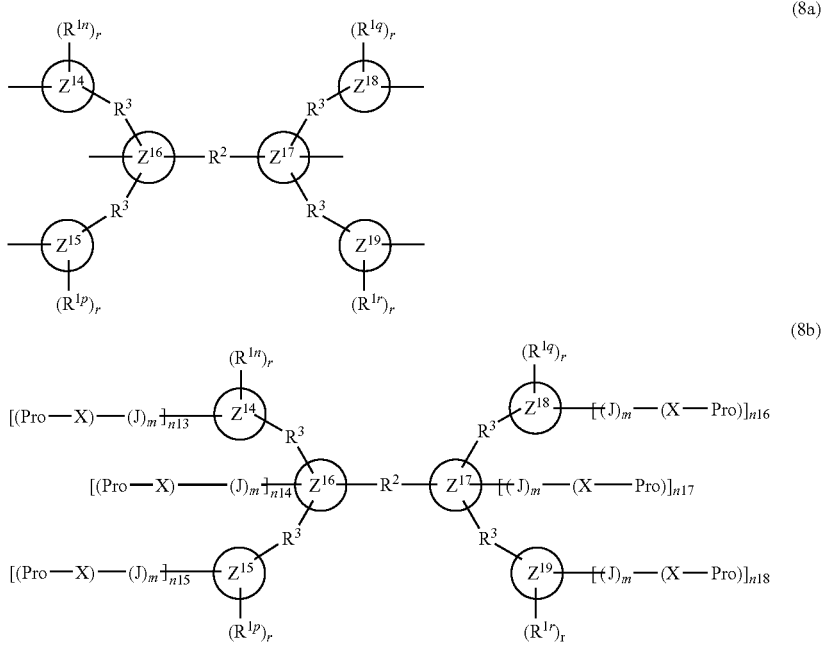

(8a)

(8b)

In the formulae (8a) and (8b), the rings $Z^{14}$ to $Z^{19}$ are the same or different, each representing a hydrocarbon ring or a heterocycle; $R^2$ and $R^3$ are the same or different, each representing a connecting group; $R^{1n}$, $R^{1p}$, $R^{1q}$ and $R^{1r}$ are the same or different, each representing a halogen atom, an alkyl group, an alkoxy group, an alkoxycarbonyl group, cycloalkyl group, an aryl group, an aralkyl group, or a silicon-containing group; each of the factors, n13, n14, n15, n16, n17 and n18, represents 0 or an integer of not less than 1, and n13+n14+n15+n16+n17+n18≧1; and r, J, m, X and Pro have the same meanings defined above.

As the rings $Z^{14}$ to $Z^{19}$, there may be exemplified the same hydrocarbon rings or heterocycles with the ring $Z^1$ in the dimethylbenzyl)phenyl]propane, 2,2-bis[4-hydroxy-3,5-bis (4-hydroxy-3,5-dimethylbenzyl)phenyl]propane].

Incidentally, in each of the hydrophobic units, represented by the formulae (4a) to (8a) and (4b) to (8b), and having a plurality of rings Z, the number r of the substituent $R^1$ may be different depending on each of the rings, $Z^2$ to $Z^{19}$. Moreover, in the formula (8a), a plurality of connecting groups are represented by the same symbol $R^3$ as a matter of convenience, but each of these connecting groups may be different.

Incidentally, for a resist application, when a photoactive compound contains the same or comparable unit with the construction unit of a photosensitive resin as the hydrophobic unit, the compatibility with the photosensitive resin can be improved.

Using such a compound, especially in the application for resist, both the affinity to a base resin of the resist, and the solubility to a developer are facilely controllable. Incidentally, in these compounds, the hydrophilic group X (e.g., a hydroxyl group and a carboxyl group) may be protected by the protective group Pro in advance, or may be protected by the protective group Pro after introduction of the hydrophilic group. The protective group Pro is removable by light exposure in association with the photosensitizer.

The weight-average molecular weight Mw of the photoactive compound is, in a polymer usually not less than 5000, in an oligomer usually about 100 to 2500, preferably about 200 to 2000, more preferably about 300 to 1,000. In the case where the photoactive compound is a monomer to an oligomer, especially in the application for resist, the solubility of resist to a solvent and the affinity of resist to a resin can be improved, and further difference of dissolution rate (between exposed area and non-exposed area) can be enlarged.

The photoactive compound can be produced by a conventional method. For example, the hydroxyl group in the compound corresponding to the hydrophobic unit A in the formula (1) or the formula (3a), can be easily protected by a reaction with a protectant (protecting agent) (e.g., a dialkyl dicarbonate (e.g., di-t-butyl dicarbonate), and 2-t-butoxycarbonyloxyimino-2-phenylacetonitrile (Boc-ON)), an addition reaction with an olefin (e.g., isobutylene) or an alkyl vinyl ether (e.g., ethyl vinyl ether), and an esterification reaction with a carboxylic acid (e.g., isobutylic acid). The carboxyl group in the compound corresponding to the hydrophobic unit A in the formula (1) or the formula (3a), can be easily protected by a method where the carboxyl group, or an acylhalide group formed by thionyl chloride if necessary, is esterified with an alcohol (e.g., t-butanol) corresponding to the protective group. Further, the carboxyl group protected by the protective group can be easily introduced by a coupling reaction (e.g., Hech reaction) of a halogen-containing compound corresponding to the hydrophobic unit A in the formula (1) or the formula (3a) (especially an aromatic compound having a bromine or iodine atom) with an ester of a carboxylic acid (especially a $C_{1-4}$alkyl ester of an acrylic acid). Incidentally, in the case using an unsaturated compound in the coupling reaction, the unsaturated bond introduced into a halogen-containing compound corresponding to the hydrophobic unit A in the formula (1) or the formula (3a) may be hydrogenated after using the unsaturated compound.

Incidentally, a photoactive compound in which a plurality of rings Z are bonded or connected through the connecting group A and/or J may be produced (a) by protecting a hydrophilic group with the same reaction described above by using a hydrophobic compound having a hydrophilic group, in which a plurality of rings Z are bonded or connected through the connecting group A and/or J, or (b) by reacting a hydrophobic component having a first ring Z, in which a protective group for a hydrophilic group is introduced, with a hydrophobic component having a second ring Z. Further, in the case where these photoactive compounds have a hydrophilic group or a reactive atom (e.g., a halogen atom such as a bromine atom and an iodine atom), with the use of the above-mentioned reaction, a hydrophilic group may be protected or a protective group may be introduced. Incidentally, in a reaction of a hydrophobic component having a first ring Z with a hydrophobic component having a second ring Z, there may be utilized a variety of methods where the connecting group A or J can be formed, for example, addition reaction, esterification reaction, condensation reaction, amide forming reaction and coupling reaction.

The usage of such a photoactive compound is not especially restricted, and in particular, such a photoactive compound is preferably used for a resist. That is, although the photoactive compound is hydrophobic (or capable of hydrophobicity by the interaction with an alkali), the photoactive compound is capable of hydrophilicity in the case where the protective group is removed (or deprotected) by light exposure (especially, in association with a photosensitizer owing to light exposure) to cause (make) a hydrophilic group by using the active component in combination with a photosensitizer (e.g., a photo acid generator). Consequently, when the photoactive compound is applied to a resist(especially, a positive resist) and the like, dissolution of a resist layer is accelerated by formation of a hydrophilic domain in the exposed area, and dissolution can be restrained by enhancing an affinity to a base resin by an action of the protective group in a non-exposed area, resulting in enlarging the difference in dissolution rate between the exposed area and the non-exposed area. In particular, by using a hydrophobic group as the protective group, drastic restraint of solubility in the non-exposed area as well as restraint of swelling of a resist with development can be realized, resulting in improvement of resolution. The removal (elimination) of the protective group mostly occurred in association with (in relation to) the photosensitizer, especially by a catalytic action of an acid. As such an acid, an acid generated by light exposure (especially an acid generated from a photo acid generator constituting a photosensitive resin composition) is advantageously utilized.

As the photosensitizer combined with a photoactive compound, a conventional photosensitizer or photo-sensitizer used in a positive resist may be selected from, for example, a diazonium salt (e.g., a diazonium salt, a tetrazonium salt, a polyazonium salt), a quinonediazide (e.g., a diazobenzoquinone derivative and a diazonaphthoquinone derivative), a photo acid generator and a dissolution inhibitor.

As the photo acid generator (photoactive acid generator), there may be exemplified the following compounds. Incidentally, trade names produced by Midori Kagaku Co. Ltd. are written within parentheses for reference. As the photo acid generator, there may be exemplified a derivative of sulfonium salt [e.g., a sulfonic acid ester (an arylalkane sulfonate (particularly, a $C_{6-10}$aryl$C_{1-2}$alkane sulfonate) such as 1,2,3-tri(methylsulfonyloxy)benzene); an arylbenzene phosphonate (particularly, a $C_{6-10}$aryltoluene phosphonate which may have a benzoyl group) such as 2,6-dinitrobenzyltoluene sulfonate and a benzoin tosylate; an aralkylbenzene sulfonate (particularly, a $C_{6-10}$aryl-$C_{1-4}$alkyltoluene sulfonate which may have a benzoyl group) such as 2-benzoyl-2-hydroxy-2-phenylethyltoluene sulfonate; a disulfone such as a diphenylsulfone; a Lewis acid salt (e.g., a triarylsulfonium salt (particularly, a triphenylsulfonium salt) such as a triphenylsulfonium hexafluorophosphate (TPS-102), a triphenylsulfonium hexafluoroantimony (TPS-103), 4-(phenylthio)phenyldiphenylsulfonium hexafluoroantimony (DTS-103), 4-methoxyphenyldiphenylsulfonium hexafluoroantimony (MDS-103), a triphenylsulfonium methanesulfonyl, a triphenylsulfonium trifluoromethanesulfonyl (TPS-105) and a triphenylsulfonium nonafluorobutanesulfonyl (TPS-109), etc.], a derivative of phosphonium salt; a derivative of diarylhalonium salt [e.g., a Lewis acid salt such as a diaryliodonium salt (e.g., diphenyliodonium hexafluorophosphate, 4,4'-di(t-butylphenyl)iodonium hexafluorophosphate (BBI-102), 4,4'-di(t-butylphenyl)iodonium hexafluoroantimonate (BBI-103), 4,4'-di(t-butylphenyl)iodonium tetrafluoroborate (BBI-101), 4,4'-di(t-butylphenyl)iodonium trifluoromethanesulfonate (BBI-105), 4,4'-di(t-butylphenyl)iodonium camphorsulfonate (BBI-106), diphenyliodonium trifluoromethanesulfonate (DPI-105), 4-methoxyphenyl phenyliodonium trifluoromethanesulfonate (DPI-105))], a derivative of a diazonium salt (a Lewis acid salt such as p-nitrophenyldiazonium hexafluorophosphate), a diazomethane derivative, a triazine derivative [e.g., a haloalkyltriazinylaryl such as 1-methoxy-4-(3,5-di(trichloromethyl) triazinyl)benzene (TAZ-104) and 1-methoxy-4-(3,5-di (trichloromethyl)triazinyl)naphthalene (TAZ-106), a haloalkyltriazinylalkenylaryl such as 1-methoxy-4-[2-(3,5-ditrichloromethyltriazinyl)ethenyl]benzene (TAZ-110), 1,2-dimethoxy-4-[2-(3,5-ditrichloromethyltriazinyl)ethenyl] benzene (TAZ-113) and 1-methoxy-2-[2-(3,5-ditrichloromethyltriazinyl)ethenyl]benzene (TAZ-118)], an imidylsulfonate derivative[a succinimidyl camphorsulfonate (SI-106), succinimidyl phenylsulfonate (SI-100), succinimidyl toluylsulfonate (SI-101), succinimidyl trifluoromethylsulfonate (SI-105), phthalimidyl trifluorosulfonate (PI-105), naphthalimidyl camphorsulfonate (NAI-106), naphthalimidyl methanesulfonate (NAI-100), naphthalimidyl trifluoromethanesulfonate (NAI-105), naphthalimidyl toluylsulfonate (NAI-101), norborneneimidyl trifluoromethanesulfonate (NDI-105), etc.], and the like. Moreover, sulfone derivatives are also included, for example, a compound having a unit —$SO_2$—C(=N)— such as trade name "DAM-101", "DAM-102", "DAM-105" and "DAM-201"; a compound having a unit —$CH_2$—$SO_2$— such as "DSM-301"; a compound having a unit =N—O—$SO_2$— such as "PAI-101". In Particular, Lewis acid salts (e.g., Lewis acid salts such as phosphonium salts) are preferred.

In particular, a photosensitive resin composition in which the photo acid generator (photoactive acid generator), the photoactive compound (which is deprotected by the acid produced from the acid generator owing to (by) light exposure to produce a hydrophilic group), and a base resin (a base resin which can be alkali-soluble by removing a protective group owing to the acid) are combined is advantageously used as a positive chemical-amplifying resist.

[Photosensitive Resin Composition]

In the present invention, a photosensitive resin composition (or a resist composition) may be composed of the photoactive compound, the photosensitizer, and a base resin (an oligomer or a polymer). The photosensitive resin composition can be developed by an organic solvent (e.g., an alcohol), and usually the photosensitive resin is preferred to be developable with water or an alkaline developer (be capable of water- or alkali-development).

(Base Resin)

As the base resin, there may be exemplified, for example, a hydroxyl group-containing polymer [e.g., a polyvinyl acetal, a polyvinyl alcohol, an ethylene-vinylalcohol copolymer, a hydroxyl group-containing cellulose derivative (e.g., a hydroxyethyl cellulose), a polyvinyl phenolic resin and a novolak resin (e.g., a phenol novolak resin)], a carboxyl group-containing polymer [e.g., a homo- or copolymer comprising a polymerizable unsaturated carboxylic acid (e.g., a (meth)acrylic acid, maleic anhydride and itaconic acid) and a carboxyl group-containing cellulose derivative (e.g., a carboxyl methylcellulose or its salt)], an ester group-containing polymer [e.g., a homo- or copolymer of a monomer such as a vinylester of carboxylic acid (e.g., a vinyl acetate) and an ester of(meth)acrylic acid (e.g., a methyl methacrylate) (e.g., a polyvinyl acetate, an ethylene-vinyl acetate copolymer and a (meth)acrylic resin) and a polyester, a cellulose ester, etc.], a ether group-containing polymer [e.g., a polyalkylene oxide, a polyoxyalkylene glycol, a polyvinyl ether-series resin, a silicon-containing resin, a cellulose ether, etc.], a carbonate group-containing polymer, an amide or N-substituted amide group-containing polymer [e.g., a polyvinyl pyrrolidone, a polyurethane-series polymer, a polyurea, a nylon or a polyamide-series polymer [e.g., a polyamide using a lactam component, a dicarboxylic acid component or a diamine component); a poly(meth)acrylamide-series polymer; a polyamino acid; a polymer having a biuret bond; a polymer having an allophanate bond; and a protein such as gelatin], a polymer having a nitrile group (e.g., an acrylonitrile-series polymer), a polymer having a glycidyl group (an epoxy resin, a homo- or copolymer of glycidyl (meth)acrylate, etc.), a halogen-containing polymer (e.g., a polyvinyl chloride, a vinyl chloride-vinyl acetate copolymer, a vinylidene chloride-series polymer and a chlorinated polypropylene), a polymer having a nonaromatic ring group (e.g., a polymer comprising a monomer having a $C_{5-8}$cycloalkyl group such as cyclohexyl (meth) acrylate a polymer comprising a monomer having a crosslinked cyclic $C_{7-20}$hydrocarbon ring group such as norbornyl (meth)acrylate and adamantyl (meth)acrylate), and a polymerizable oligomer or polymer (e.g., an oligomer or polymer having a polymerizable group such as a (meth)acryloyl group, an allyl group, a vinyl group and a cinnamoyl group). The base resin may be utilized either singly or in combination of two or more species. The base resin may be a base resin for constituting a negative photosensitive resin composition, and preferably a base resin for constituting a positive photosensitive resin composition (positive resist).

The typical base resin constituting a positive resist includes a novolak resin (e.g., a phenol novolak resin and a cresol novolak resin), a resin in which a hydrophilic group (e.g., a hydroxyl group and/or a carboxyl group) is protected by a removable protective group. The base resin can be used singly or in combination.

As the novolak resin, an alkali-soluble novolak resin is usually employed, and in the case utilizing a resist for semiconductor production, a conventional novolak resin used in the field (realm) of a resist can be employed. The novolak resin is obtainable by condensation of a phenol having at least one phenolic hydroxyl group with an aldehyde in the presence of an acid catalyst. As the phenol, there may be mentioned, for example, phenol, a $C_{1-4}$alkylphenol such as o-, m- or p-cresol, 2,5-, 3,5- or 3,4-xylenol, 2,3,5-trimethylphenol, ethylphenol, propylphenol, butylphenol and 2-t-butyl-5-methylphenol, a dihydroxybenzene, and a naphthol. The aldehyde includes an aliphatic aldehyde such as formaldehyde, acetaldehyde, and glyoxal, an aromatic aldehyde such as benzaldehyde and salicylaldehyde, and the like.

The phenols can be used singly or in combination and the aldehydes can be used singly or in combination. As the acid catalyst, there may be mentioned an inorganic acid (e.g., hydrochloric acid, sulfuric acid, and phosphoric acid), an organic acid (e.g., oxalic acid, acetic acid, and p-toluenesulfonic acid), an organic acid salt (e.g., a bivalent metal salt such as zinc acetate) and the like. The condensation reaction can be conducted with a conventional method, for example, for about 2 to 30 hours around the temperature of about 60 to 120° C. The reaction may be conducted in a bulk or in an appropriate solvent.

The base resin preferably comprises a resin capable of producing a hydrophilic group by an action of an acid. Such a base resin may comprise a homo- or copolymer of a monomer having a hydrophilic group (especially a hydrophilic group selected from a hydroxyl group and a carboxyl group) capable of being protected by a protective group which is removable (capable of removing) by an action of an acid. As the resin in which the hydrophilic group(s) (e.g., a hydroxyl group and/or a carboxyl group) is(are) protected (or protectable, capable of being protected) by a removable protective group, there may be exemplified, for example, a polyvinylphenolic resin in which a phenolic hydroxyl group is protected by a removable protective group (e.g., a homopolymer of vinyl phenol, or a copolymer of vinyl phenol and a copolymerizable monomer), a hydroxyl group- and/or carboxyl group-containing (meth)acrylic resin [e.g., a homo- or copolymer of (meth)acrylate, or a copolymer of (meth)acrylate and a copolymerizable monomer], and a hydroxyl group- and/or carboxyl group-containing norbornene-series resin (e.g., a copolymer of a norbornene derivative containing a hydroxyl group and/or a carboxyl group and a copolymerizable monomer). When a resin which has high transparency (transparent properties) to an exposing wavelength (e.g., a nonaromatic resin such as a (meth)acrylic resin and a norbornene-series resin) is used as the base resin, enhancement of sensitivity can be ensured even to exposure beams of a shorter wavelength. Moreover, when a nonaromatic photosensitive resin composition is used, utilization of exposure sources of short wavelength can be achieved, and further formation (or constitution) of minuter patterns can be realized.

Incidentally, the resin in which a hydrophilic group is protected by a removable protective group may be obtained by polymerizing a monomer in which a hydrophilic group is protected by a protective group (e.g., the protective group exemplified in the section of the photoactive compound) in advance, or may be obtained by polymerizing a monomer having a hydrophilic group and protecting the hydrophilic group of the obtained resin by the protective group.

Among the monomers having a hydrophilic group, as the monomer having a hydroxyl group, there may be mentioned a vinylphenolic monomer (e.g., vinylphenol); an allyl alcohol; a hydroxyalkyl (meth)acrylate (a hydroxyC$_{2-6}$alkyl (meth)acrylate such as hydroxyethyl (meth)acrylate, hydroxypropyl (meth)acrylate, and 2-hydroxybutyl (meth)acrylate); a (poly)oxyalkylene glycol mono(meth)acrylate such as diethylene glycol mono(meth)acrylate; a (meth)acrylate having a monocyclic alicyclic group, such as a hydroxycycloalkyl (meth)acrylate (a hydroxyC$_{3-8}$cycloalkyl (meth)acrylate such as hydroxycyclohexyl (meth)acrylate) and a hydroxyoxacycloalkyl (meth)acrylate; a (meth)acrylate having a crosslinked cyclic alicyclic group, such as a hydroxydecalinyl (meth)acrylate, hydroxybornyl (meth)acrylate, hydroxynorbornyl (meth)acrylate, and hydroxyadamantyl (meth)acrylate (e.g., a hydroxybi- to tetraC$_{3-8}$cycloalkyl (meth)acrylate); and a norbornene derivative having a hydroxyl group, such as hydroxynorbornene, a hydroxyalkyl-norbornene (e.g., a hydroxyC$_{1-4}$alkyl-norbornene such as hydroxymethyl-norbornene and hydroxyethyl-norbornene). As the monomer having a carboxyl group, there may be mentioned an unsaturated carboxylic acid such as a (meth)acrylic acid, maleic acid, fumaric acid, and a vinylbenzoic acid; a carboxyC$_{5-8}$cycloalkyl (meth)acrylate such as carboxycyclohexyl (meth)acrylate; a (meth)acrylate having a carboxyl group-containing crosslinked cyclic alicyclic hydrocarbon group (e.g., a carboxybi- to tetraC$_{3-8}$cycloalkyl (meth)acrylate such as carboxydecalinyl (meth)acrylate, carboxynorbornyl (meth)acrylate, carboxymethyl-norbornyl (meth)acrylate, carboxybornyl (meth)acrylate, and carboxyadamantyl (meth)acrylate), and the like. These monomers having the hydrophilic group can be used singly or in combination.

As the copolymerizable monomer, a conventional copolymerizable monomer may be mentioned, for example, a (meth)acrylic monomer [e.g., an alkyl (meth)acrylate (a C$_{1-10}$alkyl (meth)acrylate) such as methyl (meth)acrylate, ethyl (meth)acrylate, and butyl (meth)acrylate; a cycloalkyl (meth)acrylate (a cycloC$_{3-8}$alkyl (meth)acrylate) such as cyclohexyl (meth)acrylate; a (meth)acrylate having a monocyclic heterocycle group, such as oxacycloalkyl (meth)acrylate; a (meth)acrylate having a crosslinked cyclic alicyclic group (a bi- to tetracycloC$_{3-8}$alkyl (meth)acrylate), such as a decalinyl (meth)acrylate, norbornyl (meth)acrylate, bornyl (meth)acrylate, and adamantyl (meth)acrylate; a hydroxyC$_{2-6}$alkyl (meth)acrylate such as hydroxyethyl (meth)acrylate; an epoxy group-containing (meth)acrylate such as glycidyl (meth)acrylate; a (meth)acrylonitrile]; an imide-series monomer [e.g., an N—C$_{1-4}$alkylmaleimide such as maleimide, N-methylmaleimide, and N-ethylmaleimide, an N—C$_{6-10}$arylmaleimide such as N-phenylmaleimide]; an unsaturated carboxylic acid [e.g., crotonic acid, maleic anhydride and itaconic acid], an aromatic vinyl-series monomer (a styrenic monomer) such as styrene, α-methylstyrene, p-t-butylstyrene, and vinyltoluene; a vinyl ether-series monomer such as vinyl methyl ether and vinyl ethyl ether; a fatty acid vinyl ester-series monomer such as vinyl acetate and vinyl propionate.

These copolymerizable monomers can be used singly or in combination. In the copolymer with a copolymerizable monomer, the proportion of the monomer having a hydrophilic group is, relative to the total amount of monomers, about 10 to 100% by weight, preferably about 25 to 80% by weight, and more preferably about 30 to 70% by weight.

In the resin forming a hydrophilic group by deprotection, as a protective group for the hydrophilic group, there may be mentioned the protective groups exemplified in the section of the photoactive compound, for example, a protective group for a hydroxyl group such as an alkoxyalkyl group, an alkoxycarbonyl group, a cycloalkyl group, an oxacycloalkyl group and a crosslinked alicyclic group and an alkylsilyl group; and a protective group for a carboxyl group such as an alkyl group.

The typical resin includes, for example, a polyalicyclic alcoholic resin (e.g., a homo- or copolymer of a hydroxyl group-containing alicyclic (meth)acrylate such as a hydroxycycloalkyl (meth)acrylate) in which a hydroxyl group is protected by a protective group such as an alkoxyalkyl group and an alkoxycarbonyl group (t-BOC group, etc.), a (meth)acrylic resin (e.g., a homo- or copolymer of a hydroxyalkyl (meth)acrylate) in which a hydroxyl group is protected by an alicyclic group such as a cycloalkyl group (including an oxacycloalkyl group; and a bi- or tricycloalkyl group such as norbornyl group and adamantyl group), a (meth)acrylic resin (e.g., a homo- or copolymer of a (meth)acrylic acid) in which a carboxyl group is protected by a protective group such as an alkyl group (e.g., t-butyl group).

The weight-average molecular weight of the base resin is about 6000 to 50000, preferably about 7000 to 30000, and more preferably about 7000 to 20000.

The preferable positive resist includes a combination of a resin forming a hydrophilic group by a deprotection (especially deprotection by catalytic action of an acid produced from an acid generator) and a photosensitizer (photo acid generator).

(Proportion of each Component)

The weight ratio of the photoactive compound relative to the photosensitizer can be selected within the wide range of about 0.01/1 to 100/1 (the former/the latter), and usually about 0.1/1 to 75/1, and preferably about 1/1 to 50/1.

In the positive photosensitive resin composition (positive resist), the amount of the photosensitizer relative to 100 parts by weight of a base resin can be selected within the range of about 0.1 to 50 parts by weight, preferably about 1 to 30 parts by weight, and more preferably about 1 to 20 parts by weight (especially about 1 to 10 parts by weight).

Moreover, in the photosensitive resin composition, the amount of the photoactive compound is, relative to the total solid content of a resist, not more than 50% by weight (e.g., about 1 to 50% by weight), preferably about 3 to 40% by weight, and more preferably about 5 to 30% by weight. Moreover, the amount of the photoactive compound is about 1 to 1000 parts by weight (e.g., about 5 to 1000 parts by weight), preferably about 10 to 500 parts by weight and more preferably about 10 to 300 parts by weight, especially about 10 to 100 parts by weight, on a solid matter basis, relative to 100 parts by weight of the base resin.

To the photosensitive resin composition, various additives may be added, for example, a stabilizer such as an antioxidant, a plasticizer, a surfactant, a dissolution accelerator, and a coloring agent (e.g., dyes, pigments), if necessary. Further, in order to improve handling properties such as coating, the photosensitive resin composition may comprise a solvent [for example, a hydrocarbon, a halogenated hydrocarbon, an alcohol (e.g., methanol, ethanol and isopropanol), a ketone (e.g., acetone and cyclohexanone), an ester (e.g., ethyl acetate and ethyl lactate), an ether, a cellosolve (e.g., a methylcellosolve, a ethylcellosolve and a butylcellosolve), a carbitol, a glycol ether ester (e.g., a (poly)oxyalkylene glycol alkyl ether acetate such as cellosolve acetate and propylene glycol monomethyl ether acetate (e.g., PGMEA)].

The photosensitive resin composition can be prepared in accordance with a conventional method, for example, by mixing a photosensitive resin [a photosensitive resin composition comprising a base resin (a polymer or an oligomer) and a photosensitizer] and a photoactive compound. The photosensitive resin composition usually contains a solvent [e.g., an ester of lactic acid such as ethyl lactate; a (poly)oxyalkylene glycol alkyl ether acetate such as propylene glycol methyl ether acetate (e.g., PGMEA)]. The amount of the solvent to be used is not especially limited, for example, is about 0.1 to 50 parts by weight, preferably about 1 to 40 parts by weight, and more preferably about 5 to 30 parts by weight, relative to 1 part by weight of the photosensitive resin.

[Photosensitive Layer]

The photosensitive layer can be formed by applying (spreading or coating) the above-described photosensitive resin composition to a substrate (a base material). According to the intended pattern and use, the substrate (base material) can be suitably selected from metals (aluminum), glass, ceramics (e.g., alumina, copper doped alumina and tungsten silicate), plastics and others, and the substrate may be a semiconductor substrate such as silicon wafer.

The surface of the substrate may be previously treated to improve the adhesion with the photosensitive layer, depending on its intended use. The surface treatment includes a surface treatment using the silane coupling agent described above (e.g., a hydrolytic polymerizable silane coupling agent having a polymerizable group) or others, a coating treatment with an anchor coating agent or a base coat agent (e.g., a polyvinyl acetal, an acrylic resin, a vinyl acetate-series resin, an epoxy resin, a urethane resin), or with a mixture of such a base coat agent with an inorganic fine particles (particles finely divided), and others.

Incidentally, after applying the photosensitive resin composition to the substrate, solvents may be evaporated by drying. For example, removal of solvents may be conducted by soft-baking (pre-baking) with the use of a heating means such as a hot plate.

The photosensitive layer with the photosensitive resin composition of the present invention may be formed at least on the surface of a resist layer. The structure of the photosensitive layer can be selected according to the process of forming patterns or the intended circuit structures, and may be a single- or multi-layered structure (or a lamination layer, a composite structure) The thickness of the photosensitive layer is not particularly restricted and, for example, can be selected within the range of about 0.01 to 10 μm, preferably about 0.05 to 5 μm, preferably about 0.08 to 2 μm, and is usually about 0.05 to 1 μm (e.g., about 0.1 to 0.7 μm).

The photosensitive layer can be formed by conventional coating methods such as spin coating method, dipping method, and casting method. If necessary, the coated composition is dried to remove the solvent thereby to form a photosensitive layer.

[Process for Forming Pattern]

Patterns (particularly, minute patterns) can be carried out by a conventional lithography technique which is a combination of exposure, development and etching.

For example, a pattern can be formed by applying or coating the photosensitive resin composition onto a substrate to form a photosensitive layer, exposing the coating layer to light, and developing the light-exposed layer to form a pattern. In particular, in the case using a chemical-amplifying photosensitive resin, heating treatment is preferably conducted after exposure (e.g., baking after exposure (post exposure bake, PEB)), to efficiently diffuse an acid generated by exposure. Moreover, after patterning by development, an etching treatment by plasma treatment (e.g., oxygen plasma) may be conducted.

The exposure to the photosensitive layer can be carried out according to a conventional method, for example, by pattern-irradiating the layer with light or pattern-exposing the layer to light, through a given mask. As the light for patternwise exposure, various beams (an active beam) are available according to photosensitive properties of a photosensitive resin composition, minuteness of a pattern, and kind of a base resin, for example, a beam of a halogen lamp, a high pressure mercury lamp and a UV lamp; a radial ray (radioactive ray) such as g-ray (436 nm), i-ray (365 nm), an excimer laser (e.g., XeCl (308 nm), KrF (248 nm), KrCl (222 nm), ArF (193 nm), ArCl (172 nm) and $F_2$ (157 nm)), electron rays (electron [electronic] beam), EB-ray, EUV-ray (13 nm), and X-ray, and the beams (rays) may be the ones of single-wavelength or complex (composite)-wavelength. In particular, a beam having a wavelength of about 10 to 300 nm such as the excimer lasers (e.g., KrF (248 nm), ArF (193 nm) and $F_2$ (157 nm)), X-ray, EB-ray and EUV-ray (13 nm) are advantageously employed.

Moreover, with the use of resists comprising a nonaromatic base resin, transparency (transparent properties) to short wavelength beams can be improved, and improvement of sensitivity can be achieved. For example, in the case of using KrF excimer laser (248 nm) as the light source for exposure, such a chemical-amplifying photosensitive resin composition is available, for example, a positive photosensitive resin composition which comprises a resin forming a hydrophilic group by deprotection [e.g., a polyvinylphenolic resin in which a hydroxyl group is protected by a protective group or a nonaromatic resin in which a hydroxyl or carboxyl group is protected by a protective group] and a photosensitizer (acid generator). As the nonaromatic resin in which a hydroxyl or carboxyl group is protected by a protective group, there may be exemplified, for example, a (meth)acrylic resin in which a carboxyl group is protected by a protective group; an alicyclic resin having a carboxyl or hydroxyl group protected by a protective group [e.g., a resin in which a carboxyl or hydroxyl group is protected by a protective group, and which is a copolymer of an alicyclic monomer (e.g., a norbornene derivative such as carboxynorbornene, hydroxynorbornene and hydroxyethylnorbornene) and a copolymerizable monomer such as a maleic anhydride].

Further, in the case using ArF excimer laser (193 nm) as a light source for exposure, for example, the nonaromatic resin in which a hydroxyl or carboxyl group is protected by a protective group is available.

Incidentally, the energy for exposure can be selected according to the photosensitive properties (e.g., solubility, etc.) of the above photosensitive resin composition, and the exposing time can be usually selected within the range of about 0.005 second to 10 minutes, and preferably about 0.01 second to 1 minute.

The temperature of heating (pre-bake and PEB) is about 50 to 150 ° C., preferably about 60 to 150 ° C., more preferably about 70 to 150° C., and heating time is about 30 seconds to 5 minutes, preferably about 1 to 2 minutes.

The high-resolution pattern can be formed by developing the photosensitive layer in a conventional manner after pattern-exposing. Various developers or developing agents (e.g., water, alkaline aqueous solutions) are usable for development, and the choice thereof depends on the type of the photosensitive resin composition. Preferred developers include water and alkaline developers. If necessary, the developer may contain a small amount of an organic solvent (e.g., a hydrophilic or water-soluble solvent such as alcohols typified by methanol, ethanol, and isopropanol, ketones typified by acetone, ethers typified by dioxanes and tetrahydrofurane, cellosolves, cellosolve acetates), a surfactant and others. There is no particular restriction on the developing method, and the paddle (meniscus) method, dipping method, spraying method and others are adaptable.

Incidentally, besides the pre-bake and PEB, in an appropriate step from application of the photosensitive resin composition to development, the coated layer (photosensitive layer) may be subjected to heat- or cure-treatment at a suitable temperature. If necessary, for example, after the development, the coated layer may be subjected to heat-treatment.

INDUSTRIAL APPLICABILITY

The photoactive compound of the present invention is capable of hydrophilicity by deprotection (of the protective group) owing to light exposure, therefore, in the case using the photoactive compound in combination with a photosensitizer (a photosensitizer and a base resin) for forming a photosensitive layer for a resist (e.g., a resist formed by the photosensitive resin compound), difference in dissolution rate between exposed area and non-exposed area can be occurred. In particular, the non-exposed area of the photosensitive layer is protected (especially becomes hydrophobic) and the surface of the layer becomes hydrophobic state, and meanwhile, in the exposed area, since the part which becomes hydrophilic state forms a hydrophilic domain, dissolution to a developer is accelerated (in the exposed area). Consequently, enlargement of difference in dissolution rate between non-exposed area and exposed area can be realized.

Therefore, the photoactive compound of the present invention is advantageously used for a resist composition, and the photosensitive resin composition comprising the photoactive compound is employed in a variety of application such as a material for forming circuits (a resist for semiconductor production, a printed wiring board, etc.), a material for forming image (a printing plate material, a materials for relief printing, etc.). In particular, the present invention can be advantageously utilized in the resist for semiconductor production because both high sensitivity and high resolution can be achieved.

Since the photoactive compound of the present invention is capable of hydrophilicity by deprotection owing to light exposure, sensitivity and resolution of resists (e.g., resists formed by a photosensitive resin composition including the photoactive compound) can be especially improved in the combination use of the photoactive compound with a photosensitizer. Moreover, improvement of sensitivity to short wavelength beams emitted from an exposure light source can be realized, and resolution can be improved in minute patterns. Furthermore, since difference in dissolution rate between exposed area and non-exposed area to developers can be enlarged, forming minute patters with superior sensitivity and excellent resolution can be attained.

EXAMPLES

Hereinafter, the present invention will be described in further detail based on examples, and the examples should by no means be construed as defining the scope of the invention.

Examples 1 to 110 (syntheses of photoactive compounds)

Example 1

Synthesis of 1-(1-ethoxy)ethoxy-4-isopropylbenzene (Compound 1)

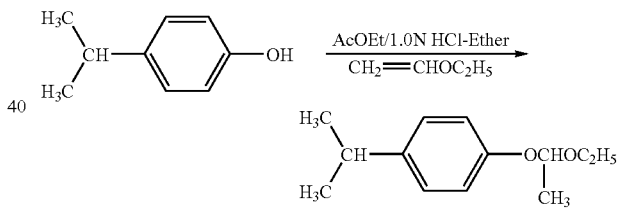

Compound 1

To 50 ml of dehydrated ethyl acetate (AcOEt) were added 5.0 g (36.7 mmol) of 4-isopropylphenol and 1.7 ml of hydrochloric acid/ether (HCl-Ether) solution (1.0 mol/L), and temperature of the reaction system was controlled to 40° C. Ethyl vinyl ether (7.9 g: 109.6 mmol) was added dropwise to the mixture, and the resultant mixture was stirred overnight. After the completion of the reaction, the reaction mixture was washed with an aqueous solution of sodium hydrogencarbonate, and washed with water to remove the solvent. Thus obtained mixture was purified by silica gel column chromatography (eluent: hexane) to provide 7.0 g (33.6 mmol) of 1-(1-ethoxy)ethoxy-4-isopropylbenzene.

$^1$H-NMR spectrum of the obtained 1-(1-ethoxy)ethoxy-4-isopropylbenzene is shown in FIG. 1.

$^1$H-NMR(CDCl$_3$) ppm: 1.10-1.30(m, 9H, iso-Pr and terminal CH$_3$), 1.49(d, 3H, branched CH$_3$), 2.80-3.00(m, 1H, CH), 3.45-3.70(m, 1H, OCH$_2$), 3.70-3.90(m, 1H, OCH$_2$), 5.35(q, 1H, branched OCH), 6.95(d, 2H, C$_6$H$_4$), 7.15(d, 2H, C$_6$H$_4$)

Example 2

Synthesis of 1-(tert-butoxycarbonyloxy)-4-isopropylbenzene (Compound 2)

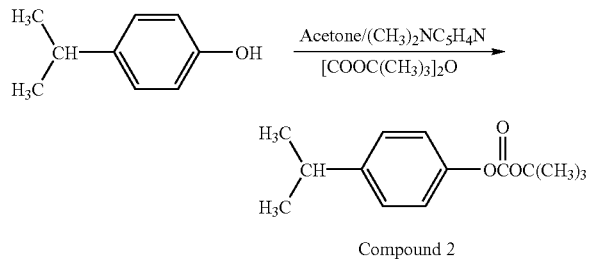

Compound 2

To 50 ml of dehydrated acetone (Acetone) were added 5.0 g (36.7 mmol) of 4-isopropylphenol and 4.5 mg ($3.7 \times 10^{-2}$ mmol) of 4-dimethylaminopyridine [$(CH_3)_2NC_5H_4N$], and the mixture was heated to 40° C. After heating, 8.0 g (36.7 mmol) of di-tert-butyldicarbonate was added dropwise to the mixture and the resultant mixture was stirred for 24 hours. After the completion of the reaction, the reaction mixture was poured into an iced water, and alkalified with a minimum amount of potassium hydroxide to provide a solid. The resultant solid was collected by filtration, dried, and recrystallized from methanol to provide 8.3 g (35.1 mmol) of 1-(tert-butoxycarbonyloxy)-4-isopropylbenzene.

Figure 2:
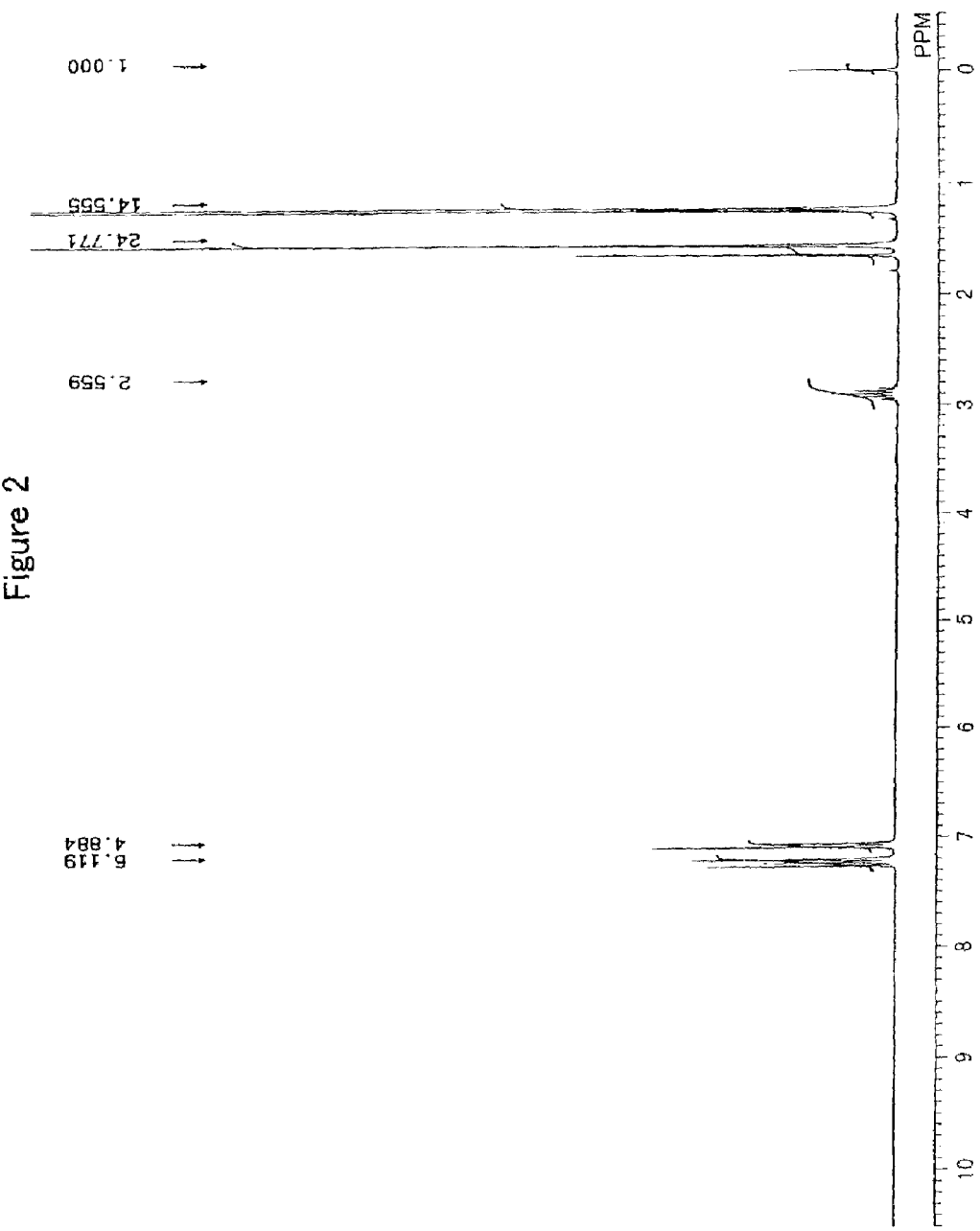
FIG. 2 shows $^1$H-NMR spectrum of 1-(t-butoxycarbonyloxy)-4-isopropylbenzene obtained in Example 4.

$^1$H-NMR spectrum of the obtained 1-(tert-butoxycarbonyloxy)-4-isopropylbenzene is shown in FIG. 2.

$^1$H-NMR(CDCl$_3$) ppm: 1.25(d, 6H, iso-Pr), 1.55(s, 9H, tert-Bu), 2.80-3.00(m, 1H, CH), 7.08(d, 2H, C$_6$H$_4$), 7.25(d, 2H, C$_6$H$_4$).

Example 3

Synthesis of 1-(tert-butoxycarbonyloxy)-4-(tert-butyl)benzene (Compound 3)

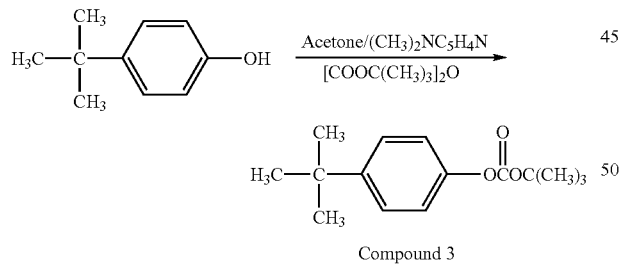

Compound 3

To 50 ml of dehydrated acetone were added 5.0 g (33.3 mmol) of 4-tert-butylphenol and 4.0 mg ($3.3 \times 10^{-2}$ mmol) of 4-dimethylaminopyridine, and the mixture was heated to 40° C. After heating, 7.3 g (33.3 mmol) of di-tert-butyldicarbonate was added dropwise to the mixture and the resultant mixture was stirred for 24 hours. After the completion of the reaction, the solvent was removed from the reaction mixture. The residue was dissolved in hexane and thus obtained mixture was treated with silica gel column chromatography to give 8.0 g (32.0 mmol) of 1-(tert-butoxycarbonyloxy)-4-(tert-butyl)benzene.

$^1$H-NMR(CDCl$_3$) ppm: 1.30(s, 9H, tert-Bu), 1.55(s, 9H, tert-Bu), 7.10(d, 2H, C$_6$H$_4$), 7.35(d, 2H, C$_6$H$_4$).

Example 4

Synthesis of 1-(tert-butoxycarbonyloxy)-4-bromobenzene (Compound 4)

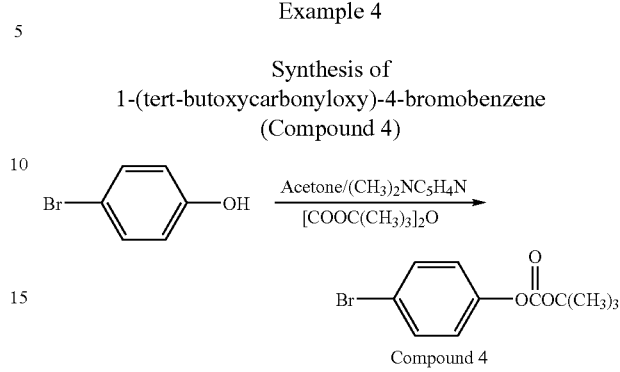

Compound 4

1-(tert-butoxycarbonyloxy)-4-bromobenzene was obtained in the same manner as in the Example 2, except for using 4-bromophenol instead of 4-isopropylphenol.

$^1$H-NMR(CDCl$_3$) ppm: 1.55(s, 9H, tert-Bu), 7.08(d, 2H, C$_6$H$_4$), 7.48(d, 2H, C$_6$H$_4$).

Example 5

Synthesis of 4-(tert-butoxycarbonyloxy) benzoic acid benzyl ester (Compound 5)

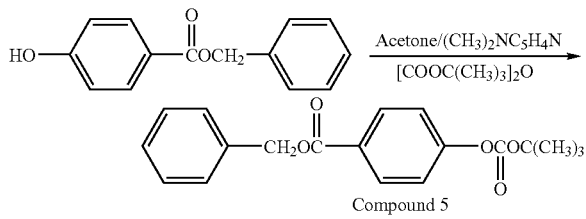

Compound 5

4-(tert-butoxycarbonyloxy) benzoic acid benzyl ester was obtained in the same manner as in the Example 2, except for using 4-hydroxybenzoic acid benzyl ester instead of 4-isopropylphenol.

$^1$H-NMR(CDCl$_3$) ppm: 1.55(s, 9H, tert-Bu), 5.37(s, 2H, CH$_2$), 7.25(d, 2H, C$_6$H$_4$), 7.30-7.38(m, 5H, C$_6$H$_5$), 8.10(d, 2H, C$_6$H$_4$).

Example 6

Synthesis of 1,4-di(tert-butoxycarbonyloxy)benzene (Compound 6)

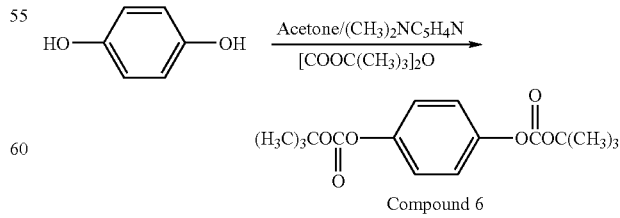

Compound 6

1,4-di(tert-butoxycarbonyloxy)benzene was obtained in the same manner as in the Example 2, except for using hydroquinone instead of 4-isopropylphenol.

$^1$H-NMR(CDCl$_3$) ppm: 1.55(s, 18H, tert-Bu), 7.18(s, 4H, C$_6$H$_4$).

Example 7

Synthesis of 4,4'-di(tert-butoxycarbonyloxy)biphenyl (Compound 7)

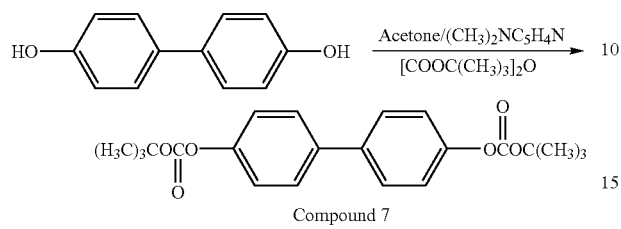

Compound 7

4,4'-di(tert-butoxycarbonyloxy)biphenyl was obtained in the same manner as in the Example 2, except for using 4,4'-biphenol instead of 4-isopropylphenol.

$^1$H-NMR (CDCl$_3$) ppm: 1.55(s, 18H, tert-Bu), 7.25(d, 4H, C$_6$H$_4$), 7.55(d, 4H, C$_6$H$_4$).

Example 8

Synthesis of 4-(tert-butoxycarbonyloxy) benzoic acid phenyl ester (Compound 8)

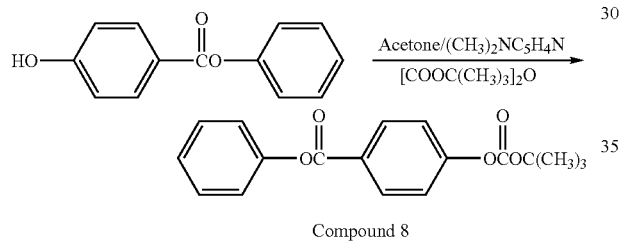

Compound 8

4-(tert-butoxycarbonyloxy) benzoic acid phenyl ester was obtained in the same manner as in the Example 2, except for using 4-hydroxybenzoic acid phenyl ester instead of 4-isopropylphenol.

$^1$H-NMR(CDCl$_3$) ppm: 1.55(s, 9H, tert-Bu), 7.18-7.50(m, 7H, C$_6$H$_4$ and C$_6$H$_5$), 8.24(d, 2H, C$_6$H$_4$).

Example 9

Synthesis of 4-(tert-butoxycarbonyloxy)-4'-bromobiphenyl (Compound 9)

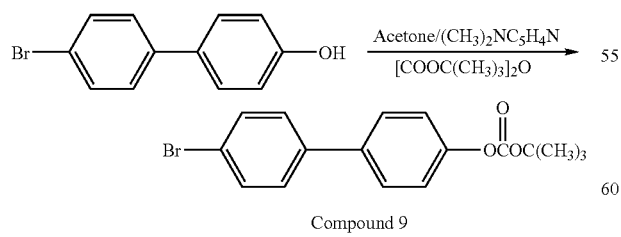

Compound 9

4-(tert-butoxycarbonyloxy)-4'-bromobiphenyl was obtained in the same manner as in the Example 2, except for using 4-bromo-4'-hydroxybiphenyl instead of 4-isopropylphenol.

$^1$H-NMR(CDCl$_3$) ppm: 1.55(s, 9H, tert-Bu), 7.25(d, 2H, C$_6$H$_4$), 7.43(d, 2H, C$_6$H$_4$), 7.50-7.60(m, 4H, C$_6$H$_4$).

Example 10

Synthesis of 2,6-di(tert-butoxycarbonyloxy)naphthalene (Compound 10)

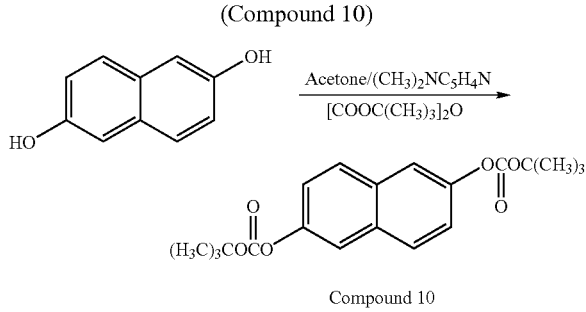

Compound 10

2,6-di(tert-butoxycarbonyloxy)naphthalene was obtained in the same manner as in the Example 2, except for using 2,6-dihydroxynaphthalene and toluene as the recrystallization solvent in lieu of 4-isopropylphenol and methanol, respectively.

$^1$H-NMR(CDCl$_3$) ppm: 1.55(s, 18H, tert-Bu), 7.35(d, 2H, C$_{10}$H$_6$), 7.67(t, 2H, C$_{10}$H$_6$), 7.83(d, 2H, C$_{10}$H$_6$).

Example 11

Synthesis of 1,5-di(tert-butoxycarbonyloxy)naphthalene (Compound 11)

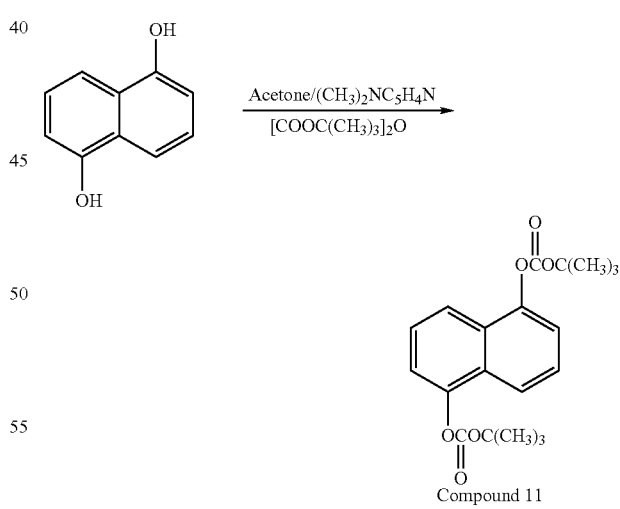

Compound 11

1,5-di(tert-butoxycarbonyloxy)naphthalene was obtained in the same manner as in the Example 2, except for using 1,5-dihydroxynaphthalene and toluene as the recrystallization solvent instead of 4-isopropylphenol and methanol, respectively.

$^1$H-NMR(CDCl$_3$) ppm: 1.55(s, 18H, tert-Bu), 7.38(d, 2H, C$_{10}$H$_6$), 7.55(t, 2H, C$_{10}$H$_6$), 7.89(d, 2H, C$_{10}$H$_6$).

Example 12

Synthesis of 6-(tert-butoxycarbonyloxy)-2-bromonaphthalene (Compound 12)

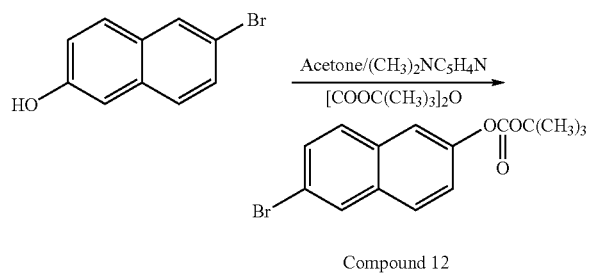

Compound 12

6-(tert-butoxycarbonyloxy)-2-bromonaphthalene was obtained in the same manner as in the Example 2, except for using 6-bromo-2-naphthol instead of 4-isopropylphenol.

$^1$H-NMR(CDCl$_3$) ppm: 1.55(s, 9H, tert-Bu), 7.38(d, 2H, C$_{10}$H$_6$), 7.55(t, 2H, C$_{10}$H$_6$), 7.89(d, 2H, C$_{10}$H$_6$).

Example 13

Synthesis of 1-(tert-butoxycarbonyloxy)-4-benzyloxybenzene (Compound 13)

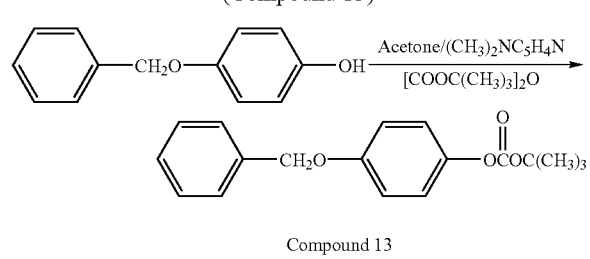

Compound 13

1-(tert-butoxycarbonyloxy)-4-benzyloxybenzene was obtained in the same manner as in the Example 2, except for using 4-(benzyloxy)phenol in lieu of 4-isopropylphenol.

$^1$H-NMR(CDCl$_3$) ppm: 1.55(s, 9H, tert-Bu), 5.05(s, 2H, CH$_2$O), 6.97(d, 2H, C$_6$H$_4$), 7.10(d, 2H, C$_6$H$_4$), 7.28-7.48(m, 5H, C$_6$H$_5$).

Example 14

Synthesis of 1-(tert-butoxycarbonyloxy)-4-(trans-4-propylcyclohexyl)benzene (Compound 14)

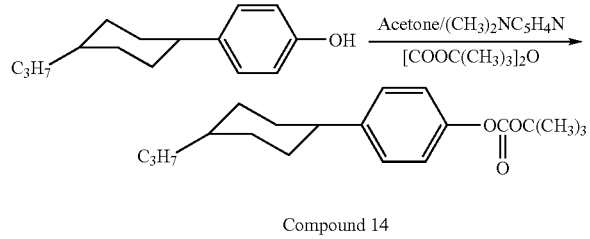

Compound 14

1-(tert-butoxycarbonyloxy)-4-(trans-4-propylcyclohexyl)benzene was obtained in the same manner as in the Example 2, except for using p-(trans-4-propylcyclohexyl)phenol instead of 4-isopropylphenol.

$^1$H-NMR(CDCl$_3$) ppm: 0.90(t, 3H, CH$_3$), 0.95-1.50(m, 9H, C$_2$H$_4$ and C$_6$H$_{10}$), 1.55(s, 9H, tert-Bu), 1.78-1.94(m, 4H, C$_6$H$_{10}$), 2.39-2.53(m, 1H, C$_6$H$_{10}$), 7.07(d, 2H, C$_6$H$_4$), 7.20(d, 2H, C$_6$H$_4$).

Example 15

Synthesis of 2,2-bis [4-(tert-butoxycarbonyloxy)phenyl]propane (Compound 15)

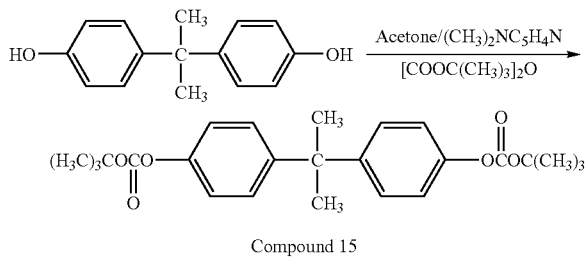

Compound 15

2,2-bis [4-(tert-butoxycarbonyloxy)phenyl]propane was obtained in the same manner as in the Example 2, except for using bisphenol A instead of 4-isopropylphenol.

$^1$H-NMR(CDCl$_3$) ppm: 1.55(s, 18H, tert-Bu), 1.68(s, 6H, iso-Pr), 7.07(d, 4H, C$_6$H$_4$), 7.23(d, 4H, C$_6$H$_4$).

Example 16

Synthesis of 1,3,5-tri(tert-butoxycarbonyloxy)benzene (Compound 16)

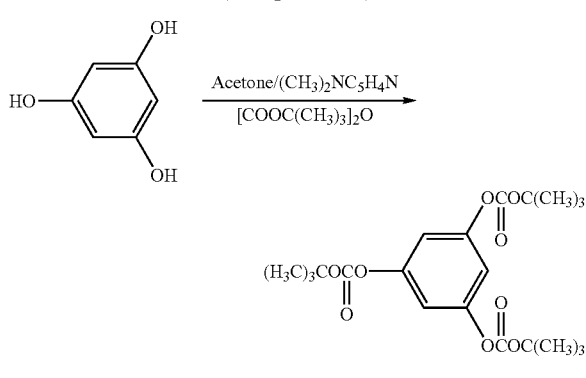

Compound 16

1,3,5-tri(tert-butoxycarbonyloxy)benzene was obtained in the same manner as in the Example 2, except for using 1,3,5-trihydroxybenzene instead of 4-isopropylphenol.

$^1$H-NMR(CDCl$_3$) ppm: 1.55(s, 27H, tert-Bu), 7.00(s, 3H, C$_6$H$_3$).

Example 17

Synthesis of 1,4-di(tert-butoxycarbonyloxy)-2,3,5,6-tetrafluorobenzene (Compound 17)

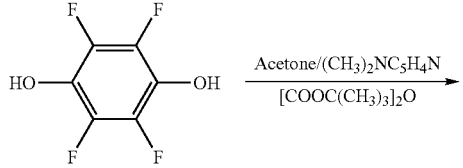

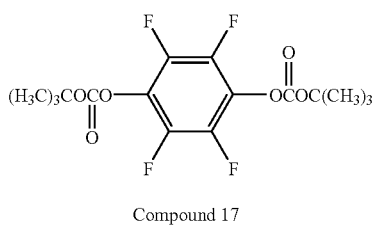

Compound 17

1,4-di(tert-butoxycarbonyloxy)-2,3,5,6-tetrafluorobenzene was obtained in the same manner as in the Example 2, except for using 2,3,5,6-tetrafluorohydroquinone in lieu of 4-isopropylphenol.

$^1$H-NMR(CDCl$_3$) ppm: 1.55(s, 18H, tert-Bu).

Example 18

Synthesis of 2,2-bis[4-(tert-butoxycarbonyloxy)phenyl]hexafluoropropane (Compound 18)

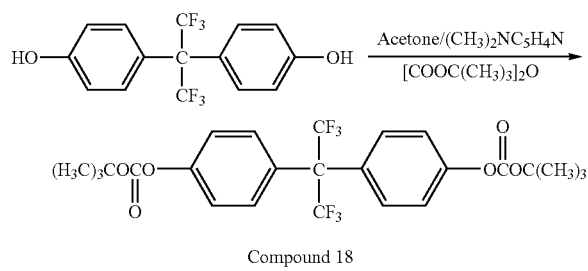

Compound 18

2,2-bis[4-(tert-butoxycarbonyloxy)phenyl]hexafluoropropane was obtained in the same manner as in the Example 2, except for using 2,2-bis(4-hydroxyphenyl)hexafluoropropane instead of 4-isopropylphenol.

$^1$H-NMR(CDCl$_3$) ppm: 1.55(s, 18H, tert-Bu), 7.20(d, 4H, C$_6$H$_4$), 7.40(d, 4H, C$_6$H$_4$).

Example 19

Synthesis of bis[4-(tert-butoxycarbonyloxy)phenyl]sulfone (Compound 19)

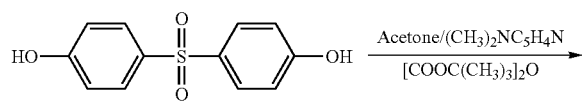

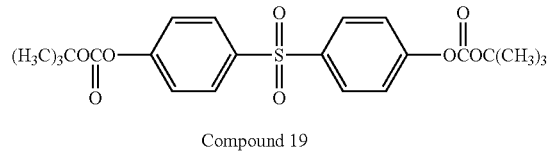

Compound 19

Bis[4-(tert-butoxycarbonyloxy)phenyl]sulfone was obtained in the same manner as in the Example 2, except for using bis(4-hydroxyphenyl) sulfone instead of 4-isopropylphenol.

$^1$H-NMR(CDCl$_3$) ppm: 1.55(s, 18H, tert-Bu), 7.35(d, 4H, C$_6$H$_4$), 7.96(d, 4H, C$_6$H$_4$).

Example 20

Synthesis of 9,9-bis[4-(tert-butoxycarbonyloxy)phenyl]fluorene (Compound 20)

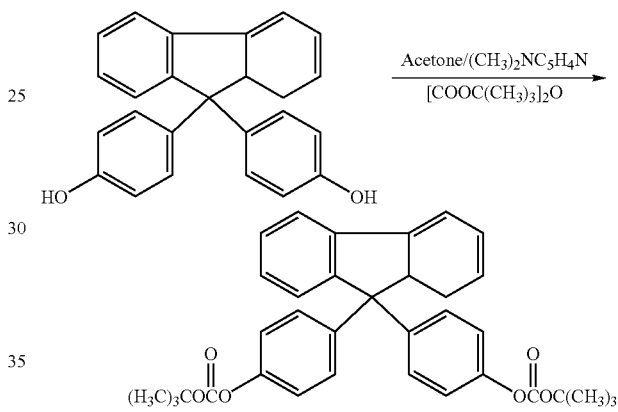

Compound 20

9,9-bis[4-(tert-butoxycarbonyloxy)phenyl]fluorene was obtained in the same manner as in the Example 2, except for using 9,9-bis(4-hydroxyphenyl)fluorene and toluene as the recrystallization solvent in lieu of 4-isopropylphenol and methanol, respectively.

$^1$H-NMR(CDCl$_3$) ppm: 1.55(s, 18H, tert-Bu), 7.03(d, 4H, C$_6$H$_4$), 7.27(d, 4H, C$_6$H$_4$), 7.15-7.41(m, 6H, C$_{13}$H$_8$), 7.76(d, 2H, C$_{13}$H$_8$).

Example 21

Synthesis of 1,4-bis[4-(tert-butoxycarbonyloxy)phenyl] cyclohexane (Compound 21)

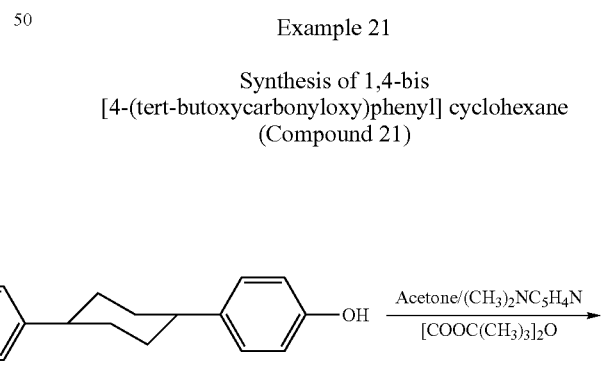

-continued

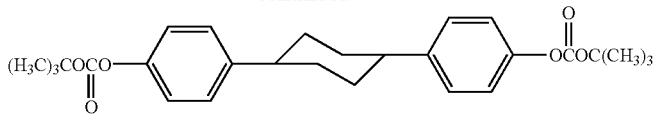

Compound 21

1,4-bis [4-(tert-butoxycarbonyloxy)phenyl] cyclohexane was obtained in the same manner as in the Example 2, except for using 4,4'-cyclohexylidenebisphenol and ethanol as the recrystallization solvent instead of 4-isopropylphenol and methanol, respectively.

$^1$H-NMR(CDCl$_3$) ppm: 1.55(s, 18H, tert-Bu), 2.20-2.30 (m, 4H, C$_6$H$_{10}$), 7.17(d, 4H, C$_6$H$_4$), 7.28(d, 4H, C$_6$H$_4$).

Example 22

Synthesis of 1,3-bis {2-[4-(tert-butoxycarbonyloxy)phenyl] propan-2-yl} benzene (Compound 22)

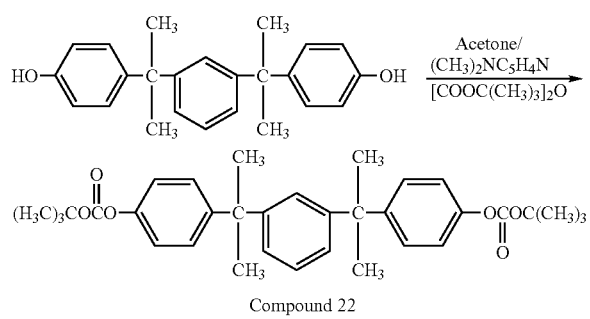

Compound 22

1,3-bis{2-[4-(tert-butoxycarbonyloxy)phenyl]propan-2-yl} benzene was obtained in the same manner as in the Example 2, except for using 4,4'-(1,3-phenylenediisopropylidene)bisphenol and ethanol as the recrystallization solvent in lieu of 4-isopropylphenol and methanol, respectively.

$^1$H-NMR(CDCl$_3$) ppm: 1.55(s, 18H, tert-Bu), 1.62(s, 12H, CH$_3$), 6.98-7.09(m, 6H, C$_6$H$_4$), 7.10-7.20(m, 6H, C$_6$H$_4$).

Example 23

Synthesis of 1-(tert-butoxycarbonyloxy)-4-(trans-4-pentylcyclohexyl)benzene (Compound 23)

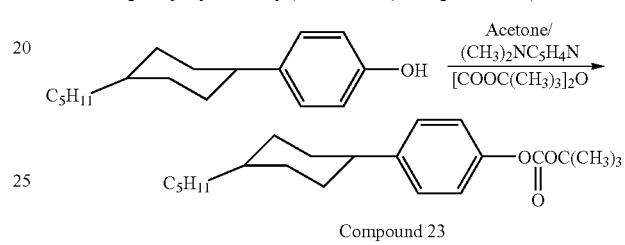

Compound 23

1-(tert-butoxycarbonyloxy)-4-(trans-4-pentylcyclohexyl)benzene was obtained in the same manner as in the Example 2, except for using p-(trans-4-pentylcyclohexyl)phenol instead of 4-isopropylphenol.

$^1$H-NMR(CDCl$_3$) ppm: 0.90(t, 3H, CH$_3$), 0.95-1.72(m, 13H, C$_4$H$_8$ and C$_6$H$_{10}$), 1.55(s, 9H, tert-Bu), 1.78-1.94(m, 4H, C$_6$H$_{10}$), 2.39-2.53(m, 1H, C$_6$H$_{10}$) 7.07(d, 2H, C$_6$H$_4$), 7.20(d, 2H, C$_6$H$_4$).

Example 24

Synthesis of 4'-(tert-butoxycarbonyloxy)phenyl-4-n-propyloxybenzoate (Compound 24)

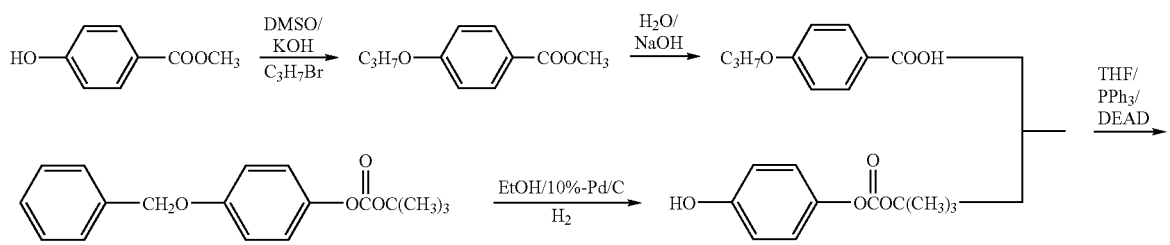

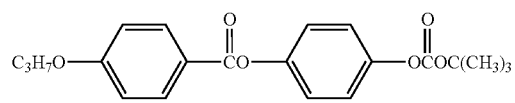

Compound 24

(i) Synthesis of 4-n-propyloxybenzoic acid

Methyl 4-hydroxybenzoate (15.4 g: 101.2 mmol) was dissolved in 150 ml of dimethylsulfoxide (DMSO), and an aqueous solution of potassium hydroxide ($KOH/H_2O$: 7 g/15 ml) was added to the mixture. The resultant mixture was stirred until dissolving homogeneously. Next, 12.5 g (101.6 mmol) of n-propyl bromide was added thereto, and the reaction was carried out at a room temperature for 24 hours. The reaction mixture was poured into 1 L of an iced water and the resultant precipitate was collected by filtration. The obtained precipitate was dissolved in 300 ml of ethanol, and an aqueous solution of sodium hydroxide ($NaOH/H_2O$: 5 g/100 ml) was added thereto. Thus obtained mixture was refluxed by heating for 1 hour, and water (the amount of the water: about 300 ml) was added thereto with removing ethanol (EtOH). After cooling to a room temperature, the transparent solution was acidified by adding a concentrated hydrochloric acid. The resultant white precipitate was filtered and recrystallized from toluene to give 17.5 g (97.2 mmol) of 4-n-propyloxybenzoic acid.

(ii) Synthesis of 4-(tert-butoxycarbonyloxy)phenol

Ethanol (100 ml) and 10%-Pd/C (0.5 g) were added to 1-(tert-butoxycarbonyloxy)-4-benzyloxybenzene (10.0 g:33.3 mmol) of synthesized in the Example 13, and the mixture was subjected to hydrogenolysis under $H_2$ atmosphere with stirring at a room temperature. After completion of the reaction, Pd/C was removed by filtration, and then the solvent was removed. The obtained residue was recrystallized from a mixed solvent of hexane/toluene to give 6.74 g (32.1 mmol) of 4-(tert-butoxycarbonyloxy)phenol.

(iii) Synthesis of 4'-(tert-butoxycarbonyloxy)phenyl-4-n-propyloxybenzoate

To 1.64 g (10 mmol) of 4-propyloxybenzoic acid and 2.1 g (10 mmol) of 4-(tert-butoxycarbonyloxy)phenol obtained by the steps (i) and (ii), respectively, was added 2.62 g (10 mmol) of triphenylphosphine ($PPh_3$), and the mixture was homogeneously dissolved in 50 ml of dried tetrahydrofuran (THF). Next, azodicarboxylic acid diethyl ester (1.74 g: 10 mmol) was added dropwise to the mixture with cooling with ice, and the reaction was conducted at a room temperature for 24 hours. After completion of the reaction, the solvent was evaporated. The resultant residue was purified by silica gel column chromatography (eluent: toluene), and recrystallized from methanol to give 1.9 g (5.1 mmol) of 4'-(tert-butoxycarbonyloxy)phenyl-4-n-propyloxybenzoate.

$^1$H-NMR($CDCl_3$) ppm: 1.08 (t, 3H, $CH_3$), 1.55 (s, 9H, tert-Bu), 1.80-1.94 (m, 2H, $CH_2$), 4.02 (t, 2H, $OCH_2$), 6.98 (d, 2H, $C_6H_4$), 7.25 (d, 4H, $C_6H_4$), 8.15 (d, 2H, $C_6H_4$).

Example 25

Synthesis of 4'-n-propylphenyl-4-(tert-butoxycarbonyloxy)benzoate (Compound 25)

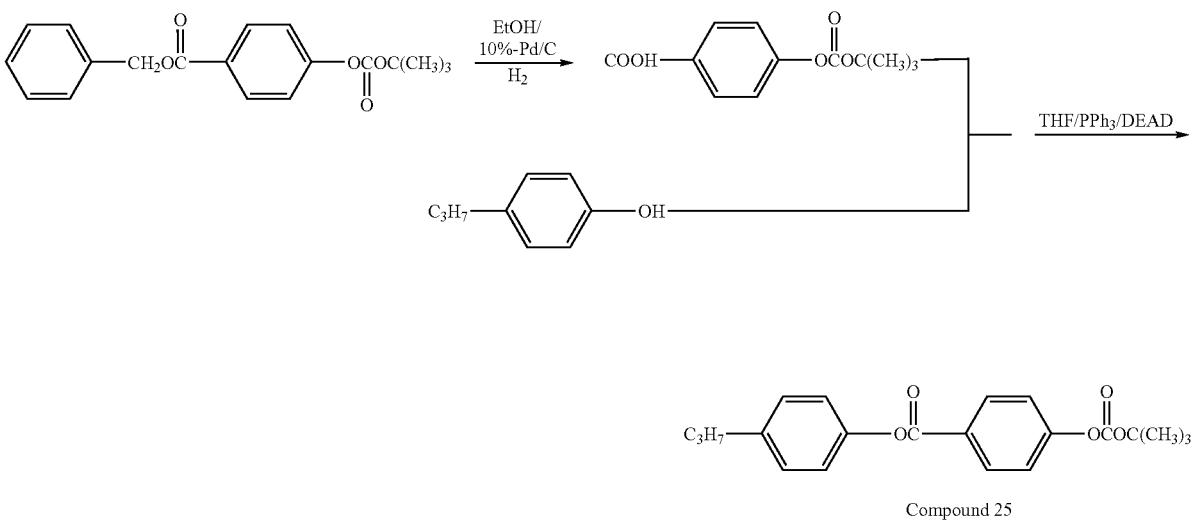

Compound 25

(i) Synthesis of 4-(tert-butoxycarbonyloxy)benzoic acid 4-(tert-butoxycarbonyloxy)benzoic acid was obtained by conducting hydrogenolysis in the same manner as in the step (ii) of the Example 24, except for using 1-(tert-butoxycarbonyloxy)-4-benzoic acid benzyl ester synthesized in the Example 5 instead of 1-(tert-butoxycarbonyloxy)-4-benzyloxybenzene.

(ii) Synthesis of 4'-n-propylphenyl-4-(tert-butoxycarbonyloxy)benzoate

4'-n-propylphenyl-4-(tert-butoxycarbonyloxy)benzoate was obtained in the same manner as in the step (iii) of the Example 24, except for using 4-(tert-butoxycarbonyloxy)benzoic acid obtained in the step (i) and 4-n-propylphenol, instead of 4-n-propyloxybenzoic acid and 4-(tert-butoxycarbonyloxy)phenol, respectively.

$^1$H-NMR($CDCl_3$) ppm: 0.98(t, 3H, $CH_3$), 1.55(s, 9H, tert-Bu), 1.50-1.77(m, 2H, $CH_2$), 2.62(t, 2H, $CH_2$), 7.10(d, 2H, $C_6H_4$), 7.23(d, 2H, $C_6H_4$), 7.33(d, 2H, $C_6H_4$), 8.24(d, 2H, $C_6H_4$).

Example 26

Synthesis of tri[4-(tert-butoxycarbonyloxy)phenyl] trimesate (Compound 26)

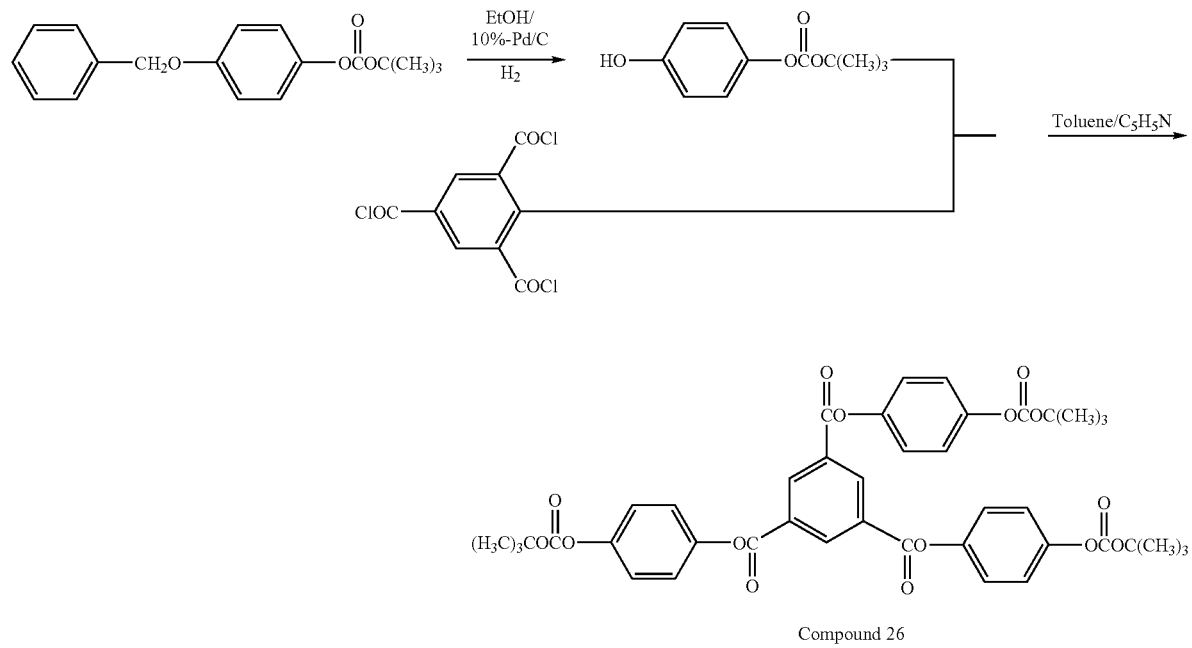

Compound 26

To 1.5 g (5.6 mmol) of trimesoyl chloride were added 30 ml of toluene (Toluene) and 1.5 g (17.0 mmol) of pyridine. Further, thereto was added 3.55 g (16.9 mmol) of 4-(tert-butoxycarbonyloxy)phenol synthesized in the step (ii) of the Example 24, and the reaction was conducted at a room temperature for 24 hours. After the completion of the reaction, the reaction mixture was subjected to recrystallization from ethanol and 2.8 g (3.7 mmol) of tri[4-(tert-butoxycarbonyloxy)phenyl] trimesate was obtained.

$^1$H-NMR(CDCl$_3$) ppm: 1.55(s, 27H, tert-Bu), 7.28(s, 12H, C$_6$H$_4$), 9.22(s, 3H, C$_6$H$_3$).

Example 27

Synthesis of 4'-n-propyloxyphenyl-4-(tert-butoxycarbonyloxy)benzoate (Compound 27)

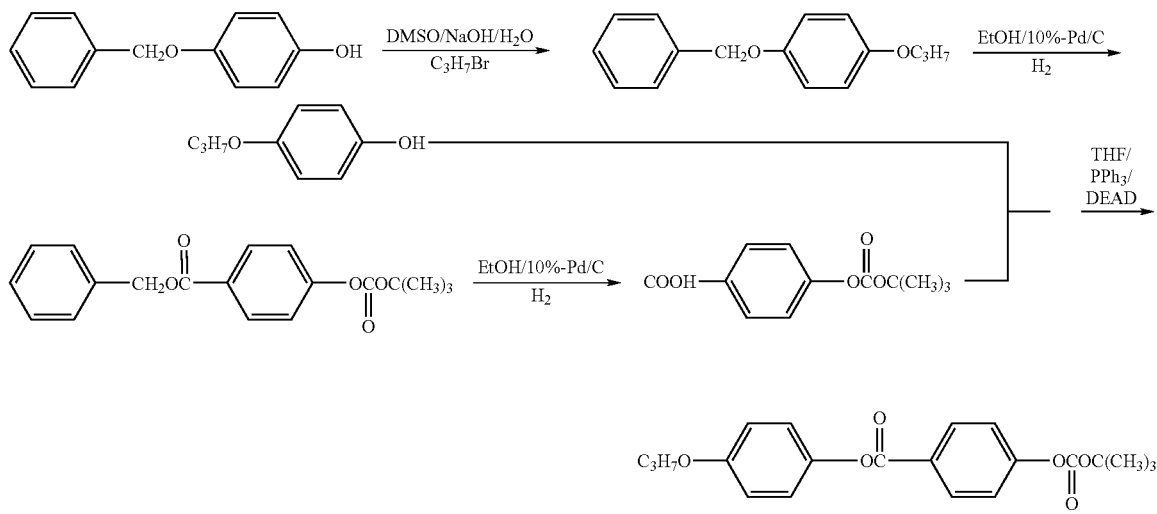

Compound 27

(i) Synthesis of 1-(n-propyloxy)-4-benzyloxybenzene

In 75 ml of dimethylsulfoxide (DMSO) was dissolved 7.5 g (37.5 mmol) of 4-(benzyloxy)phenol, and an aqueous solution of sodium hydroxide (NaOH/H₂O: 1.65 g/15 ml) was added thereto. The mixture was stirred until dissolving homogeneously. Next, 5.0 g (40.7 mmol) of n-propyl bromide was added to the mixture, and the resultant mixture was subjected to a reaction at a room temperature for 24 hours. The reaction mixture was poured into 1 L of an iced water, and a solid was formed by stirring. The resultant solid was collected by filtration, dried, and recrystallized from methanol to give 8.82 g (36.4 mmol) of 1-(n-propyloxy)-4-benzyloxybenzene.

(ii) Synthesis of 1-(n-propyloxy)phenol 1-(n-propyloxy)phenol was obtained by conducting hydrogenolysis in the same manner as in the step (ii) of the Example 24, except for using 1-(n-propyloxy)-4-benzyloxybenzene synthesized in the step (i) instead of 1-(tert-butoxycarbonyloxy)-4-benzyloxybenzene.

(iii) Synthesis of 4'-n-propyloxyphenyl-4-(tert-butoxycarbonyloxy)benzoate

4'-n-propyloxyphenyl-4-(tert-butoxycarbonyloxy)benzoate was obtained in the same manner as in the step (iii) of the Example 24, except for using 4-(tert-butoxycarbonyloxy)benzoic acid obtained in the step (i) of the Example 25 and 1-(n-propyloxy)phenol synthesized in the step (ii) instead of 4-n-propyloxybenzoic acid and 4-(tert-butoxycarbonyloxy)phenol, $^1$H-NMR(CDCl$_3$) ppm: 1.08(t, 3H, CH$_3$), 1.55(s, 9H, tert-Bu), 1.75-1.90(m, 2H, CH$_2$), 3.95(t, 2H, OCH$_2$), 6.98(d, 2H, C$_6$H$_4$), 7.10(d, 2H, C$_6$H$_4$), 7.33(d, 2H, C$_6$H$_4$), 8.24(d, 2H, C$_6$H$_4$).

Example 28

Synthesis of 4'-(tert-butoxycarbonyloxy)phenyl-4-n-propylbenzoate (Compound 28)

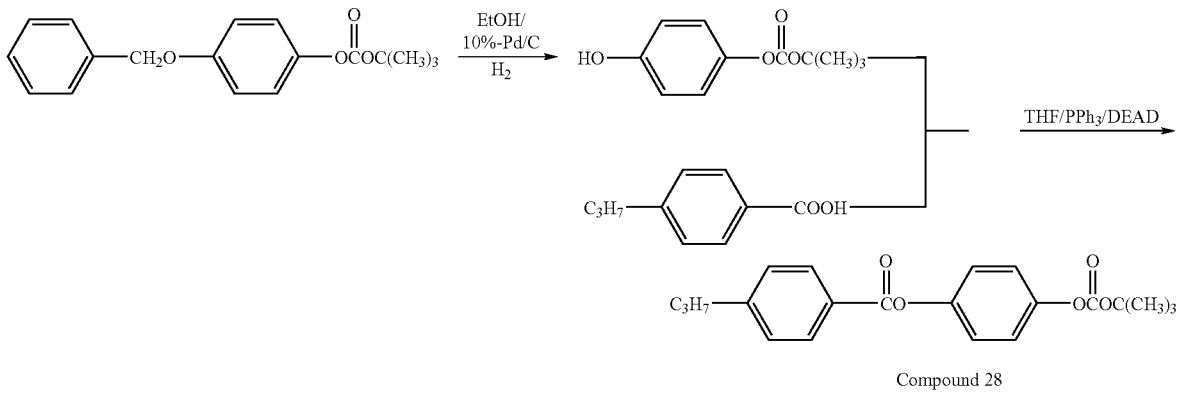

4'-(tert-butoxycarbonyloxy)phenyl-4-n-propylbenzoate was obtained in the same manner as in the step (iii) of the Example 24, except for using 4-n-propylbenzoic acid in lieu of 4-n-propyloxybenzoic acid.

$^1$H-NMR(CDCl$_3$) ppm: 0.98(t, 3H, CH$_3$), 1.55(s, 9H, tert-Bu), 1.60-1.85(m, 2H, CH$_2$), 2.69(t, 2H, CH$_2$), 7.25(d, 4H, C$_6$H$_4$), 7.32(d, 2H, C$_6$H$_4$), 8.10(d, 2H, C$_6$H$_4$).

Example 29

Synthesis of 4'-(tert-butoxycarbonyloxy)phenyl-trans-4-n-propylcyclohexylcarboxylate (Compound 29)

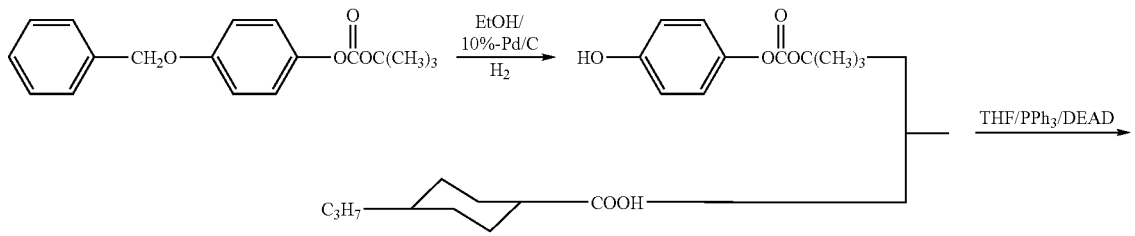

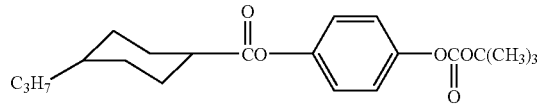

Compound 29

4'-(tert-butoxycarbonyloxy)phenyl-trans-4-n-propylcyclohexylcarboxylate was obtained in the same manner as in the step (iii) of the Example 24, except for using trans-4-n-propylcyclohexylcarboxylic acid instead of 4-n-propyloxybenzoic acid.

$^1$H-NMR(CDCl$_3$) ppm: 0.92(t, 3H, CH$_3$), 0.90-1.08(m, 2H, CH$_2$), 1.02-1.44(m, 5H, CH$_2$ and C$_6$H$_{10}$), 1.55(s, 9H, tert-Bu), 1.45-1.68(m, 2H, CH$_2$), 1.88(d, 2H, C$_6$H$_{10}$), 2.14(d, 2H, C$_6$H$_{10}$), 2.38-2.55(m, 1H, C$_6$H$_{10}$), 7.06(d, 2H, C$_6$H$_4$), 7.17(d, 2H, C$_6$H$_4$).

Example 30

Synthesis of 4'-(tert-butoxycarbonyloxy)phenyl-4-n-propyloxybenzyl ether (Compound 30)

ried out at a room temperature for 24 hours. The reaction mixture was poured into 1 L of an iced water and a solid was formed by stirring. The resultant solid was collected by filtration, dried, and recrystallized from toluene to provide 15.8 g (95.2 mmol) of 4-n-propyloxybenzyl alcohol.

(ii) Synthesis of 4'-(tert-butoxycarbonyloxy)phenyl-4-n-propyloxybenzyl ether

4'-(tert-butoxycarbonyloxy)phenyl-4-n-propyloxybenzyl ether was obtained in the same manner as in the step (iii) of the Example 24, except for using 4-n-propyloxybenzyl alcohol synthesized in the step (i) instead of 4-n-propyloxybenzoic acid.

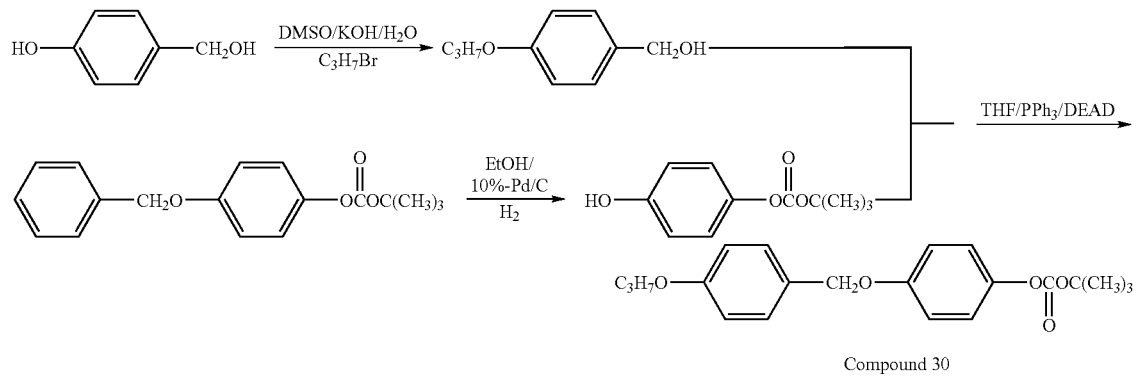

Compound 30

(i) Synthesis of 4-n-propyloxybenzyl alcohol 4-hydroxybenzyl alcohol (12.4 g: 100.0 mmol) was dissolved in 100 ml of dimethylsulfoxide (DMSO), and an aqueous solution of potassium hydroxide (KOH/H$_2$O: 6.6 g/15 ml) was added to the mixture. After the resultant mixture was dissolved homogeneously by stirring, n-propyl bromide (12.3 g:100.0 mmol) was added thereto, and the reaction was car- $^1$H-NMR(CDCl$_3$) ppm: 1.06(t, 3H, CH$_3$), 1.55(s, 9H, tert-Bu), 1.74-1.90(m, 2H, CH$_2$), 3.95(t, 2H, OCH$_2$), 4.99(s, 2H, CH$_2$O), 6.92(t, 4H, C$_6$H$_4$), 7.08(d, 2H, C$_6$H$_4$), 7.33(d, 2H, C$_6$H$_4$).

Example 31

Synthesis of 1-[4-(tert-butoxycarbonyloxy)phenyl]-2-(4-n-propylphenyl)acetylene (Compound 31)

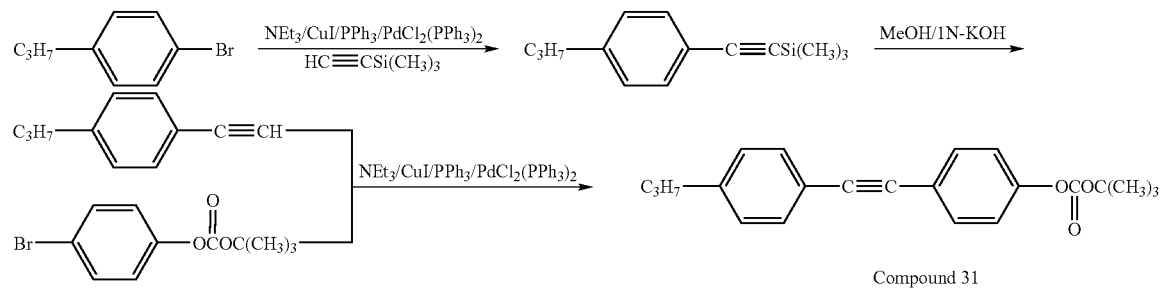

Compound 31

(i) Synthesis of 1-(4-n-propylphenyl)-2-trimethylsilylacetylene

To 15.0 g (75.4 mmol) of 1-n-propyl-4-bromobenzene were added 8.8 g (89.8 mmol) of trimethylsilylacetylene and 100 ml of triethylamine (NEt$_3$), and the reaction system was purged with argon. Next were added 81 mg (0.4 mmol) of copper (I) iodide (CuI), 324 mg (1.2 mmol) of triphenylphosphine, and 162 mg of dichlorobistriphenylphosphine palladium (II) [PdCl$_2$(PPh$_3$)$_2$] to the reaction system, and the mixture was subjected to reaction for 24 hours with heating and refluxing. After completion of the reaction, the reaction mixture was poured into an iced water, and the resultant mixture was acidified by adding hydrochloric acid. After the resultant water-insoluble oil was extracted with hexane, the hexane phase was washed with water. By removing hexane from the hexane phase, 14.2 g (65.7 mmol) of 1-(4-n-propylphenyl)-2-trimethylsilylacetylene was obtained.

(ii) Synthesis of 4-n-propylphenylacetylene

Methanol (150 ml) and an aqueous solution of 1N-potassium hydroxide (100 ml) were added to 14.2 g (65.7 mmol) of 1-(4-n-propylphenyl)-2-trimethylsilylacetylene synthesized in the step (i), and the mixture was subjected to hydrolysis with vigorously stirring overnight. After completion of the reaction, methanol was removed and the resultant residue was extracted with hexane. After removing hexane from the hexane phase, the resultant residue was washed with water to give 9.4 g (65.3 mmol) of 4-n-propylphenylacetylene.

(iii) Synthesis of 1-[4-(tert-butoxycarbonyloxy)phenyl]-2-(4-n-propylphenyl)acetylene The reaction was carried out in the same manner as in the step (i), except for using 4-n-propylphenylacetylene synthesized in the step (ii) and 1-(tert-butoxycarbonyloxy)-4-bromobenzene synthesized in the Example 4 instead of 1-n-propyl-4-bromobenzene and trimethylsilylacetylene, respectively. After completion of the reaction, the reaction solution was poured into an iced water, and the resultant solution was acidified by adding hydrochloric acid. After the resultant solid was collected by filtration, the collected solid was washed with water, dried, and recrystallized successively from hexane and ethanol to provide 4.1 g (12.1 mmol) of 1-[4-(tert-butoxycarbonyloxy)phenyl]-2-(4-n-propylphenyl)acetylene.

$^1$H-NMR(CDCl$_3$) ppm: 0.95(t, 3H, CH$_3$), 1.55(s, 9H, tert-Bu), 1.55-1.75(m, 2H, CH$_2$), 2.60(t, 2H, CH$_2$), 7.15(d, 4H, C$_6$H$_4$), 7.43(d, 2H, C$_6$H$_4$), 7.52(d, 2H, C$_6$H$_4$).

Example 32

Synthesis of 1-[4-(tert-butoxycarbonyloxy)phenyl]-2-(4-n-propyloxyphenyl)acetylene (Compound 32)

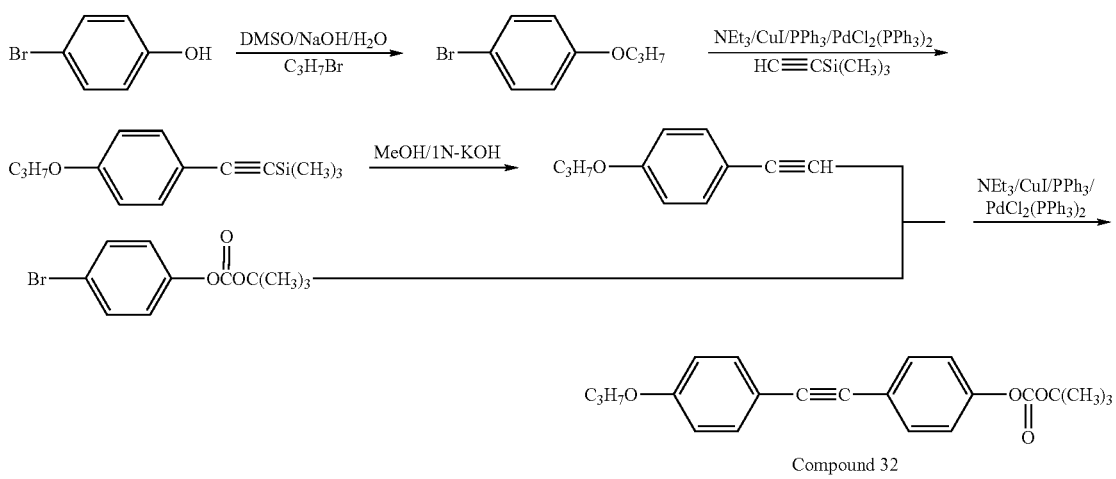

Compound 32

(i) Synthesis of 1-bromo-4-n-propyloxybenzene

In 100 ml of dimethylsulfoxide was dissolved 17.3 g (100.0 mmol) of 4-bromophenol, and an aqueous solution of sodium hydroxide (NaOH/H$_2$O: 4.0 g/25 ml) was added thereto. The resultant mixture was stirred until dissolving homogeneously. Next was added 12.3 g (100.0 mmol) of n-propyl bromide to the resultant mixture, and the reaction was carried out at a room temperature for 24 hours. The reaction mixture was poured into an iced water, and the resultant oil was extracted with hexane. After the hexane phase was washed with water, hexane was removed from the hexane phase to give 20.5 g (95.3 mmol) of 1-bromo-4-n-propyloxybenzene.

(ii) Synthesis of 1-(4-n-propyloxyphenyl)-2-trimethylsilylacetylene 1-(4-n-propyloxyphenyl)-2-trimethylsilylacetylene was obtained in the same manner as in the step (i) of the Example 31, except for using 1-bromo-4-n-propyloxybenzene synthesized in the step (i) instead of 1-bromo-4-n-propylbenzene.

(iii) Synthesis of 4-n-propyloxyphenylacetylene 4-n-propyloxyphenylacetylene was obtained in the same manner as in the step (ii) of the Example 31, except for using 1-(4-n-propyloxyphenyl)-2-trimethylsilylacetylene synthesized in the step (ii) instead of 1-(4-n-propylphenyl)-2-trimethylsilylacetylene.

(iv) Synthesis of 1-[4-(tert-butoxycarbonyloxy)phenyl]-2-(4-n-propyloxyphenyl)acetylene 1-[4-(tert-butoxycarbonyloxy)phenyl]-2-(4-n-propyloxyphenyl)acetylene was gained in the same manner as in the step (iii) of the Example 31, except for using 4-(n-propyloxy)phenylacetylene obtained in the step (iii) instead of 4-n-propylphenylacetylene.

$^1$H-NMR(CDCl$_3$) ppm: 1.06(t, 3H, CH$_3$), 1.55(s, 9H, tert-Bu), 1.75-1.90(m, 2H, CH$_2$), 3.94(t, 2H, OCH$_2$), 6.87(d, 2H, C$_6$H$_4$), 7.15(d, 2H, C$_6$H$_4$), 7.45(d, 2H, C$_6$H$_4$), 7.50(d, 2H, C$_6$H$_4$).

Example 33

Synthesis of 4'-(tert-butoxycarbonyloxy)phenyl-4-n-propylbenzyl ether (Compound 33)

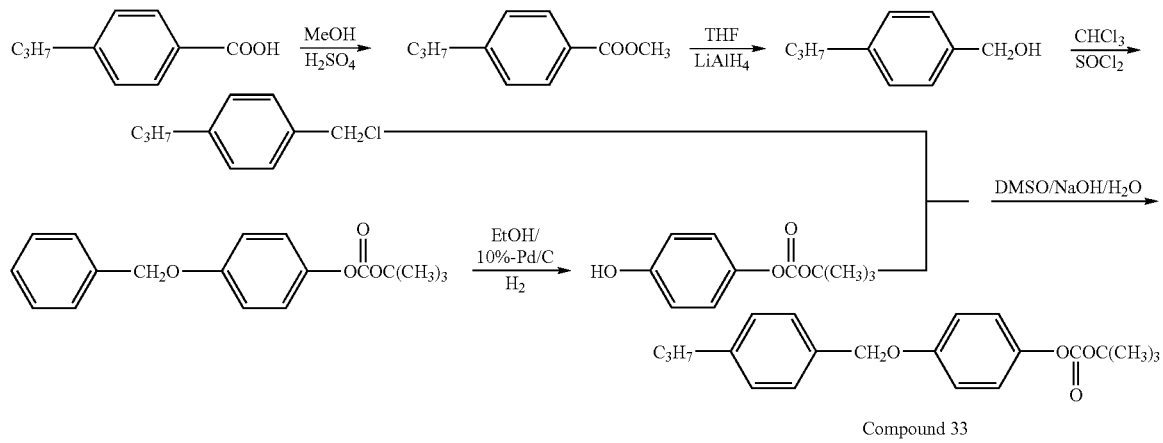

Compound 33

(i) Synthesis of 4-n-propylbenzoic acid methyl ester

In 40 ml of methanol (MeOH) was dissolved 10.0 g 61.0 mmol) of 4-n-propylbenzoic acid, and 2 ml of sulfuric acid was added to the mixture. The resultant mixture was refluxed for 24 hours, and most of the methanol was removed. Another methanol (400 ml) was added thereto with refluxing, and methanol was removed. Next, water was added to the reaction mixture, and the resultant oil was extracted with hexane. After the hexane phase was washed successively with an aqueous solution of sodium hydrogencarbonate and water, hexane was removed from the hexane phase to give 10.4 g (58.4 mmol) of 4-n-propylbenzoic acid methyl ester.

(ii) Synthesis of 4-n-propylbenzyl alcohol

Dried tetrahydrofuran (50 ml) in which 10.4 g (58.4 mmol) of 4-n-propylbenzoic acid methyl ester synthesized in step (i) was dissolved was dropwise added to 50 ml of dried tetrahydrofuran containing suspension of lithium aluminium hydride (1.54 g: 40.5 mmol) at a temperature of not more than 10° C. with cooling with ice, and reaction was carried out at a room temperature overnight. After the completion of the reaction, an excess amount of lithium aluminium hydride was reacted with methanol with cooling with ice. Next water and an aqueous solution of hydrochloric acid were successively added to the reaction mixture, and the resultant was extracted with hexane. After the hexane phase was washed with water, hexane was removed from the hexane phase to give 8.63 g (57.5 mmol) of 4-n-propylbenzyl alcohol.

(iii) Synthesis of 4-n-propylbenzyl chloride

In 50 ml of chloroform was dissolved 8.63 g (57.5 mmol) of 4-n-propylbenzyl alcohol synthesized in the step (ii), and 8.10 g (68.1 mmol) of thionyl chloride was added to the mixture. The mixture was subjected to reaction at a room temperature for 24 hours. After the completion of the reaction, the chloroform phase was washed successively with an aqueous solution of sodium hydrogencarbonate and water. Chloroform was removed from the chloroform phase to give 9.40 g (55.8 mmol) of 4-n-propylbenzylchloride.

(iv) Synthesis of 4'-(tert-butoxycarbonyloxy)phenyl-4-n-propylbenzyl ether

4'-(tert-butoxycarbonyloxy)phenyl-4-n-propylbenzyl ether was obtained in the same manner as in the step (i) of the Example 27, except for using 4-(tert-butoxycarbonyloxy) phenol synthesized in the step (ii) of the Example 24 and 4-n-propylbenzyl chloride synthesized in the step (iii) in lieu of 4-(benzyloxy)phenol and n-propyl bromide, respectively, and using hexane as the recrystallization solvent.

$^1$H-NMR(CDCl$_3$) ppm: 0.92(t, 3H, CH$_3$), 1.55(s, 9H, tert-Bu), 1.57-1.78(m, 2H, CH$_2$), 2.60(t, 2H, CH$_2$), 5.00(s, 2H, CH$_2$O), 6.94(d, 2H, C$_6$H$_4$), 7.07(d, 2H, C$_6$H$_4$), 7.19(d, 2H, C$_6$H$_4$), 7.33(d, 2H, C$_6$H$_4$).

Example 34

Synthesis of 4'-(tert-butoxycarbonyloxy)phenyl-4-methylbenzyl ether (Compound 34)

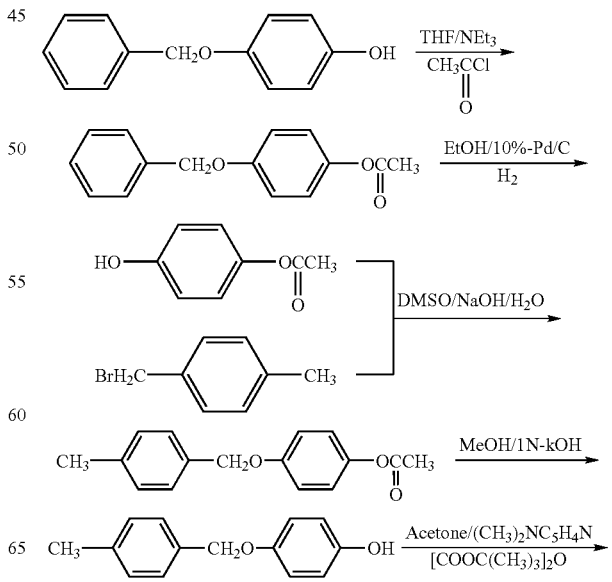

-continued

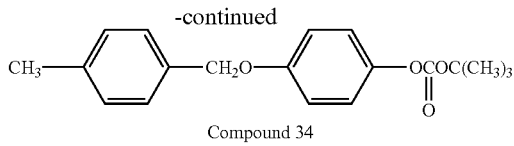

Compound 34

(i) Synthesis of benzyl-(4-acetoxyphenyl)ether

To 35.0 g (175.0 mmol) of 4-(benzyloxy)phenol were added 100 ml of dried tetrahydrofuran and 17.7 g (175.2 mmol) of triethylamine, and the mixture was homogeneously dissolved. Next, 13.75 g (175.2 mmol) of acetyl chloride was added to the resultant mixture with cooling with ice. The reaction was conducted at a room temperature for 24 hours. The reaction mixture was poured into 500 ml of an iced water and a solid was formed by stirring. The resultant solid was collected by filtration, dried, and recrystallized from a mixed solvent of hexane/toluene to give 40.3 g (166.5 mmol) of benzyl-(4-acetoxyphenyl)ether.

(ii) Synthesis of 4-acetoxyphenol 4-acetoxyphenol was obtained by conducting hydrogenolysis in the same manner as in the step (ii) of the Example 24, except for using benzyl-(4-acetoxyphenyl)ether obtained in the step (i) in lieu of 1-(tert-butoxycarbonyloxy)-4-benzyloxybenzene, and using toluene as the recrystallization solvent.

(iii) Synthesis of 4'-acetoxyphenyl-4-methylbenzyl ether

4'-acetoxyphenyl-4-methylbenzyl ether was obtained in the same manner as in the step (i) of the Example 27, except for using 4-acetoxyphenol synthesized in the step (ii) and 4-methylbenzyl chloride instead of 4-(benzyloxy)phenol and n-propyl bromide, respectively.

(iv) Synthesis of 4'-hydroxyphenyl-4-methylbenzyl ether

Methanol (130 ml) and potassium hydroxide (5.0 g:89.1 mmol) were added to 8.0 g (31.3 mmol) of 4'-acetoxyphenyl-4-methylbenzyl ether synthesized in the step (iii), and the mixture was subjected to hydrolysis under heating with stirring. After the solvent in the reaction mixture was replaced with water, the resultant solid was collected by filtration, dried, and recrystallized from toluene to give 6.3 g (29.4 mmol) of 4'-hydroxyphenyl-4-methylbenzyl ether. ( v) Synthesis of 4'-(tert-butoxycarbonyloxy)phenyl-4-methylbenzyl ether 4'-(tert-butoxycarbonyloxy)phenyl-4-methylbenzyl ether was obtained in the same manner as in the Example 2, except for using 4'-hydroxyphenyl-4-methylbenzyl ether synthesized in the step (iv) instead of 4-isopropylphenol.

$^1$H-NMR(CDCl$_3$) ppm: 1.55(s, 9H, tert-Bu), 2.36(s, 3H, CH$_3$), 5.00(s, 2H, CH$_2$O), 6.94(d, 2H, C$_6$H$_4$), 7.07(d, 2H, C$_6$H$_4$), 7.19 (d, 2H, C$_6$H$_4$), 7.31 (d, 2H, C$_6$H$_4$).

Example 35

4'-tert-butoxycarbonyloxy-4-n-pentylbiphenyl
(Compound 35)

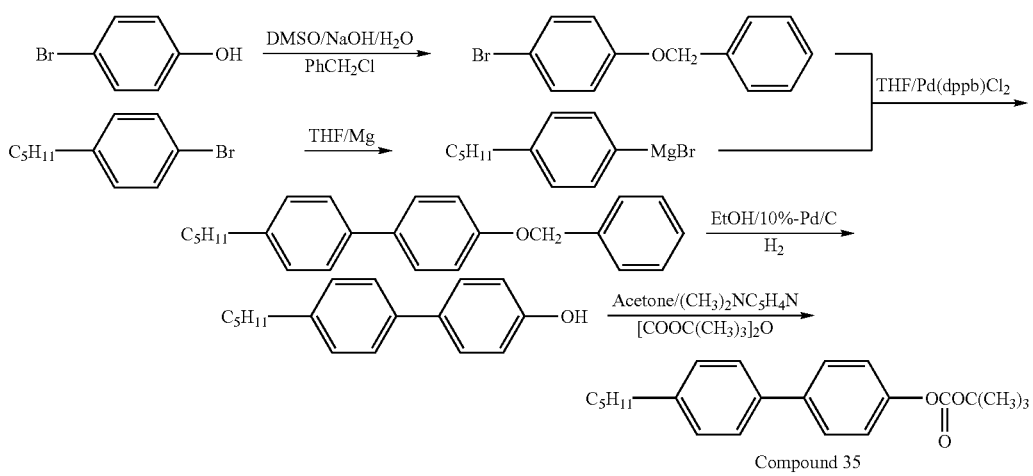

Compound 35

(i) Synthesis of 4-(benzyloxy)bromobenzene 4-(benzyloxy)bromobenzene was obtained in the same manner as in the step (i) of the Example 27, except for using 4-bromophenol and benzyl chloride instead of 4-(benzyloxy)phenol and n-propyl bromide, respectively.

(ii) Synthesis of 4-n-pentyl-4'-benzyloxybiphenyl

Magnesium (1.06 g: 88.3 mmol) and 4-n-pentylbromobenzene (10.0 g: 44.01 mmol) were dissolved in 50 ml of dried tetrahydrofuran, and a Grignard reagent was prepared from the mixture. To the Grignard reagent was added 11.6 g (44.1 mmol) of 4-(benzyloxy)bromobenzene synthesized in the step (i). The reaction system was purged with argon. To the reaction system was added 600 mg of dichloro(1,4-diphenylphosphinobutane)palladium (II) [Pd(dppb)Cl$_2$], and the reaction was conducted for 24 hours. The reaction mixture was poured into an iced water, and the resultant mixture was acidified by adding hydrochloric acid. The resultant solid was collected by filtration, washed with water, dried, and recrystallized from a mixed solvent of hexane/toluene to give 9.0 g (27.3 mmol) of 4-n-pentyl-4'-benzyloxybiphenyl.

(iii) Synthesis of 4-n-pentyl-4'-hydroxybiphenyl 4-n-pentyl-4'-hydroxybiphenyl was obtained by conducting hydrogenolysis in the same manner as in the step (ii) of the Example 24, except for using 4-n-pentyl-4'-benzyloxybiphenyl synthesized in the step (ii) instead of 1-(tert-butoxycarbonyloxy)-4-benzyloxybenzene, and using toluene as the recrystallization solvent.

(iv) Synthesis of 4'-tert-butoxycarbonyloxy-4-n-pentylbiphenyl

4'-tert-butoxycarbonyloxy-4-n-pentylbiphenyl was obtained in the same manner as in the Example 2, except for using 4-n-pentyl-4'-hydroxybiphenyl obtained in the step (iii) instead of 4-isopropylphenol.

$^1$H-NMR(CDCl$_3$) ppm: 0.93(t, 3H, CH$_3$), 1.30-1.43(m, 4H, CH$_2$), 1.55(s, 9H, tert-Bu), 1.55-1.75(m, 2H, CH$_2$), 2.65 (t, 2H, CH$_2$), 7.18-7.28(m, 4H, C$_6$H$_4$), 7.46(d, 2H, C$_6$H$_4$), 7.57(d, 2H, C$_6$H$_4$).

Example 36

Synthesis of 1-(tert-butoxycarbonyloxy)-4-phenylbenzene (Compound 36)

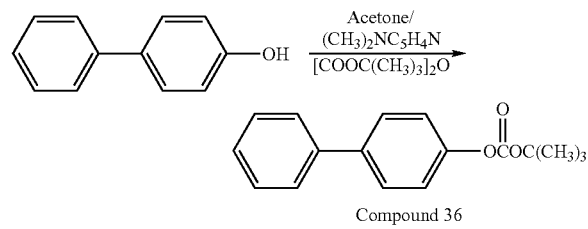

Compound 36

1-(tert-butoxycarbonyloxy)-4-phenylbenzene was obtained in the same manner as in the Example 2, except for using 4-phenylphenol and hexane as the recrystallization solvent in lieu of 4-isopropylphenol and methanol, respectively.

$^1$H-NMR(CDCl$_3$) ppm: 1.55(s, 18H, tert-Bu), 7.24(d, 2H, C$_6$H$_4$), 7.30-7.39(m, 1H, C$_6$H$_5$)7.39-7.49(m, 2H, C$_6$H$_5$ 7.52-7.63(m, 4H, C$_6$H$_4$ and C$_6$H$_5$).

Example 37

Synthesis of 4'-tert-butoxycarbonyloxy-4-n-propyloxybiphenyl (Compound 37)

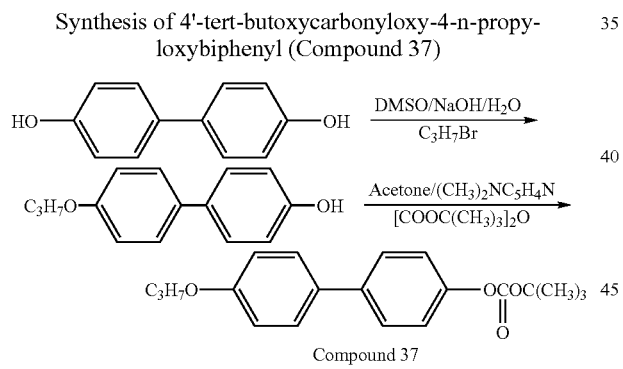

Compound 37

(i) Synthesis of 4-n-propyloxy-4'-hydroxybiphenyl 4-n-propyloxy-4'-hydroxybiphenyl was obtained in the same manner as in the step (i) of the Example 27, except for using 4,4'-biphenol and toluene as the recrystallization solvent instead of 4-(benzyloxy)phenol and methanol, respectively.

(ii) Synthesis of 4'-tert-butoxycarbonyloxy-4-n-propyloxybiphenyl

4'-tert-butoxycarbonyloxy-4-n-propyloxybiphenyl was obtained in the same manner as in the Example 2, except for using 4-n-propyloxy-4'-hydroxybiphenyl synthesized in step (i) and hexane as the recrystallization solvent in lieu of 4-isopropylphenol and methanol, respectively.

$^1$H-NMR(CDCl$_3$) ppm: 1.07(t, 3H, CH$_3$), 1.55(s, 9H, tert-Bu), 1.78-1.935(m, 2H, CH$_2$), 3.98(t, 2H, OCH$_2$), 6.96 (d, 2H, C$_6$H$_4$), 7.21 (d, 2H, C$_6$H$_4$), 7.47 (d, 2H, C$_6$H$_4$), 7.53(d, 2H, C$_6$H$_4$).

Example 38

Synthesis of 1-[4-(tert-butoxycarbonyloxy)phenyl]-2-phenylacetylene (Compound 38)

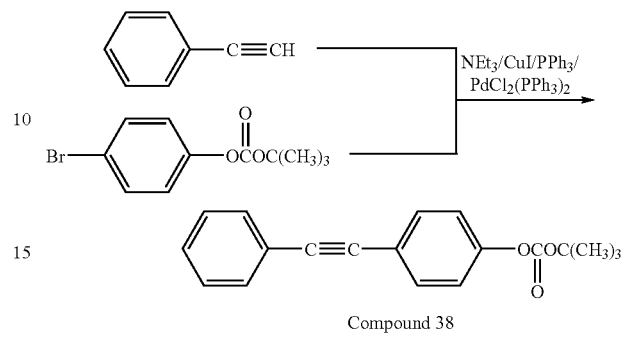

Compound 38

1-[4-(tert-butoxycarbonyloxy)phenyl]-2-phenylacetylene was obtained in the same manner as in the step (iii) of the Example 31, except for using phenylacetylene instead of 4-n-propylphenylacetylene.

$^1$H-NMR(CDCl$_3$) ppm: 1.55(s, 9H, tert-Bu), 7.16(d, 2H, C$_6$H$_4$), 7.30-7.38(m, 3H, C$_6$H$_5$), 7.49-7.57(m, 4H, C$_6$H$_4$ and C$_6$H$_5$).

Example 39

Synthesis of 1-(tert-butoxycarbonyloxy)naphthalene (Compound 39)

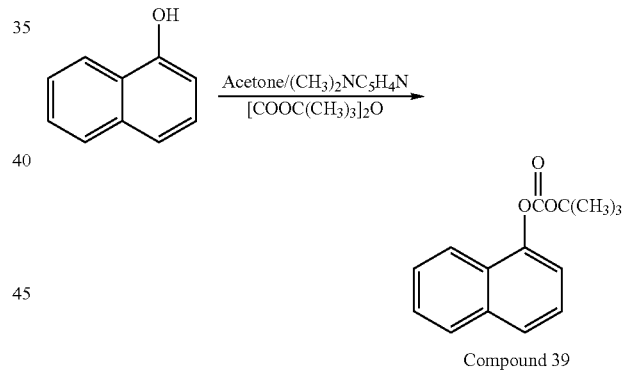

Compound 39

1-(tert-butoxycarbonyloxy)naphthalene was obtained in the same manner as in the Example 3, except for using 1-naphthol instead of 4-tert-butylphenol.

1H-NMR(CDCl$_3$) ppm: 1.58(s, 18H, tert-Bu), 7.32(q, 1H, C$_{10}$H$_7$), 7.42-7.58(m, 3H, C$_{10}$H$_7$), 7.74(d, 1H, C$_{10}$H$_7$), 7.81-8.00(m, 2H, C$_{10}$H$_7$).

Example 40

Synthesis of 2-(tert-butoxycarbonyloxy)naphthalene (Compound 40)

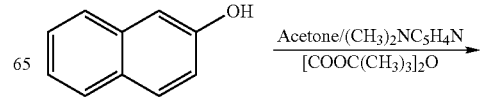

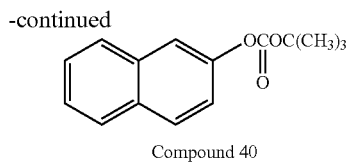

Compound 40

2-(tert-butoxycarbonyloxy)naphthalene was obtained by in the same manner as in the Example 2, except for using 2-naphthol and hexane as the recrystallization solvent in lieu of 4-isopropylphenol and methanol, respectively.

$^1$H-NMR(CDCl$_3$) ppm: 1.58(s, 18H, tert-Bu), 7.31(q, 1H, C$_{10}$H$_7$), 7.41-7.52(m, 2H, C$_{10}$H$_7$), 7.64(d, 1H, C$_{10}$H$_7$), 7.77-7.88(m, 3H, C$_{10}$H$_7$).

Example 41

Synthesis of 6-(tert-butoxycarbonyloxy)-2-n-pentylnaphthalene (Compound 41)

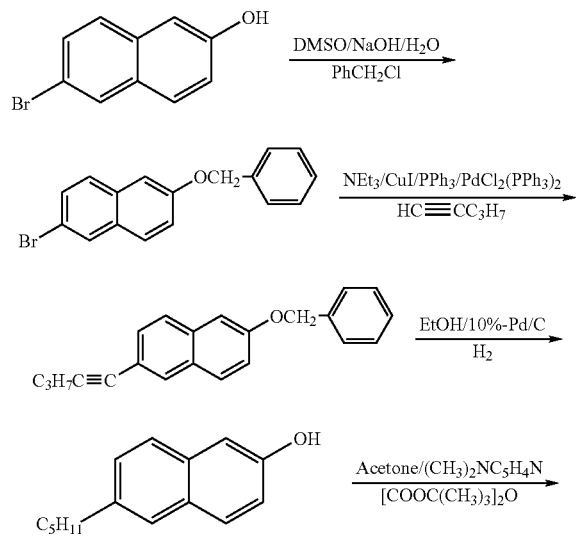

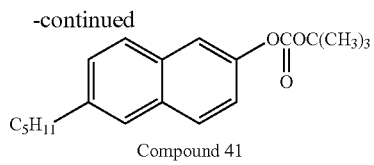

Compound 41

(i) Synthesis of 2-(benzyloxy)-6-bromonaphthalene 2-(benzyloxy)-6-bromonaphthalene was obtained in the same manner as in the step (i) of the Example 27, except for using 6-bromo-2-naphthol and benzyl chloride instead of 4-(benzyloxy)phenol and n-propyl bromide, respectively, and using ethanol as the recrystallization solvent.

(ii) Synthesis of 2-(benzyloxy)-6-(2-n-propylethynyl) naphthalene

The reaction was conducted in the same manner as in the step (i) of the Example 31, except for using 2-(benzyloxy)-6-bromonaphthalene synthesized in the step (i) and 1-n-pentyne instead of 1-bromo-4-n-propylbenzene and trimethylsilylacetylene, respectively. The resultant was recrystallized from ethanol to give 2-(benzyloxy)-6-(2-n-propylethynyl) naphthalene.

(iii) Synthesis of 6-n-pentyl-2-naphthol 6-n-pentyl-2-naphthol was obtained by conducting hydrogenolysis in the same manner as in the step (ii) of the Example 24, except for using 2-(benzyloxy)-6-(2-n-propylethynyl) naphthalene obtained in the step (ii) instead of 1-(tert-butoxycarbonyloxy)-4-benzyloxybenzene, and using hexane as the recrystallization solvent.

(iv) Synthesis of 6-(tert-butoxycarbonyloxy)-2-n-pentylnaphthalene 6-(tert-butoxycarbonyloxy)-2-n-pentylnaphthalene was obtained in the same manner as in the Example 2, except for using 6-n-pentyl-2-naphthol synthesized in the step (iii) instead of 4-isopropylphenol.

$^1$H-NMR(CDCl$_3$) ppm: 0.90(t, 3H, CH$_3$), 1.28-1.45(m, 4H, CH$_2$), 1.57(s, 9H, tert-Bu), 1.61-1.79(m, 2H, CH$_2$), 2.76 (t, 2H, CH$_2$), 7.24-7.37(m, 2H, C$_{10}$H$_6$), 7.59(d, 2H, C$_{10}$H$_6$), 7.68-7.80(q, 2H, C$_{10}$H$_6$).

Example 42

Synthesis of 4-(tert-butoxycarbonyloxy)-N-(4-ethylphenyl)carbamate (Compound 42)

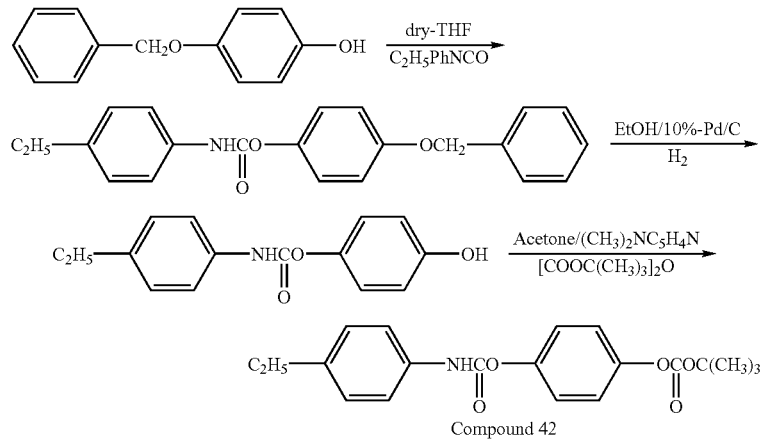

Compound 42

(i) Synthesis of 4-(benzyloxyphenyl)-N-(4-ethylphenyl)carbamate 6.8 g (34.0 mmol) of 4-(benzyloxy)phenol was added to 50 ml of dried tetrahydrofuran (dry-THF), and was homogeneously dissolved. Next 5.0 g (34.0 mmol) of ethylphenyl isocyanate ($C_2H_5PhNCO$) was added to the mixture, and the reaction was conducted for 24 hours. The reaction mixture was poured into 1 L of an iced water and a solid was formed by stirring. The resultant solid was collected by filtration, dried, and recrystallized from a methanol to give 11.3 g (32.6 mmol) of 4-(benzyloxyphenyl)-N-(4-ethylphenyl)carbamate.

(ii) Synthesis of 4-(hydroxyphenyl)-N-(4-ethylphenyl)carbamate 4-(hydroxyphenyl)-N-(4-ethylphenyl)carbamate was obtained by conducting hydrogenolysis in the same manner as in the step (ii) of the Example 24, except for using 4-(benzyloxyphenyl)-N-(4-ethylphenyl)carbamate synthesized in the step (i) in lieu of 1-(tert-butoxycarbonyloxy)-4-benzyloxybenzene, and using a mixed solvent of hexane/ethyl acetate as the recrystallization solvent.

(iii) Synthesis of 4-(tert-butoxycarbonyloxy)-N-(4-ethylphenyl)carbamate 4-(tert-butoxycarbonyloxy)-N-(4-ethylphenyl)carbamate was obtained in the same manner as in the Example 2, except for using 4-(hydroxyphenyl)-N-(4-ethylphenyl)carbamate synthesized in the step (ii) instead of 4-isopropylphenol.

$^1$H-NMR(CDCl$_3$) ppm: 1.24(t, 3H, CH$_3$), 1.55(s, 9H, tert-Bu), 2.63(q, 2H, CH$_2$), 6.87(s, 1H, NH), 7.14-7.21(m, 6H, C$_6$H$_4$), 7.35(d, 2H, C$_6$H$_4$).

Example 43

Synthesis of 4-(tert-butoxycarbonyloxy)-N-(4'-n-pentyl)benzanilide (Compound 43)

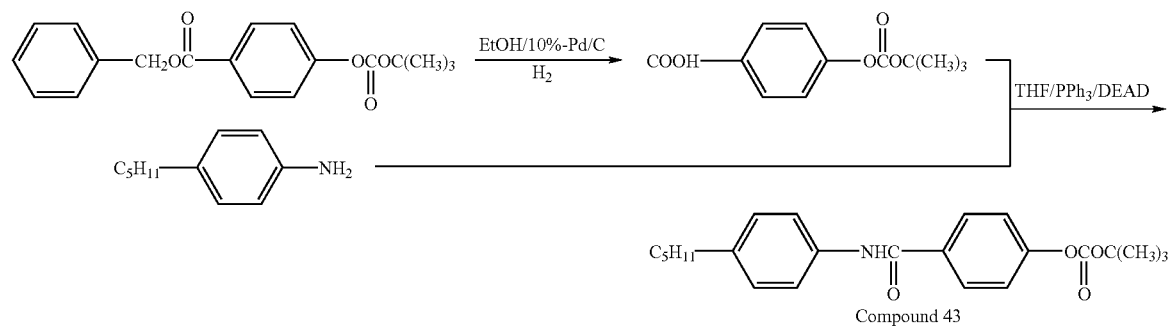

Compound 43

(i) Synthesis of 4-(tert-butoxycarbonyloxy)benzoic acid 4-(tert-butoxycarbonyloxy)benzoic acid was obtained by conducting hydrogenolysis in the same manner as in the step (ii) of the Example 24, except for using 4-benzyl 1-(tert-butoxycarbonyloxy)benzoate obtained in the example 5 instead of 1-(tert-butoxycarbonyloxy)-4-benzyloxybenzene.

(ii) 4-(tert-butoxycarbonyloxy)-N-(4'-n-pentyl)benzanilide 4-(tert-butoxycarbonyloxy)-N-(4'-n-pentyl)benzanilide was obtained in the same manner as in the step (iii) of the Example 24, except for using 4-(tert-butoxycarbonyloxy)benzoic acid obtained in the step (i) and 4-n-pentylaniline in lieu of 4-n-propyloxybenzoic acid and 4-(tert-butoxycarbonyloxy)phenol, respectively.

$^1$H-NMR(CDCl$_3$) ppm: 0.90(t, 3H, CH$_3$), 1.28-1.45(m, 4H, CH$_2$), 1.57(s, 9H, tert-Bu), 1.61-1.79(m, 2H, CH$_2$), 2.76 (t, 2H, CH$_2$), 7.10(d, 2H, C$_6$H$_4$), 7.23(d, 2H, C$_6$H$_4$), 7.33(d, 2H, C$_6$H$_4$), 8.24(d, 2H, C$_6$H$_4$).

Example 44

Synthesis of tert-butyl-4-(4'-tert-butoxycarbonyloxyphenyl)cinnamate (Compound 44)

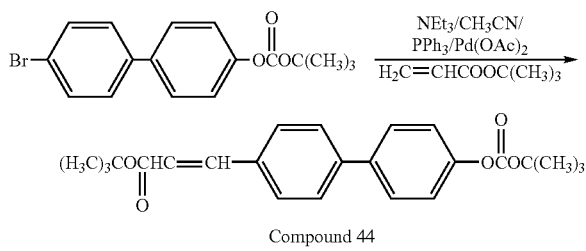

Compound 44

To 7.4 g (21.2 mmol) of 4-(tert-butoxycarbonyloxy)-4'-bromobiphenyl synthesized in the Example 9, were added 2.85 g (22.2 mmol) of tert-butyl acrylate, 10 ml of triethylamine, 30 ml of acetonitrile, 50 mg (2.22×10$^{-1}$ mmol) of palladium acetate [Pd(OAc)$_2$], and 116 mg (4.42×10$^{-1}$ mmol) triphenylphosphine. The reaction system was purged with argon, and the reaction was conducted for 24 hours with heating and refluxing. The reaction mixture was poured into 500 ml of an iced water, and hydrochloric acid was added to the resultant mixture with stirring. The solid formed by stirring was collected by filtration, washed with water, dried, and recrystallized from methanol to give 7.9 g (19.9 mmol) of tert-butyl-4-(4'-tert-butoxycarbonyloxyphenyl)cinnamate.

$^1$H-NMR(CDCl$_3$) ppm: 1.55(s, 18H, tert-Bu), 6.40(d, 1H, CH=CH), 7.26(d, 4H, C$_6$H$_4$), 7.59(d, 4H, C$_6$H$_4$), 7.61(d, 1H, CH=CH).

Example 45

Synthesis of 4'-(tert-butoxycarbonyloxy)-4-(2-tert-butoxycarbonylethyl)biphenyl (Compound 45)

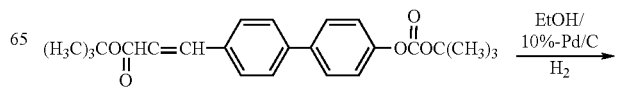

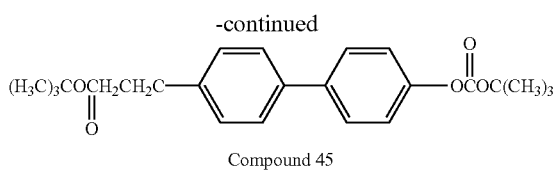

Compound 45

4'-(tert-butoxycarbonyloxy)-4-(2-tert-butoxycarbonylethyl)biphenyl was obtained in the same manner as in the step (ii) of the Example 24, except for using tert-butyl-4-(4'-tert-butoxycarbonyloxyphenyl)cinnamate synthesized in Example 44 instead of 1-(tert-butoxycarbonyloxy)-4-benzyloxybenzene, and using hexane as the recrystallization solvent.

Example 46

Synthesis of 2-(tert-butoxycarbonyloxy)-6-(2-tert-butoxycarbonylvinyl)naphthalene (Compound 46)

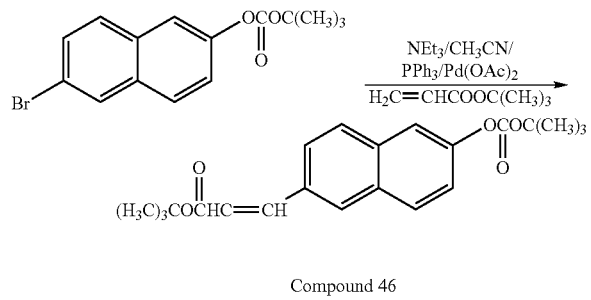

Compound 46

2-(tert-butoxycarbonyloxy)-6-(2-tert-butoxycarbonylvinyl)naphthalene was obtained in the same manner as in the Example 44, except for using 6-(tert-butoxycarbonyloxy)-2-bromonaphthalene obtained in the Example 12 and ethanol as the recrystallization solvent instead of 4-(tert-butoxycarbonyloxy)-4'-bromobiphenyl and methanol, respectively.

$^1$H-NMR(CDCl$_3$) ppm: 1.55(s, 18H, tert-Bu), 6.49(d, 1H, CH=CH), 7.34(d, 1H, C$_{10}$H$_6$), 7.60-7.91(m, 6H, C$_{10}$H$_6$ and CH=CH).

Example 47

Synthesis of 2-(tert-butoxycarbonyloxy)-6-(2-tert-butoxycarbonylethyl)naphthalene (Compound 47)

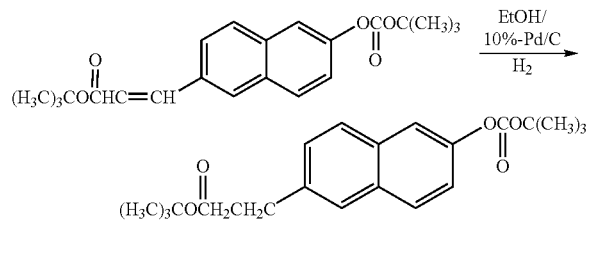

Compound 47

2-(tert-butoxycarbonyloxy)-6-(2-tert-butoxycarbonylethyl)naphthalene was obtained by hydrogenolysis in the same manner as in the step (ii) of the Example 24, except for using 2-(tert-butoxycarbonyloxy)-6-(2-tert-butoxycarbonylvinyl)naphthalene synthesized in the Example 46 instead of 1-(tert-butoxycarbonyloxy)-4-benzyloxybenzene, and using hexane as the recrystallization solvent.

Example 48

Synthesis of 4'-(tert-butoxycarbonyloxy)-4-(2-trimethylsilylethynyl)biphenyl (Compound 48)

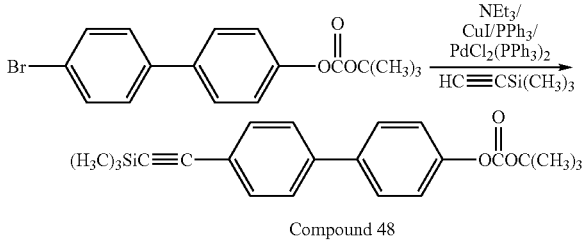

Compound 48

The reaction was conducted in the same manner as in the step (i) of the Example 31, except for using 4-(tert-butoxycarbonyloxy)-4'-bromobiphenyl synthesized in the Example 9 instead of 1-bromo-4-n-propylbenzene, and the resultant was recrystallized from methanol to give 4'-(tert-butoxycarbonyloxy)-4-(2-trimethylsilylethynyl)biphenyl.

$^1$H-NMR(CDCl$_3$) ppm: 0.28(s, 9H, Si(CH$_3$)$_3$), 1.55(s, 9H, tert-Bu), 7.24(d, 2H, C$_6$H$_4$), 7.47-7.60(m, 6H, C$_6$H$_4$).

Example 49

Synthesis of 4'-(tert-butoxycarbonyloxy)-4-(2-trimethylsilylvinyl)biphenyl (Compound 49)

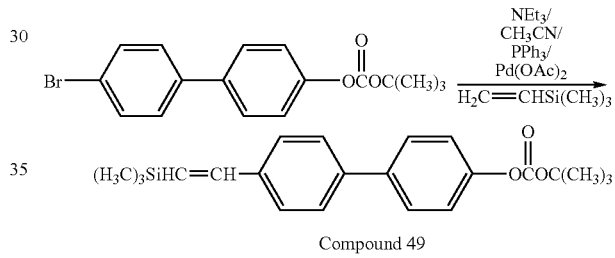

Compound 49

4'-(tert-butoxycarbonyloxy)-4-(2-trimethylsilylvinyl)biphenyl was obtained in the same manner as the Example 44, except for using vinyltrimethylsilane in lieu of tert-butyl acrylate.

Example 50

Synthesis of 6-(tert-butoxycarbonyloxy)-2-(2-trimethylsilylethynyl)naphthalene (Compound 50)

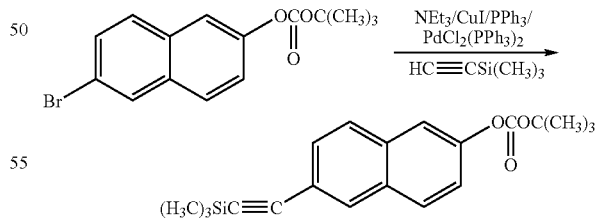

Compound 50

The reaction was conducted in the same manner as in the step (i) of the Example 31, except for using 6-(tert-butoxycarbonyloxy)-2-bromonaphthalene synthesized in the Example 12 instead of 1-bromo-4-n-propylbenzene, and the resultant was recrystallized from methanol to give 6-(tert-butoxycarbonyloxy)-2-(2-trimethylsilylethynyl)naphthalene.

$^1$H-NMR(CDCl$_3$) ppm: 0.29(s, 9H, Si(CH$_3$)$_3$), 1.57(s, 9H, tert-Bu), 7.31(d, 1H, C$_{10}$H$_6$), 7.51(d, 1H, C$_{10}$H$_6$), 7.60(d, 1H, C$_{10}$H$_6$) 7.75(q, 2H, C$_{10}$H$_6$), 7.79(s, 1H, C$_{10}$H$_6$).

Example 51

Synthesis of 6-(tert-butoxycarbonyloxy)-2-(2-trimethylsilylvinyl)naphthalene (Compound 51)

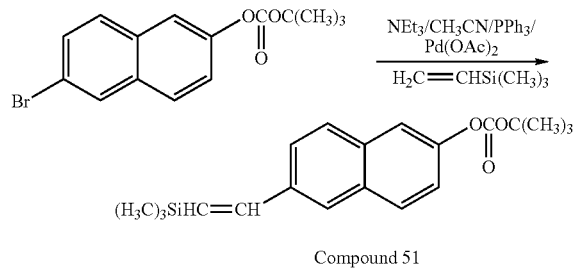

Compound 51

6-(tert-butoxycarbonyloxy)-2-(2-trimethylsilylvinyl)naphthalene was obtained in the same manner as in the Example 44, except for using vinyltrimethylsilane in lieu of tert-butyl acrylate.

$^1$H-NMR(CDCl$_3$) ppm: 0.29(s, 9H, Si(CH$_3$)$_3$), 1.58(s, 18H, tert-Bu), 6.60(d, 1H, CH=CH), 7.02(d, 1H, CH=CH), 7.29(d, 1H, C$_{10}$H$_6$), 7.56-7.87(m, 5H, C$_{10}$H$_6$).

Example 52

Synthesis of 4-(tert-butoxycarbonyloxy)phenyl-4-(2-trimethylsilylethynyl)benzyl ether (Compound 52)

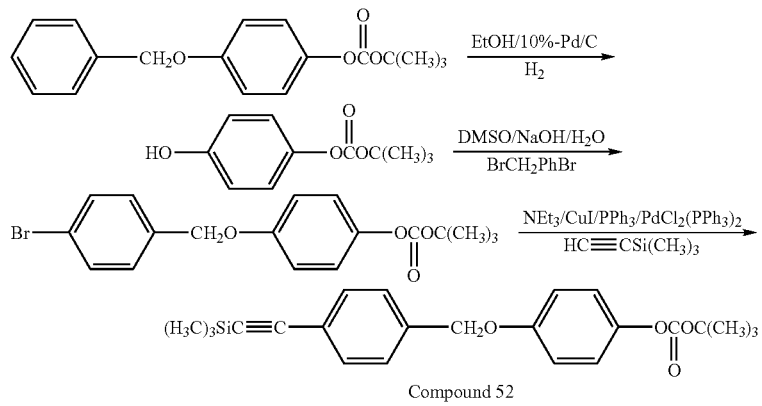

Compound 52

(i) Synthesis of 4'-(tert-butoxycarbonyloxy)phenyl-4-bromobenzyl ether

4'-(tert-butoxycarbonyloxy)phenyl-4-bromobenzyl ether was obtained in the same manner as in the step (i) of the Example 27, except for using 4-(tert-butoxycarbonyloxy)phenol synthesized in the step (ii) of the Example 24 and p-bromobenzyl bromide instead of 4-(benzyloxy)phenol and n-propylbromide, respectively.

(ii) Synthesis of 4-(tert-butoxycarbonyloxy)phenyl-4-(2-trimethylsilylethynyl)benzyl ether The reaction was conducted in the same manner as in the step (i) of the Example 31, except for using 4'-(tert-butoxycarbonyloxy)phenyl-4-bromobenzyl ether synthesized in the step (i) instead of 1-bromo-4-n-propylbenzene, and the resultant was recrystallized from hexane to give 4-(tert-butoxycarbonyloxy)phenyl-4-(2-trimethylsilylethynyl)benzyl ether.

$^1$H-NMR(CDCl$_3$) ppm: 0.27(s, 9H, Si(CH$_3$)$_3$), 1.55(s, 9H, tert-Bu), 5.04(s, 2H, OCH$_2$), 6.92(d, 2H, C$_6$H$_4$), 7.08(d, 2H, C$_6$H$_4$), 7.34(d, 2H, C$_6$H$_4$), 7.48(d, 2H, C$_6$H$_4$).

Example 53

Synthesis of 4-(tert-butoxycarbonyloxy)phenyl-4-(2-trimethylsilylvinyl)benzyl ether (Compound 53)

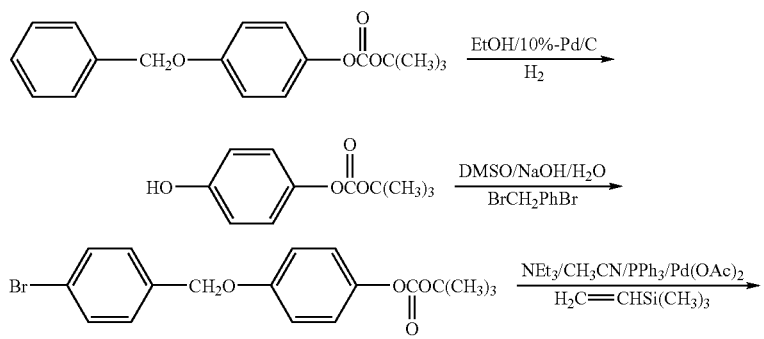

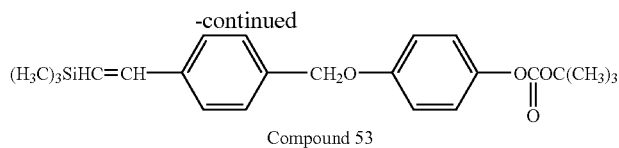

Compound 53

4-(tert-butoxycarbonyloxy)phenyl-4-(2-trimethylsilylvinyl)benzyl ether was obtained in the same manner as in the Example 44, except for using 4'-(tert-butoxycarbonyloxy)phenyl-4-bromobenzyl ether synthesized in the step (i) of the Example 52 and vinyltrimethylsilane instead of 4-(tert-butoxycarbonyloxy)-4'-bromobiphenyl and tert-butyl acrylate, respectively.

$^1$H-NMR(CDCl$_3$) ppm: 0.17(s, 9H, Si(CH$_3$)$_3$), 1.55(s, 18H, tert-Bu), 5.05(s, 2H, OCH$_2$), 6.48(d, 1H, CH=CH), 6.87(d, 1H, CH=CH), 6.93(d, 2H, C$_6$H$_4$), 7.07(d, 2H, C$_6$H$_4$), 7.32-7.49(m, 4H, C$_6$H$_4$).

Example 54

Synthesis of 1-(1-ethoxy)ethoxy-4-(tert-butyl)benzene (Compound 54)

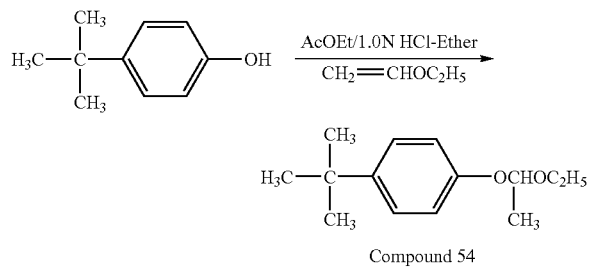

Compound 54

1-(1-ethoxy)ethoxy-4-(tert-butyl)benzene was obtained in the same manner as in the Example 1, except for using 4-t-butylphenol instead of 4-isopropylphenol.

$^1$H-NMR(CDCl$_3$) ppm: 1.24(t, 3H, terminal CH$_3$), 1.30(s, 9H, tert-Bu), 1.49(d, 3H, branched CH$_3$), 3.49-3.63(m, 1H, OCH$_2$), 3.74-3.89(m, 1H, OCH$_2$), 5.35(q, 1H, terminal OCH), 6.92(d, 2H, C$_6$H$_4$), 7.28(d, 2H, C$_6$H$_4$).

Example 55

Synthesis of 1-(1-ethoxy)ethoxy-4-bromobenzene (Compound 55)

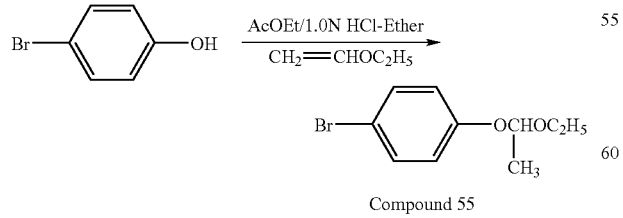

Compound 55

1-(1-ethoxy)ethoxy-4-bromobenzene was obtained in the same manner as in the Example 1, except for using 4-bromophenol in lieu of 4-isopropylphenol.

$^1$H-NMR(CDCl$_3$) ppm: 1.19(t, 3H, terminal CH$_3$), 1.49(d, 3H, branched CH$_3$), 3.49-3.62(m, 1H, OCH$_2$), 3.70-3.85(m, 1H, OCH$_2$), 5.36(q, 1H, branched OCH), 6.89(d, 2H, C$_6$H$_4$), 7.37(d, 2H, C$_6$H$_4$).

Example 56

Synthesis of 1-(1-ethoxy)ethoxy-4-benzoic acid benzylester (Compound 56)

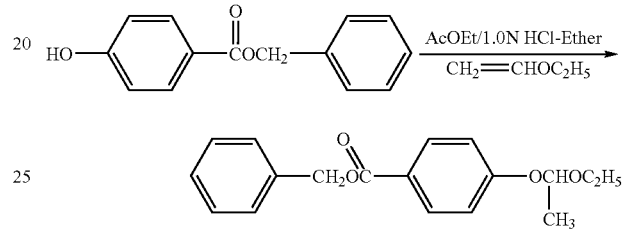

Compound 56

1-(1-ethoxy)ethoxy-4-benzoic acid benzylester was obtained in the same manner as in the Example 1, except for using 4-hydroxybenzoic acid benzyl ester in lieu of 4-isopropylphenol.

$^1$H-NMR(CDCl$_3$) ppm: 1.19(t, 3H, terminal CH$_3$), 1.53(d, 3H, branched CH$_3$), 3.45-3.60(m, 1H, OCH$_2$), 3.69-3.82(m, 1H, OCH$_2$), 5.35(s, 2H, OCH$_2$), 5.49(q, 1H, branched OCH), 7.02(d, 2H, C$_6$H$_4$), 7.29-7.49(m, 5H, C$_6$H$_5$), 8.02(d, 2H, C$_6$H$_4$).

Example 57

Synthesis of 1,4-di[(1-ethoxy)ethoxy]benzene (Compound 57)

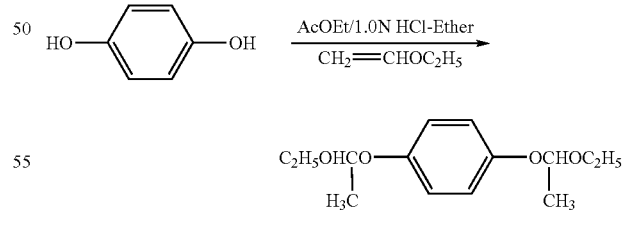

Compound 57

1,4-di[(1-ethoxy)ethoxy]benzene was obtained in the same manner as in the Example 1, except for using hydroquinone instead of 4-isopropylphenol.

$^1$H-NMR(CDCl$_3$) ppm: 1.20(t, 6H, terminal CH$_3$), 1.48(d, 6H, branched CH$_3$), 3.49-3.62(m, 2H, OCH$_2$), 3.73-3.90(m, 2H, OCH$_2$), 5.28(q, 2H, branched OCH), 6.93(s, 4H, C$_6$H$_4$).

Example 58

Synthesis of 4,4'-di[(1-ethoxy)ethoxy]biphenyl (Compound 58)

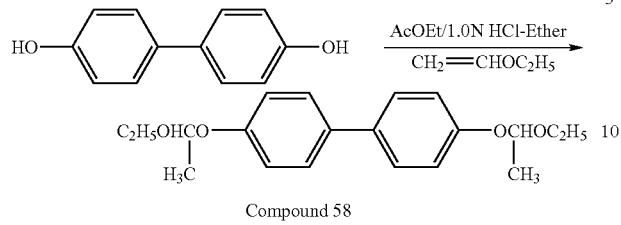

Compound 58

4,4'-di[(1-ethoxy)ethoxy]biphenyl was obtained in the same manner as in the Example 1, except for using 4,4'-biphenol instead of 4-isopropylphenol.

$^1$H-NMR(CDCl$_3$) ppm: 1.21(t, 6H, terminal CH$_3$), 1.53(d, 6H, branched CH$_3$), 3.50-3.69(m, 2H, OCH$_2$), 3.76-3.91(m, 2H, OCH$_2$), 5.42(q, 2H, branched OCH), 7.04(d, 4H, C$_6$H$_4$), 7.46(d, 4H, C$_6$H$_4$).

Example 59

Synthesis of 1-(1-ethoxy)ethoxy-4-benzoic acid phenyl ester (Compound 59)

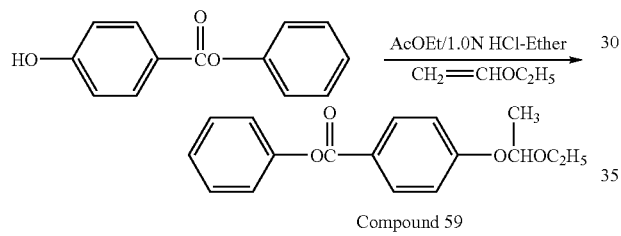

Compound 59

1-(1-ethoxy)ethoxy-4-benzoic acid phenyl ester was obtained in the same manner as in the Example 1, except for using 4-hydroxybenzoic acid phenyl ester instead of 4-isopropylphenol.

$^1$H-NMR(CDCl$_3$) ppm: 1.20(t, 3H, terminal CH$_3$), 1.56(d, 3H, branched CH$_3$), 3.49-3.67(m, 1H, OCH$_2$), 3.70-3.89(m, 1H, OCH$_2$), 5.52(q, 1H, branched OCH), 7.08(d, 2H, C$_6$H$_4$), 7.14-7.32(m, 3H, C$_6$H$_5$), 7.42(t, 2H, C$_6$H$_4$), 8.15(d, 2H, C$_6$H$_5$).

Example 60

Synthesis of 4-(1-ethoxy)ethoxy-4'-bromobiphenyl (Compound 60)

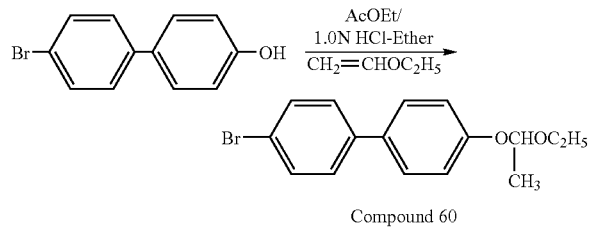

Compound 60

4-(1-ethoxy)ethoxy-4'-bromobiphenyl was obtained in the same manner as in the Example 1, except for using 4-bromo-4'-hydroxybiphenyl in lieu of 4-isopropylphenol.

$^1$H-NMR(CDCl$_3$) ppm: 1.20(t, 3H, terminal CH$_3$), 1.48(d, 3H, branched CH$_3$), 3.49-3.62(m, 1H, OCH$_2$), 3.73-3.90(m, 1H, OCH$_2$), 5.28(q, 1H, branched OCH), 7.25(d, 2H, C$_6$H$_4$), 7.43(d, 2H, C$_6$H$_4$), 7.50-7.60(m, 4H, C$_6$H$_4$).

Example 61

Synthesis of 2,6-di[(1-ethoxy)ethoxy]naphthalene (Compound 61)

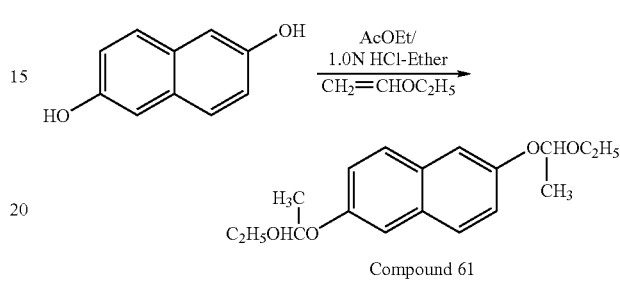

Compound 61

2,6-di[(1-ethoxy)ethoxy]naphthalene was obtained in the same manner as in the Example 1, except for using 2,6-dihydroxynaphthalene instead of 4-isopropylphenol.

$^1$H-NMR(CDCl$_3$) ppm: 1.21(t, 6H, terminal CH$_3$), 1.63(d, 6H, branched CH$_3$), 3.49-3.68(m, 2H, OCH$_2$), 3.78-3.93(m, 2H, OCH$_2$), 5.60(q, 2H, branched OCH), 7.35(d, 2H, C$_{10}$H$_6$), 7.67(d, 2H, C$_{10}$H$_6$), 7.83(d, 2H, C$_{10}$H$_6$).

Example 62

Synthesis of 1,5-di[(1-ethoxy)ethoxy]naphthalene (Compound 62)

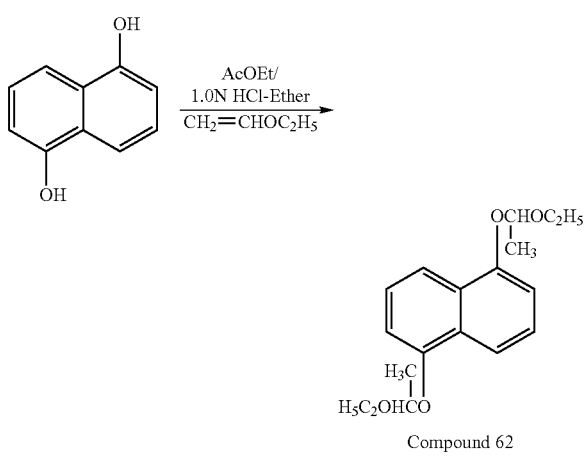

Compound 62

1,5-di[(1-ethoxy)ethoxy]naphthalene was obtained in the same manner as in the Example 1, except for using 1,5-dihydroxynaphthalene in lieu of 4-isopropylphenol.

$^1$H-NMR(CDCl$_3$) ppm: 1.21(t, 6H, terminal CH$_3$), 1.63(d, 6H, branched CH$_3$), 3.49-3.68(m, 2H, OCH$_2$), 3.78-3.93(m, 2H, OCH$_2$), 5.60(q, 2H, branched OCH), 7.03(d, 2H, C$_{10}$H$_6$), 7.37(t, 2H, C$_{10}$H$_6$), 7.92(d, 2H, C$_{10}$H$_6$).

Example 63

Synthesis of 2-[(1-ethoxy)ethoxy]-6-bromonaphthalene (Compound 63)

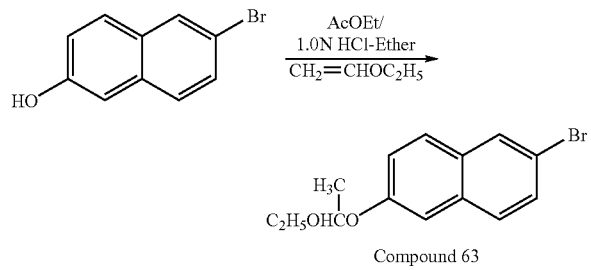

Compound 63

2-[(1-ethoxy)ethoxy]-6-bromonaphthalene was obtained in the same manner as in the Example 1, except for using 6-bromo-2-naphthol instead of 4-isopropylphenol.

$^1$H-NMR(CDCl$_3$) ppm: 1.20(t, 3H, terminal CH$_3$), 1.57(d, 3H, branched CH$_3$), 3.50-3.69(m, 1H, OCH$_2$), 3.73-3.90(m, 1H, OCH$_2$), 5.55(q, 1H, branched OCH), 7.18-7.32(m, 2H, C$_{10}$H$_6$), 7.49(d, 1H, C$_{10}$H$_6$), 7.55-7.70(q, 2H, C$_{10}$H$_6$), 7.92(d, 1H, C$_{10}$H$_6$).

Example 64

Synthesis of 1-[(1-ethoxy)ethoxy]-4-benzyloxybenzene (Compound 64)

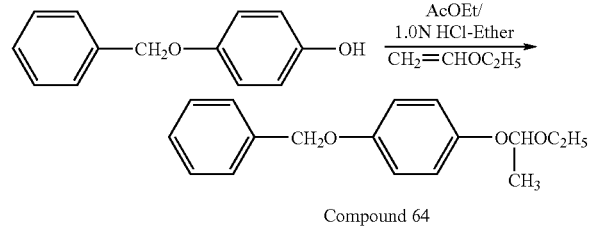

Compound 64

1-[(1-ethoxy)ethoxy]-4-benzyloxybenzene was obtained in the same manner as in the Example 1, except for using 4-(benzyloxy)phenol and toluene as the eluent of the silica gel column chromatography instead of 4-isopropylphenol and hexane, respectively.

$^1$H-NMR(CDCl$_3$) ppm: 1.20(t, 3H, terminal CH$_3$), 1.46(d, 3H, branched CH$_3$), 3.48-3.63(m, 1H, OCH$_2$), 3.72-3.90(m, 1H, OCH$_2$), 5.01(s, 2H, OCH$_2$), 5.26(q, 1H, branched OCH), 6.85-6.98(m, 4H, C$_6$H$_4$ and C$_6$H$_5$), 7.28-7.46(m, 5H, C$_6$H$_4$ and C$_6$H$_5$).

Example 65

Synthesis of 1-[(1-ethoxy)ethoxy]-4-(trans-4'-n-propylcyclohexyl)benzene (Compound 65)

-continued

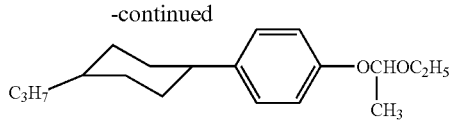

Compound 65

1-[(1-ethoxy)ethoxy]-4-(trans-4'-n-propylcyclohexyl)benzene was obtained in the same manner as in the Example 1, except for using p-(trans-4'-n-propylcyclohexyl)phenol instead of 4-isopropylphenol.

$^1$H-NMR(CDCl$_3$) ppm: 0.90(t, 3H, CH$_3$), 0.95-1.52(m, 9H, C$_2$H$_4$ and C$_6$H$_{10}$), 1.20(t, 3H, terminal CH$_3$), 1.49(d, 3H, branched CH$_3$), 1.79-1.94(m, 4H, C$_6$H$_{10}$), 2.35-2.50(m, 1H, C$_6$H$_{10}$), 3.49-3.62(m, 1H, OCH$_2$), 3.72-3.90(m, 1H, OCH$_2$), 5.33(q, 1H, branched OCH), 6.91(d, 2H, C$_6$H$_4$), 7.11(d, 2H, C$_6$H$_4$).

Example 66

Synthesis of 2,2-bis{4-[(1-ethoxy)ethoxy]phenyl}propane (Compound 66)

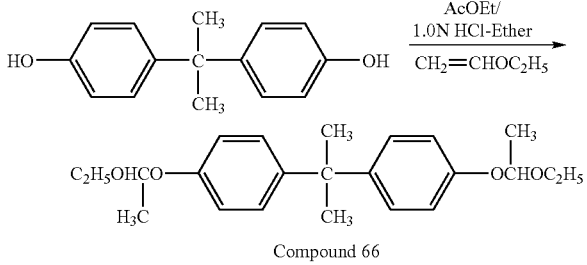

Compound 66

2,2-bis{4-[(1-ethoxy)ethoxy]phenyl}propane was obtained in the same manner as in the Example 1, except for using bisphenol A instead of 4-isopropylphenol.

$^1$H-NMR(CDCl$_3$) ppm: 1.20(t, 6H, terminal CH$_3$), 1.48(d, 6H, branchedCH$_3$), 1.63(s, 6H, CH$_3$), 3.47-3.62(m, 2H, OCH$_2$), 3.72-3.89(m, 2H, OCH$_2$), 5.35(q, 2H, branched OCH), 6.88(d, 4H, C$_6$H$_4$), 7.13(d, 4H, C$_6$H$_4$).

Example 67

Synthesis of 1,4-di[(1-ethoxy)ethoxy]-2,3,5,6-tetrafluorobenzene (Compound 67)

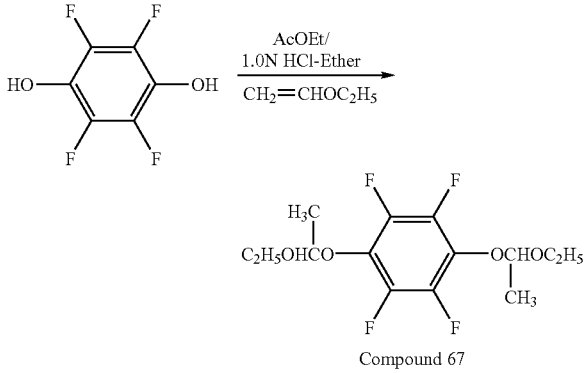

Compound 67

1,4-di[(1-ethoxy)ethoxy]-2,3,5,6-tetrafluorobenzene was obtained in the same manner as in the Example 1, except for using 2,3,5,6-(tetrafluoro)hydroquinone instead of 4-isopropylphenol.

$^1$H-NMR(CDCl$_3$) ppm: 1.21(t, 6H, terminal CH$_3$), 1.50(d, 6H, branched CH$_3$), 3.60-3.78(m, 2H, OCH$_2$), 3.88-4.03(m, 2H, OCH$_2$), 5.30(s, 2H, OCH$_2$).

Example 68

Synthesis of 2,2-bis{4-[(1-ethoxy)ethoxy]phenyl}hexafluoropropane (Compound 68)

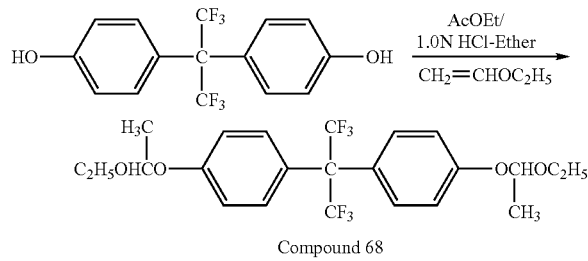

Compound 68

2,2-bis{4-[(1-ethoxy)ethoxy]phenyl}hexafluoropropane was obtained in the same manner as in the Example 1, except for using 2,2-bis(4-hydroxyphenyl)hexafluoropropane in lieu of 4-isopropylphenol.

$^1$H-NMR(CDCl$_3$) ppm: 1.25(t, 6H, terminal CH$_3$), 1.52(d, 6H, branched CH$_3$), 3.50-3.65(m, 2H, OCH$_2$), 3.71-3.88(m, 2H, OCH$_2$), 5.42(q, 2H, branched OCH), 6.96(d, 4H, C$_6$H$_4$), 7.29(d, 4H, C$_6$H$_4$).

Example 69

Synthesis of bis[4-(1-ethoxy)ethoxyphenyl]sulfone (Compound 69)

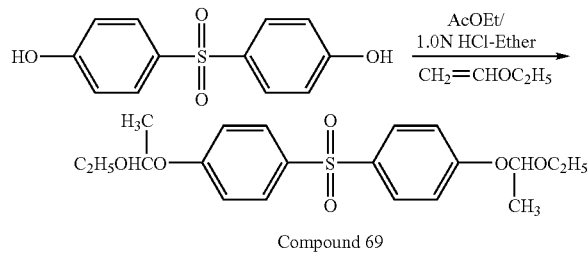

Compound 69

Bis[4-(1-ethoxy)ethoxyphenyl]sulfone was 5 obtained in the same manner as in the Example 1, except for using bis(4-hydroxyphenyl) sulfone and toluene as the eluent of the silica gel column chromatography instead of 4-isopropylphenol and hexane, respectively.

$^1$H-NMR(CDCl$_3$) ppm: 1.19(t, 6H, terminal CH$_3$), 1.50(d, 6H, branched CH$_3$), 3.42-3.60(m, 2H, OCH$_2$), 3.67-3.80(m, 2H, OCH$_2$), 5.45(q, 2H, branched OCH), 7.05(d, 4H, C$_6$H$_4$), 7.84(d, 4H, C$_6$H$_4$).

Example 70

Synthesis of 9,9-bis{4-[(1-ethoxy)ethoxy]phenyl}fluorene (Compound 70)

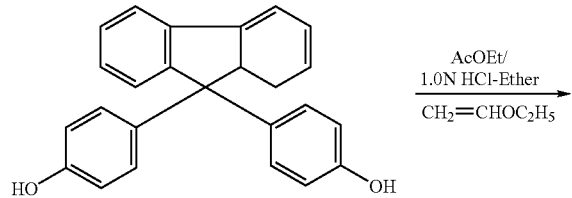

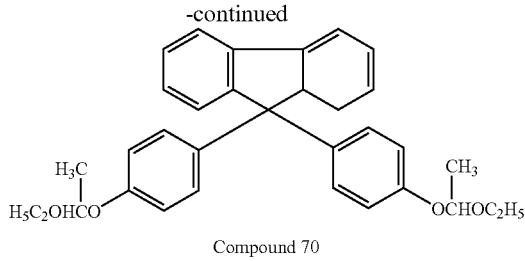

Compound 70

9,9-bis{4-[(1-ethoxy)ethoxy]phenyl}fluorene was obtained in the same manner as in the Example 1, except for using 9,9-bis(4-hydroxyphenyl)fluorene and toluene as the eluent of the silica gel column chromatography in lieu of 4-isopropylphenol and hexane, respectively.

$^1$H-NMR(CDCl$_3$) ppm: 1.19(t, 6H, terminal CH$_3$), 1.47(d, 6H, branched CH$_3$), 3.42-3.59(m, 2H, OCH$_2$), 3.70-3.84(m, 2H, OCH$_2$), 5.30(q, 2H, branched OCH), 6.82(d, 4H, C$_6$H$_4$), 7.09(d, 4H, C$_6$H$_4$), 7.21-7.41(m, 6H, C$_{13}$H$_8$), 7.75(d, 2H, C$_{13}$H$_8$).

Example 71

Synthesis of 1,4-bis {4-[(1-ethoxy)ethoxy]phenyl} cyclohexane (Compound 71)

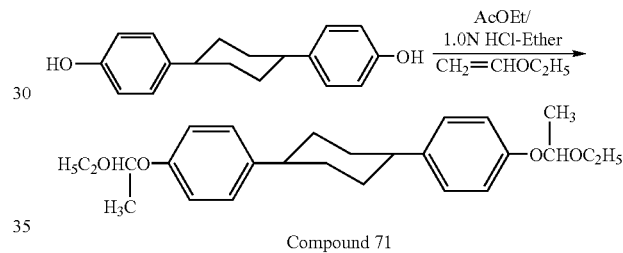

Compound 71

4,4'-cyclohexylidene-bis{1,1'-[(1-ethoxy)ethoxy]phenyl} was obtained in the same manner as in the Example 1, except for using 4,4'-cyclohexylidenebisphenol instead of 4-isopropylphenol.

$^1$H-NMR(CDCl$_3$) ppm: 1.21(t, 6H, terminal CH$_3$), 1.20-1.39(m, 2H, C$_6$H$_{10}$), 1.49(d, 6H, branched CH$_3$), 1.40-1.67 (m, 4H, C$_6$H$_{10}$), 2.19-2.30(m, 4H, C$_6$H$_{10}$), 3.48-3.62(m, 2H, OCH$_2$), 3.70-3.89(m, 2H, OCH$_2$), 5.33(q, 2H, branched OCH), 6.88(d, 4H, C$_6$H$_4$), 7.15(d, 4H, C$_6$H$_4$).

Example 72

Synthesis of 1,3-bis {2-{4-[(1-ethoxy)ethoxy]phenyl}}benzene (Compound 72)

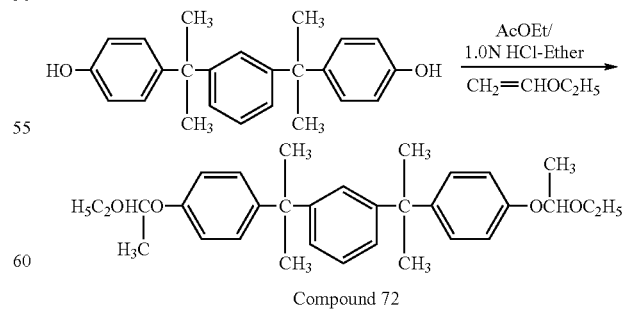

Compound 72

1,4-bis {4-[(1-ethoxy)ethoxy[phenyl}} cyclohexane was obtained in the same manner as in the Example 1, except for using 4,4'-cyclohexylidenebisphenol in lieu of 4-isopropyiphenol.

$^1$H-NMR(CDCl$_3$) ppm: 1.20(t, 6H, terminal CH$_3$), 1.49(d, 6H, branched CH$_3$), 1.61(s, 12H, CH$_3$), 3.48-3.63(m, 2H, OCH$_2$), 3.70-3.89(m, 2H, OCH$_2$), 5.35(q, 2H, branched OCH), 6.86(d, 4H, C$_6$H$_4$), 6.97-7.20(m, 8H, C$_6$H$_4$).

Example 73

Synthesis of 1-[(1-ethoxy)ethoxy]-4-(trans-4'-n-pentylcyclohexyl)benzene (Compound 73)

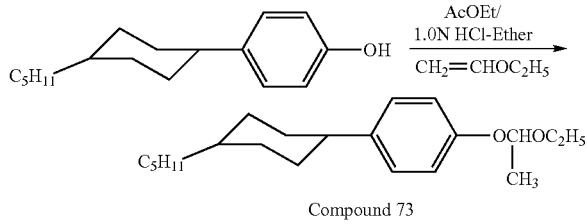

Compound 73

1-[(1-ethoxy)ethoxy]-4-(trans-4'-n-pentylcyclohexyl)benzene was obtained in the same manner as in the Example 1, except for using p-(trans-4-n-pentylcyclohexyl)phenol instead of 4-isopropylphenol.

$^1$H-NMR(CDCl$_3$) ppm: 0.90(t, 3H, CH$_3$), 1.20(t, 3H, terminal CH$_3$), 0.95-1.50(m, 13H, C$_4$H$_8$ and C$_6$H$_{10}$), 1.49(d, 3H, branched CH$_3$), 1.79-1.94(m, 4H, C$_6$H$_{10}$), 2.32-2.49(m, 1H, C$_6$H$_{10}$), 3.48-3.62(m, 1H, OCH$_2$), 3.71-3.89(m, 1H, OCH$_2$), 5.35(q, 1H, branched OCH), 6.91(d, 2H, C$_6$H$_4$), 7.11(d, 2H, C$_6$H$_4$).

Example 74

Synthesis of 4-[(1-ethoxy)ethoxyphenyl]-4'-(n-propyloxy)benzoate (Compound 74)

(i) Synthesis of 4-benzyloxyphenyl-4'-(n-propyloxy)benzoate 4-benzyloxyphenyl-4'-(n-propyloxy)benzoate was obtained in the same manner as in the step (iii) of the Example 24, except for using 4-(benzyloxy)phenol and ethanol as the recrystallization solvent in lieu of 4-(tert-butoxycarbonyloxy)phenol and methanol, respectively.

(ii) Synthesis of 4-hydroxyphenyl-4'-(n-propyloxy)benzoate 4-hydroxyphenyl-4'-(n-propyloxy)benzoate was obtained in the same manner as in the step (ii) of the Example 24, except for using 4-benzyloxyphenyl-4'-(n-propyloxy)benzoate obtained in the step (i) instead of 1-(tert-butoxycarbonyloxy)-4-benzyloxybenzene, and using toluene as the recrystallization solvent.

(iii) Synthesis of 4-[(1-ethoxy)ethoxyphenyl]-4'-(n-propyloxy)benzoate

The reaction was conducted in the same manner as in the Example 1, except for using 4-hydroxyphenyl-4'-(n-propyloxy)benzoate synthesized in the step (ii) and toluene as the eluent of the silica gel column chromatography instead of 4-isopropylphenol and hexane, respectively, and the resultant was recrystallized from hexane to give 4-[(1-ethoxy)ethoxyphenyl]-4'-(n-propyloxy)benzoate.

$^1$H-NMR(CDCl$_3$) ppm: 1.08(t, 3H, CH$_3$), 1.21(t, 3H, terminal CH$_3$), 1.51(d, 3H, branched CH$_3$), 1.78-1.97(m, 2H, CH$_2$), 3.50-3.67(m, 1H, OCH$_2$), 3.73-3.90(m, 1H, OCH$_2$), 4.01(t, 2H, OCH$_2$), 5.38(q, 1H, branched OCH), 6.97(d, 2H, C$_6$H$_4$), 7.03(d, 2H, C$_6$H$_4$), 7.11(d, 2H, C$_6$H$_4$), 8.12(d, 2H, C$_6$H$_4$).

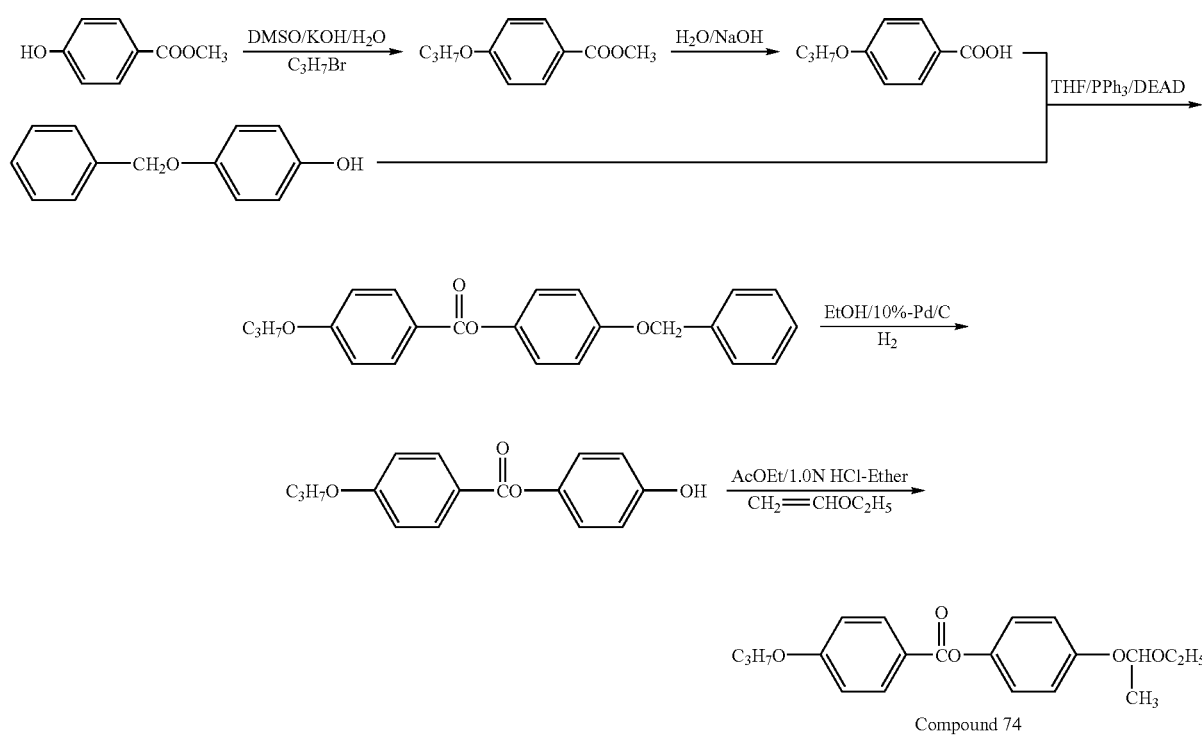

Compound 74

Example 75

Synthesis of 4-n-propylphenyl-4'-[(1-ethoxy)ethoxy]benzoate (Compound 75)

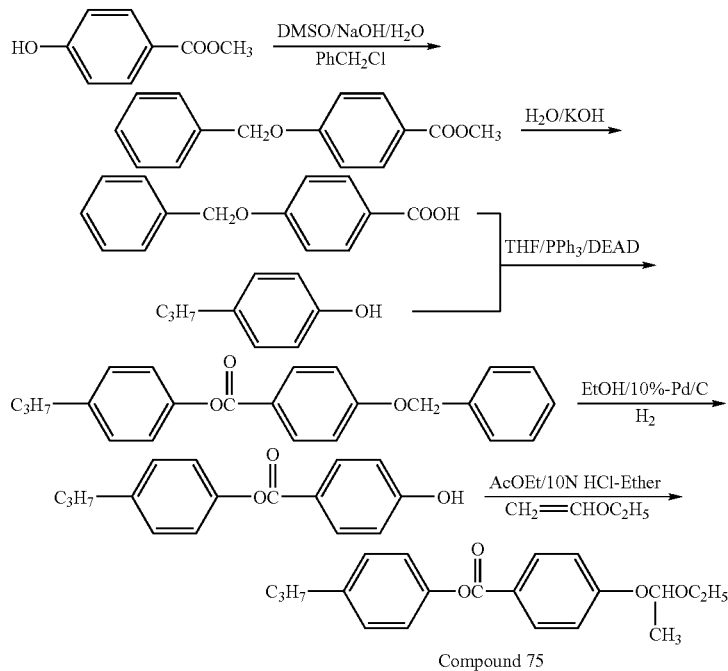

Compound 75

(i) Synthesis of 4-(benzyloxy)benzoic acid 4-(benzyloxy)benzoic acid was obtained in the same manner as in the step (i) of the Example 24, except for using an aqueous solution of sodium hydroxide, benzyl chloride, and an aqueous solution of potassium hydroxide instead of the aqueous solution of potassium hydroxide, n-propyl bromide, and the aqueous solution of sodium hydroxide, respectively.

(ii) Synthesis of 4'-n-propylphenyl-4-(benzyloxy)benzoate

4'-n-propylphenyl-4-(benzyloxy)benzoate was obtained in the same manner as in the step (iii) of the Example 24, except for using 4-(benzyloxy)benzoic acid obtained in the step (i), 4-n-propylphenol, and ethanol as the recrystallization solvent instead of 4-n-propyloxybenzoic acid, 4-(tert-butoxycarbonyloxy)phenol, and methanol, respectively.

(iii) Synthesis of 4-n-propylphenyl-4'-hydroxybenzoate 4-n-propylphenyl-4'-hydroxybenzoate was obtained in the same manner as in the step (ii) of the Example 24, except for using 4'-n-propylphenyl-4-(benzyloxy)benzoate synthesized in the step (ii) instead of 1-(tert-butoxycarbonyloxy)-4-benzyloxybenzene, and using toluene as the recrystallization solvent.

(iv) Synthesis of 4-n-propylphenyl-4'-[(1-ethoxy)ethoxy]benzoate 4-n-propylphenyl-4'-[(1-ethoxy)ethoxy]benzoate was obtained in the same manner as in the Example 1, except for using 4-n-propylphenyl-4'-hydroxybenzoate synthesized in the step (iii) and toluene as the eluent of the silica gel column chromatography instead of 4-isopropylphenol and hexane, respectively.

$^1$H-NMR(CDCl$_3$) ppm: 0.98(t, 3H, CH$_3$), 1.21(t, 3H, terminal CH$_3$), 1.56(d, 3H, branched CH$_3$), 1.59-1.78(m, 2H, CH$_2$), 2.60(t, 2H, CH$_2$), 3.49-3.64(m, 1H, OCH$_2$), 3.71-3.89 (m, 1H, OCH$_2$), 5.53(q, 1H, branched OCH), 7.15-7.24(m, 4H, C$_6$H$_4$), 7.22(d, 2H, C$_6$H$_4$), 8.14(d, 2H, C$_6$H$_4$).

Example 76

Synthesis of 4-n-propyloxyphenyl-4'-[(1-ethoxy)ethoxy]benzoate (Compound 76)

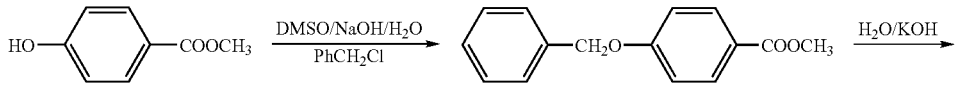

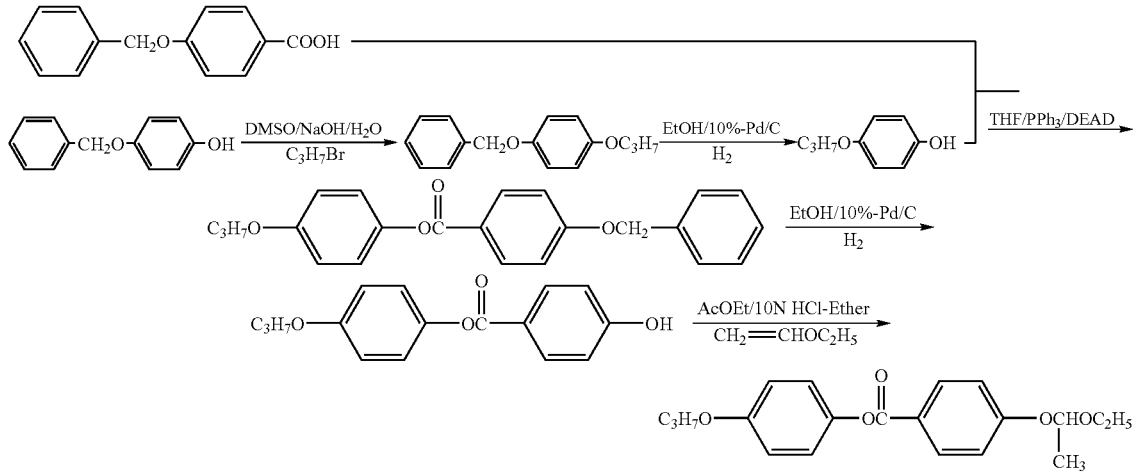

(i) Synthesis of 4'-n-propyloxyphenyl-4-(benzyloxy)benzoate

4'-n-propyloxyphenyl-4-(benzyloxy)benzoate was obtained in the same manner as in the step (iii) of the Example 24, except for using 4-(benzyloxy)benzoic acid obtained in the step (i) of the Example 75, 4-n-propyloxyphenol obtained in the step (ii) of the Example 27, and ethanol as the recrystallization solvent in lieu of 4-n-propyloxybenzoic acid, 4-(tert-butoxycarbonyloxy)phenol, and methanol, respectively.

(ii) Synthesis of 4-n-propyloxyphenyl-4'-hydroxybenzoate 4-n-propyloxyphenyl-4'-hydroxybenzoate was obtained in the same manner as in the step (ii) of the Example 24, except for using 4'-n-propyloxyphenyl-4-(benzyloxy)benzoate synthesized in the step (i) instead of 1-(tert-butoxycarbonyloxy)-4-benzyloxybenzene, and using toluene as the recrystallization solvent.

(iii) Synthesis of 4-n-propyloxyphenyl-4'-[(1-ethoxy)ethoxy]benzoate 4-n-propyloxyphenyl-4'-[(1-ethoxy)ethoxy]benzoate was obtained in the same manner as in the Example 1, except for using 4-n-propyloxyphenyl-4'-hydroxybenzoate synthesized in the step (ii) and toluene as the eluent of the silica gel column chromatography in lieu of 4-isopropylphenol and hexane, respectively.

$^1$H-NMR(CDCl$_3$) ppm: 0.98(t, 3H, CH$_3$), 1.21(t, 3H, terminal CH$_3$), 1.56(d, 3H, branched CH$_3$), 1.59-1.78(m, 2H, CH$_2$), 3.49-3.64(m, 1H, OCH$_2$), 3.71-3.89(m, 1H, OCH$_2$), 4.01(t, 2H, OCH$_2$), 5.53(q, 1H, branched OCH), 7.15-7.24 (m, 4H, C$_6$H$_4$), 7.22(d, 2H, C$_6$H$_4$), 8.14(d, 2H, C$_6$H$_4$).

Example 77

Synthesis of 4-[(1-ethoxy)ethoxyphenyl]-4'-n-propylbenzoate (Compound 77)

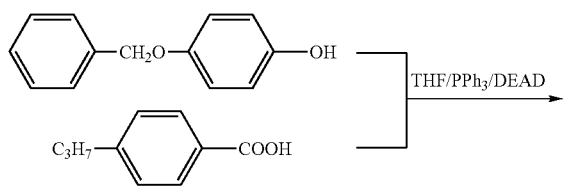

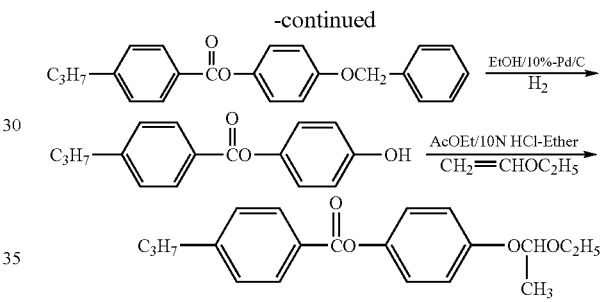

Compound 77

(i) Synthesis of 4-benzyloxy-4'-n-propylphenylbenzoate 4-benzyloxy-4'-n-propylphenylbenzoate was obtained in the same manner as in the step (iii) of the Example 24, except for using 4-(benzyloxy)phenol and ethanol as the recrystallization solvent instead of 4-(tert-butoxycarbonyloxy)phenol and methanol, respectively.

(ii) Synthesis of 4-hydroxyphenyl-4'-n-propylbenzoate 4-hydroxyphenyl-4'-n-propylbenzoate was obtained in the same manner as in the step (ii) of the Example 24, except for using 4-benzyloxy-4'-n-propylphenylbenzoate synthesized in the step (i) in lieu of 1-(tert-butoxycarbonyloxy)-4-benzyloxybenzene, and using toluene as the recrystallization solvent.

(iii) Synthesis of 4-[(1-ethoxy)ethoxyphenyl]-4'-n-propylbenzoate

The reaction was conducted in the same manner as in the Example 1, except for using 4-hydroxyphenyl-4'-n-propylbenzoate synthesized in the step (ii) and toluene as the eluent of the silica gel column chromatography instead of 4-isopropylphenol and hexane, respectively, and the resultant was recrystallized from hexane to give 4-[(1-ethoxy)ethoxyphenyl]-4'-n-propylbenzoate.

$^1$H-NMR(CDCl$_3$) ppm: 0.98(t, 3H, CH$_3$), 1.21(t, 3H, terminal CH$_3$), 1.51(d, 3H, branched CH$_3$), 1.60-1.79(m, 2H, CH$_2$), 2.69(t, 2H, CH$_2$), 3.50-3.65(m, 1H, OCH$_2$), 3.72-3.89

(m, 1H, OCH$_2$), 5.38(q, 1H, branched OCH), 7.04(d, 2H, C$_6$H$_4$), 7.12(d, 2H, C$_6$H$_4$), 7.30(d, 2H, C$_6$H$_4$), 10 8.10(d, 2H, C$_6$H$_4$).

Example 78

Synthesis of 4-[(1-ethoxy)ethoxyphenyl]-4'-(n-propyloxy)benzyl ether (Compound 78)

zyl ether synthesized in the step (i) instead of 4'-acetoxyphenyl-4-methylbenzyl ether, and using toluene as the recrystallization solvent.

(iii) Synthesis of 4-[(1-ethoxy)ethoxyphenyl]-4'-(n-propyloxy)benzyl ether

4-[(1-ethoxy)ethoxyphenyl]-4'-(n-propyloxy)benzyl ether was obtained in the same manner as in the Example 1, except

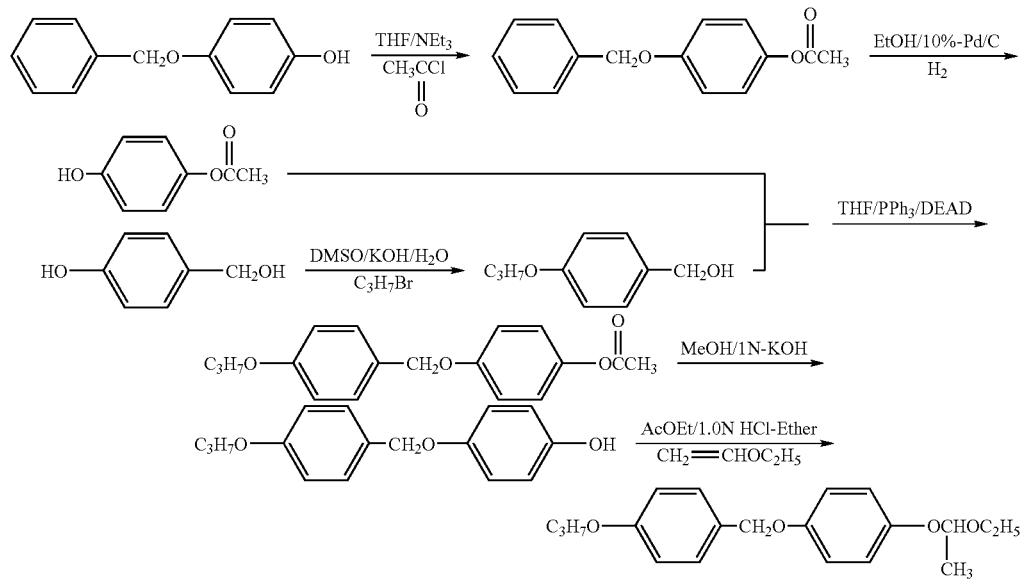

(i) Synthesis of 4'-acetoxyphenyl-4-(n-propyloxy)benzyl ether

4'-acetoxyphenyl-4-(n-propyloxy)benzyl ether was obtained in the same manner as in the step (i) of the Example 27, except for using 4-acetoxyphenol synthesized in the step (ii) of the Example 34 and 4-n-propyloxybenzyl alcohol synthesized in the step (i) of the Example 30 in lieu of 4-(benzyloxy)phenol and n-propyl bromide, respectively.

(ii) Synthesis of 4'-hydroxyphenyl-4-(n-propyloxy)benzyl ether

4'-hydroxyphenyl-4-(n-propyloxy)benzyl ether was obtained in the same manner as in the step (iv) of the Example 34, except for using 4'-acetoxyphenyl-4-(n-propyloxy)benfor using 4'-hydroxyphenyl-4-(n-propyloxy)benzyl ether synthesized in the step (ii) in lieu of 4-isopropylphenol.

$^1$H-NMR(CDCl$_3$) ppm: 1.02(t, 3H, CH$_3$), 1.20(t, 3H, terminal CH$_3$), 1.48(d, 3H, branched CH$_3$), 1.72-1.90(m, 2H, CH$_2$), 3.45-3.62(m, 1H, OCH$_2$), 3.73-3.87(m, 1H, OCH$_2$), 3.90(t, 2H, CH$_2$O), 4.92(s, 2H, CH$_2$O), 5.28(q, 1H, branched OCH), 6.90(d, 2H, C$_6$H$_4$), 7.09(d, 2H, C$_6$H$_4$), 7.33(d, 2H, C$_6$H$_4$).

Example 79

Synthesis of 1-{4-[(1-ethoxy)ethoxyphenyl]}-2-(4-n-propylphenyl)acetylene (Compound 79)

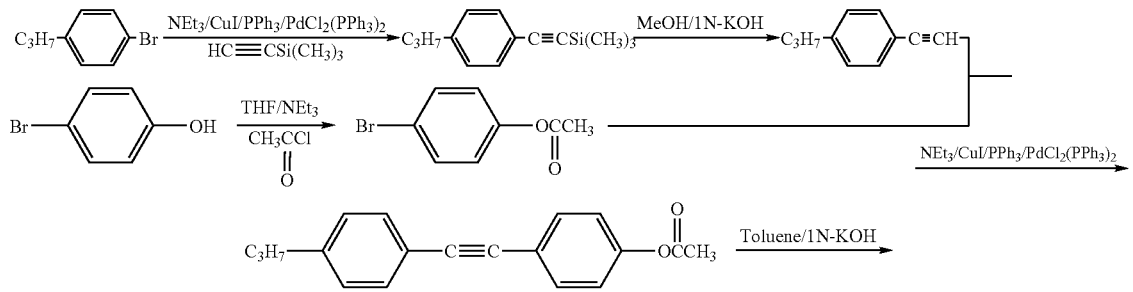

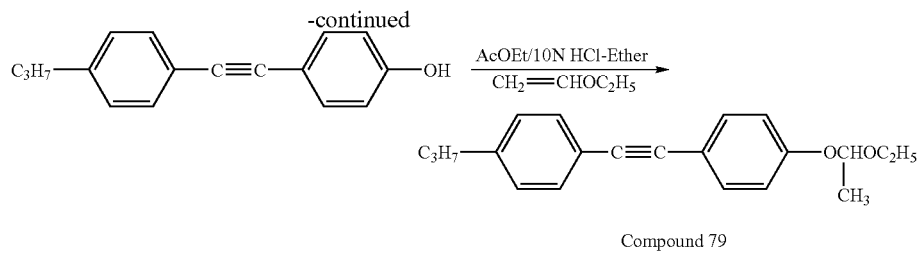

Compound 79

(i) Synthesis of 1-bromo-4-acetoxybenzene 1-bromo-4-acetoxybenzene was synthesized in the same manner as in the step (i) of the Example 34, except for using p-bromophenol instead of 4-(benzyloxy)phenol.

(ii) Synthesis of 1-(4-acetoxyphenyl)-2-(4-n-propylphenyl)acetylene 1-(4-acetoxyphenyl)-2-(4-n-propylphenyl)acetylene was obtained in the same manner as in the step (iii) of the Example 31, except for using 1-bromo-4-acetoxybenzene synthesized in the step (i) instead of 1-(tert-butoxycarbonyloxy)-4-bromobenzene.

(iii) Synthesis of 1-(4-hydroxyphenyl)-2-(4-n-propylphenyl)acetylene 1-(4-hydroxyphenyl)-2-(4-n-propylphenyl)acetylene was obtained in the same manner as in the step (iv) of the Example 34, except for using 1-(4-acetoxyphenyl)-2-(4-n-propylphenyl)acetylene synthesized in the step (ii) instead of 4'-acetoxyphenyl-4-methylbenzyl ether.

(iv) Synthesis of 1-{4-[(1-ethoxy)ethoxyphenyl]}-2-(4-n-propylphenyl)acetylene

1-{4-[(1-ethoxy)ethoxyphenyl]}-2-(4-n-propylphenyl)acetylene was obtained in the same manner as in the Example 1, except for using 1-(4-hydroxyphenyl)-2-(4-n-propylphenyl)acetylene synthesized in the step (iii) in lieu of 4-isopropylphenol.

$^1$H-NMR(CDCl$_3$) ppm: 0.93(t, 3H, CH$_3$), 1.20(t, 3H, terminal CH$_3$), 1.51(d, 3H, branched CH$_3$), 1.58-1.77(m, 2H, CH$_2$), 2.59(t, 2H, CH$_2$), 3.47-3.62(m, 1H, OCH$_2$), 3.70-3.87 (m, 1H, OCH$_2$), 5.42(q, 1H, branched OCH), 6.97(d, 2H, C$_6$H$_4$), 7.14(d, 2H, C$_6$H$_4$), 7.38-7.48(m, 4H, C$_6$H$_4$).

Example 80

Synthesis of 1-{4-[(1-ethoxy)ethoxyphenyl]}-2-(4-n-propyloxyphenyl)acetylene (Compound 80)

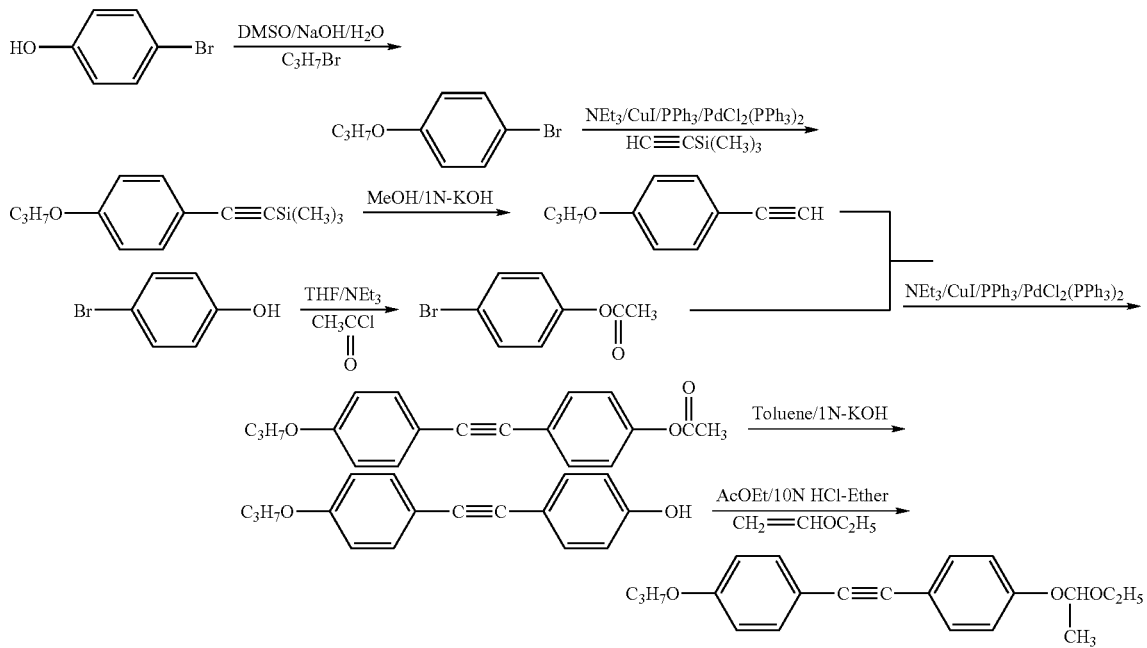

Compound 80

(i) Synthesis of 1-(4-acetoxyphenyl)-2-(4-n-propyloxyphenyl)acetylene 1-(4-acetoxyphenyl)-2-(4-n-propyloxyphenyl)acetylene was obtained in the same manner as in the step (iii) of the Example 31, except for using 1-bromo-4-(acetoxy)benzene synthesized in the step (i) of the Example 79, 4-(n-propyloxy)phenylacetylene synthesized in the step (iii) of the Example 32, and hexane as the recrystallization solvent instead of 4-n-propylphenylacetylene, 1-(tert-butoxycarbonyloxy)-4-bromobenzene, and ethanol, respectively.

(ii) Synthesis of 1-(4-hydroxyphenyl)-2-(4-n-propyloxyphenyl)acetylene 1-(4-hydroxyphenyl)-2-(4-n-propyloxyphenyl)acetylene was obtained in the same manner as in the step (iv) of the Example 34, except for using 1-(4-acetoxyphenyl)-2-(4-n-propyloxyphenyl)acetylene synthesized in the step (i) in lieu of 4'-acetoxyphenyl-4-methylbenzyl ether.

(iii) Synthesis of 1-{4-[(1-ethoxy)ethoxyphenyl]}-2-(4-n-propyloxyphenyl)acetylene 1-{4-[(1-ethoxy)ethoxyphenyl]}-2-(4-n-propyloxyphenyl)acetylene was obtained in the same manner as in the Example 1, except for using 1-(4-hydroxyphenyl)-2-(4-n-propyloxyphenyl)acetylene synthesized in the step (ii) in lieu of 4-isopropylphenol.

$^1$H-NMR(CDCl$_3$) ppm: 1.05(t, 3H, CH$_3$), 1.20(t, 3H, terminal CH$_3$), 1.51(d, 3H, branched CH$_3$), 1.73-1.94(m, 2H, CH$_2$), 3.48-3.63(m, 1H, OCH$_2$), 3.70-3.88(m, 1H, OCH$_2$), 3.94(t, 2H, OCH$_2$), 5.42(q, 1H, branched OCH), 6.85(d, 2H, C$_6$H$_4$), 6.96(d, 2H, C$_6$H$_4$), 7.43(d, 4H, C$_6$H$_4$).

Example 81

Synthesis of 4-[(1-ethoxy)ethoxyphenyl]-4'-(n-propyl)benzyl ether (Compound 81)

(i) Synthesis of 4'-acetoxyphenyl-4-(n-propyl)benzyl ether

4'-acetoxyphenyl-4-(n-propyl)benzyl ether was obtained in the same manner as in the step (i) of the Example 27, except for using 4-acetoxyphenol synthesized in the step (ii) of the Example 34 and 4-n-propylbenzyl chloride synthesized in the step (iii) of the Example 33 instead of 4-(benzyloxy)phenol and n-propyl bromide, respectively.

(ii) Synthesis of 4'-hydroxyphenyl-4-(n-propyl)benzyl ether

4'-hydroxyphenyl-4-(n-propyl)benzyl ether was obtained in the same manner as in the Example 34, except for using 4'-acetoxyphenyl-4-(n-propyl)benzyl ether synthesized in the step (i) instead of 4'-acetoxyphenyl-4-methylbenzyl ether in the step (iv) of the Example 34.

(iii) Synthesis of 4-[(1-ethoxy)ethoxyphenyl]-4'-(n-propyl)benzyl ether

4-[(1-ethoxy)ethoxyphenyl]-4'-(n-propyl)benzyl ether was obtained in the same manner as in the Example 1, except for using 4'-hydroxyphenyl-4-(n-propyl)benzyl ether synthesized in the step (ii) and toluene as the eluent of the silica gel column chromatography instead of 4-isopropylphenol and hexane, respectively.

$^1$H-NMR(CDCl$_3$) ppm: 0.93(t, 3H, CH$_3$), 1.21(t, 3H, terminal CH$_3$), 1.45(d, 3H, branched CH$_3$), 1.59-1.760(m, 2H, CH$_2$), 2.60(t, 2H, CH$_2$), 3.49-3.64(m, 1H, OCH$_2$), 3.74-3.90 (m, 1H, OCH$_2$), 4.99(s, 2H, CH$_2$O), 5.25(q, 1H, branched OCH), 6.84-6.98(m, 4H, C$_6$H$_4$), 7.19(d, 2H, C$_6$H$_4$), 7.34(d, 2H, C$_6$H$_4$).

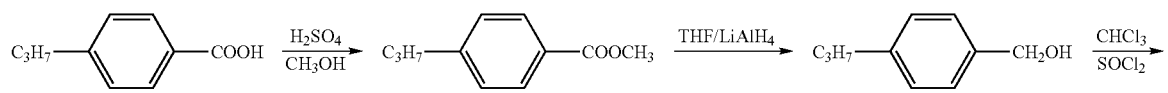

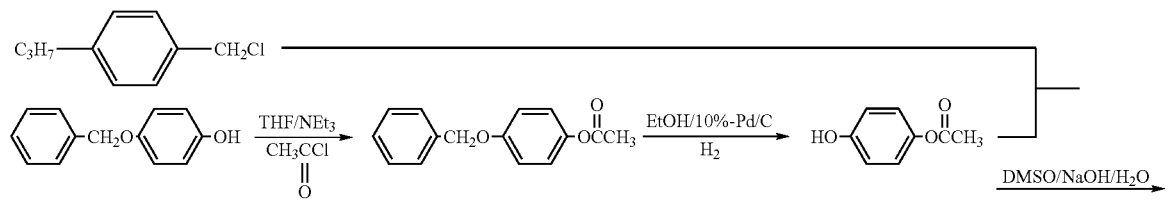

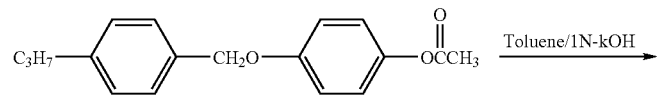

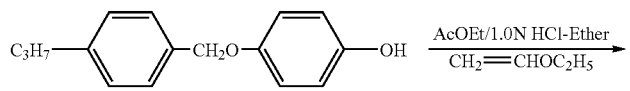

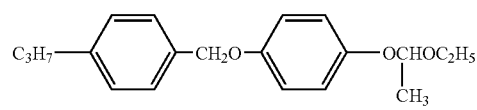

Compound 81

Example 82

Synthesis of 4-[(1-ethoxy)ethoxyphenyl]-4'-methylbenzyl ether (Compound 82)

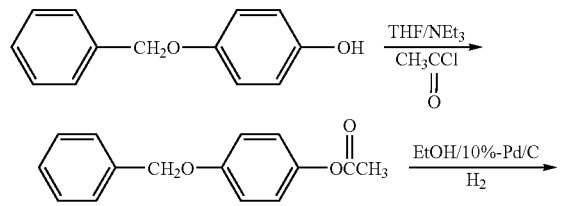

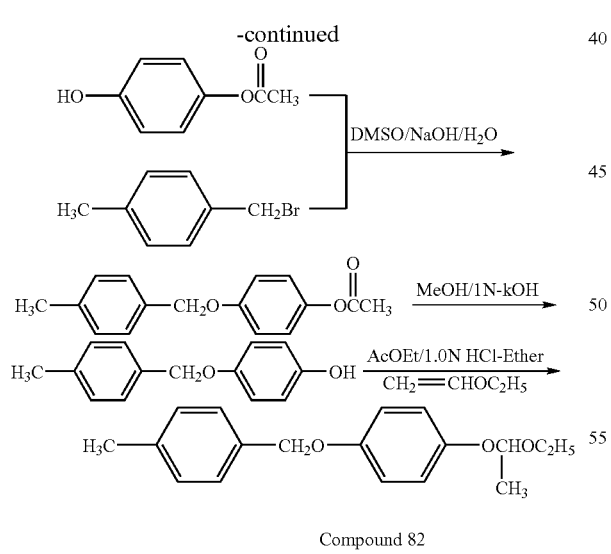

Compound 82

4-[(1-ethoxy)ethoxyphenyl]-4'-methylbenzyl ether was obtained in the same manner as in the Example 1, except for using 4'-hydroxyphenyl-4-methylbenzyl ether synthesized in the step (iv) of the Example 34 and toluene as the eluent of the silica gel column chromatography instead of 4-isopropylphenol and hexane, respectively.

$^1$H-NMR(CDCl$_3$) ppm: 1.20(t, 3H, terminal CH$_3$), 1.45(d, 3H, branchedCH$_3$), 2.37(s, 3H, CH$_3$), 3.48-3.62(m, 1H, OCH$_2$), 3.74-3.90(m, 1H, OCH$_2$), 4.99(s, 2H, CH$_2$O), 5.27(q, 1H, branched OCH), 6.84-6.98(m, 4H, C$_6$H$_4$), 7.18(d, 2H, C$_6$H$_4$), 7.31(d, 2H, C$_6$H$_4$).

Example 83

Synthesis of 4-[(1-ethoxy)ethoxy]-4'-n-pentylbiphenyl (Compound 83)

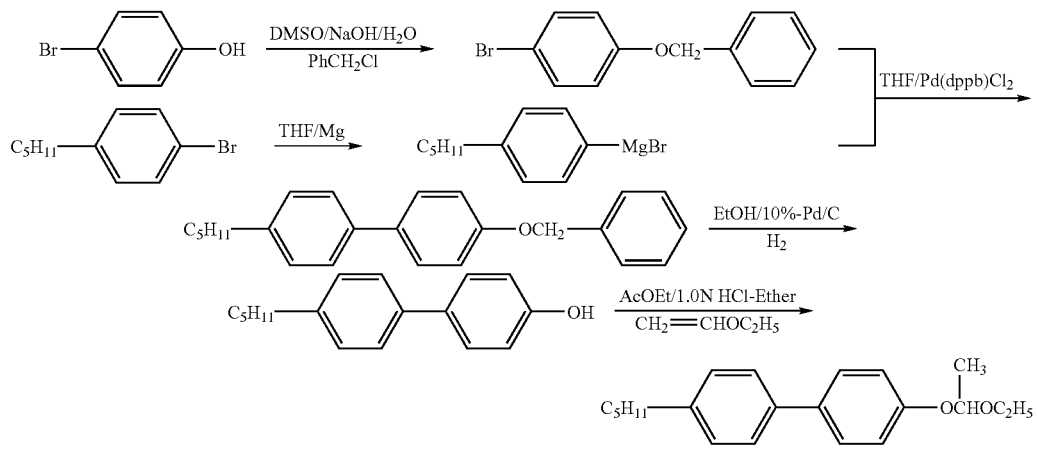

Compound 83

4-[(1-ethoxy)ethoxy]-4'-n-pentylbiphenyl was obtained in the same manner as in the Example 1, except for using 4-n-pentyl-4'-hydroxybiphenyl synthesized in the step (iii) of the Example 35 and toluene as the eluent of the silica gel column chromatography in lieu of 4-isopropylphenol and hexane, respectively.

$^1$H-NMR(CDCl$_3$) ppm: 0.90(t, 3H, CH$_3$), 1.25(t, 3H, terminal CH$_3$), 1.29-1.48(m, 4H, CH$_2$), 1.54(d, 3H, branched CH$_3$), 1.59-1.75(m, 4H, CH$_2$), 2.63(t, 3H, CH$_2$), 3.50-3.66 (m, 1H, OCH$_2$), 3.75-3.90(m, 1H, OCH$_2$), 5.42(q, 1H, branched OCH), 7.05(d, 2H, C$_6$H$_4$), 7.22(d, 2H, C$_6$H$_4$), 7.48 (t, 4H, C$_6$H$_4$).

Example 84

Synthesis of 4-[(1-ethoxy)ethoxyphenyl]benzene (Compound 84)

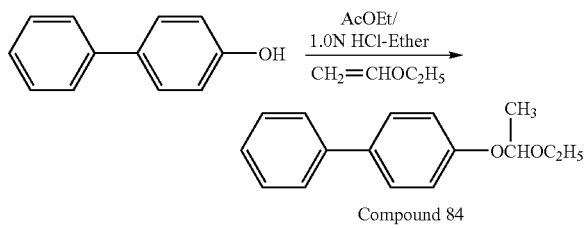

Compound 84

4-[(1-ethoxy)ethoxyphenyl]benzene was obtained in the same manner as in the Example 1, except for using 4-phenylphenol and toluene as the eluent of the silica gel column chromatography in lieu of 4-isopropylphenol and hexane, respectively.

$^1$H-NMR(CDCl$_3$) ppm: 1.21(t, 3H, terminal CH$_3$), 1.53(d, 3H, branched CH$_3$), 3.50-3.69(m, 1H, OCH$_2$), 3.76-3.91(m, 1H, OCH$_2$), 5.42(q, 1H, branched OCH), 7.24(d, 2H, C$_6$H$_4$), 7.30-7.39(m, 1H, C$_6$H$_5$), 7.39-7.49(m, 2H, C$_6$H$_5$), 7.52-7.63 (m, 4H, C$_6$H$_4$ and C$_6$H$_5$).

Example 85

Synthesis of 4-[(1-ethoxy)ethoxy]-4'-(n-propyloxy) biphenyl (Compound 85)

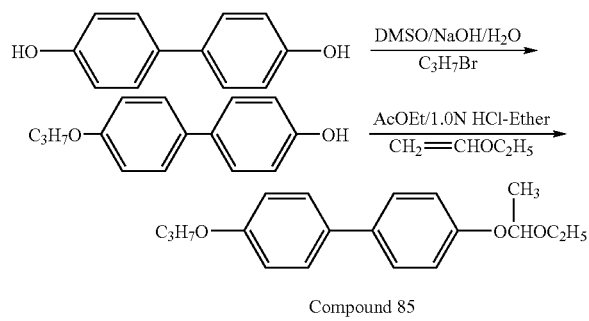

Compound 85

4-[(1-ethoxy)ethoxy]-4'-(n-propyloxy)biphenyl was obtained in the same manner as in the Example 1, except for using 4-n-propyloxy-4'-hydroxybiphenyl synthesized in the step (i) of the Example 37 and toluene as the eluent of the silica gel column chromatography instead of 4-isopropylphenol and hexane, respectively.

$^1$H-NMR(CDCl$_3$) ppm: 1.08(t, 3H, CH$_3$), 1.24(t, 3H, terminal CH$_3$), 1.52(d, 3H, branched CH$_3$), 1.78-1.92(m, 2H, CH$_2$), 3.49-3.68(m, 1H, OCH$_2$), 3.75-3.90(m, 1H, OCH$_2$), 3.95(t, 2H, OCH$_2$), 5.40(q, 1H, branched OCH), 6.95(d, 2H, C$_6$H$_4$), 7.05(d, 2H, C$_6$H$_4$), 7.46(t, 4H, C$_6$H$_4$).

Example 86

Synthesis of 1-(1-ethoxy)ethoxynaphthalene (Compound 86)

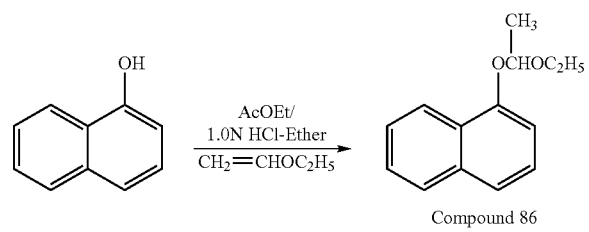

Compound 86

1-(1-ethoxy)ethoxynaphthalene was obtained in the same manner as in the Example 1, except for using 1-naphthol and toluene as the eluent of the silica gel column chromatography in lieu of 4-isopropylphenol and hexane, respectively.

$^1$H-NMR(CDCl$_3$) ppm: 1.24(t, 3H, terminal CH$_3$), 1.52(d, 3H, branched CH$_3$), 3.49-3.68(m, 1H, OCH$_2$), 3.75-3.90(m, 1H, OCH$_2$), 5.40(q, 1H, branched OCH), 7.32(q, 1H, C$_{10}$H$_7$), 7.42-7.58(m, 3H, C$_{10}$H$_7$), 7.74(d, 1H, C$_{10}$H$_7$), 7.81-8.00(m, 2H, C$_{10}$H$_7$).

Example 87

Synthesis of 2-(1-ethoxy)ethoxynaphthalene (Compound 87)

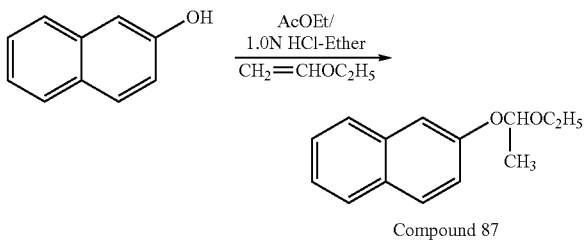

Compound 87

2-(1-ethoxy)ethoxynaphthalene was obtained in the same manner as in the Example 1, except for using 2-naphthol and toluene as the eluent of the silica gel column chromatography instead of 4-isopropylphenol and hexane, respectively.

$^1$H-NMR(CDCl$_3$) ppm: 1.24(t, 3H, terminal CH$_3$), 1.52(d, 3H, branched CH$_3$), 3.49-3.68(m, 1H, OCH$_2$), 3.75-3.90(m, 1H, OCH$_2$), 5.40(q, 1H, branched OCH), 7.31(q, 1H, C$_{10}$H$_7$), 7.41-7.52(m, 2H, C$_{10}$H$_7$), 7.64(d, 1H, C$_{10}$H$_7$), 7.77-7.88(m, 3H, C$_{10}$H$_7$).

Example 88

Synthesis of 6-n-pentyl-2-(1-ethoxy)ethoxynaphthalene (Compound 88)

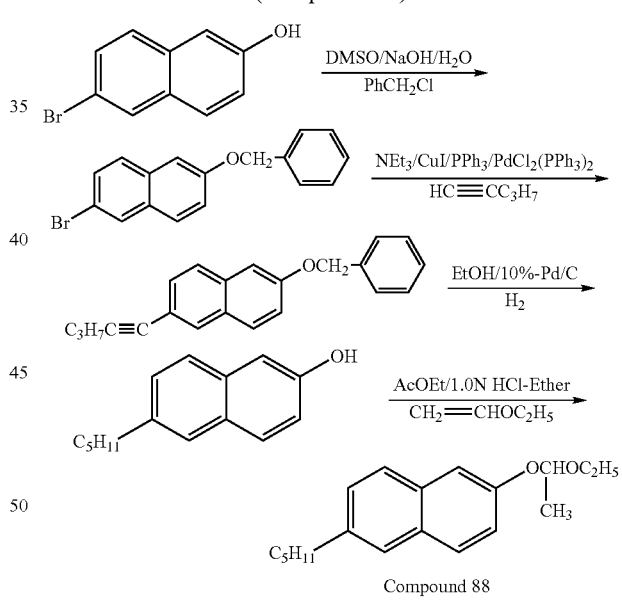

Compound 88

6-n-pentyl-2-(1-ethoxy)ethoxynaphthalene was obtained in the same manner as in the Example 1, except for using 6-n-pentyl-2-naphthol synthesized in the step (iii) of the Example 41 and toluene as the eluent of the silica gel column chromatography instead of 4-isopropylphenol and hexane, respectively.

$^1$H-NMR(CDCl$_3$) ppm: 0.90(t, 3H, CH$_3$), 1.23(t, 3H, terminal CH$_3$), 1.29-1.48(m, 4H, CH$_2$), 1.54(d, 3H, branched CH$_3$), 1.56-1.78(m, 2H, CH$_2$), 2.63(t, 2H, CH$_2$), 3.50-3.68 (m, 1H, OCH$_2$), 3.75-3.91(m, 1H, OCH$_2$), 5.42(q, 1H, branched OCH), 7.24-7.37(m, 2H, C$_{10}$H$_6$), 7.59(d, 2H, C$_{10}$H$_6$), 7.68-7.80(q, 2H, C$_{10}$H$_6$).

Example 89

Synthesis of 4-(1-ethoxy)ethoxy-N-(4-ethylphenyl)carbamate (Compound 89)

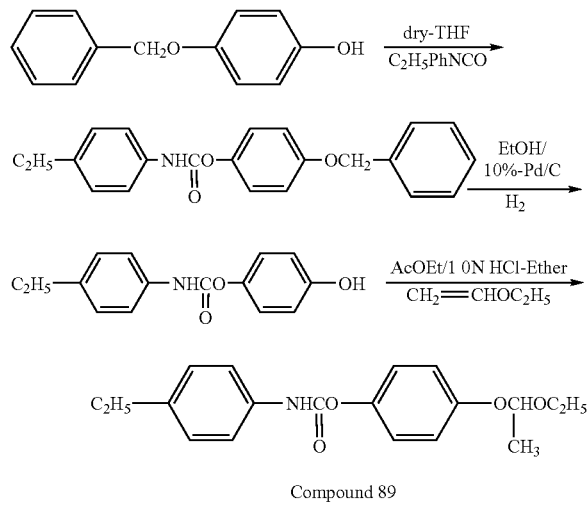

Compound 89

4-(1-ethoxy)ethoxy-N-(4-ethylphenyl)carbamate was obtained in the same manner as in the Example 1, except for using 4-(hydroxyphenyl)-N-(4-ethylphenyl)carbamate synthesized in the step (ii) of the Example 42 in lieu of 4-isopropylphenol.

$^1$H-NMR(CDCl$_3$) ppm: 1.12(t, 3H, CH$_3$), 1.23(t, 3H, terminal CH$_3$), 1.54(d, 3H, branched CH$_3$), 2.63(t, 2H, CH$_2$), 3.50-3.68(m, 1H, OCH$_2$), 3.75-3.91(m, 1H, OCH$_2$), 5.42(q, 1H, branched OCH), 6.87(s, 1H, NH), 7.14-7.21(m, 6H, C$_6$H$_4$), 7.35(d, 2H, C$_6$H$_4$).

Example 90

Synthesis of 1,3,5-tri(2-tert-butoxycarbonylvinyl)benzene (Compound 90)

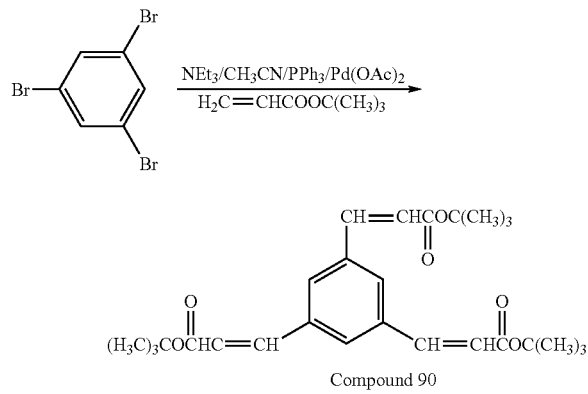

Compound 90

1,3,5-tri(2-tert-butoxycarbonylvinyl)benzene was obtained in the same manner as in the Example 44, except for using 1,3,5-tribromobenzene instead of 4-(tert-butoxycarbonyloxy)-4'-bromobiphenyl.

$^1$H-NMR(CDCl$_3$) ppm: 1.55(s, 27H, tert-Bu), 6.42(d, 3H, CH=CH), 7.56(d, 3H, CH=CH), 7.60(s, 3H, C$_6$H$_4$).

Example 91

Synthesis of 1-(2-tert-butoxycarbonylvinyl)-4-(trans-4'-n-propylcyclohexyl)benzene (Compound 91)

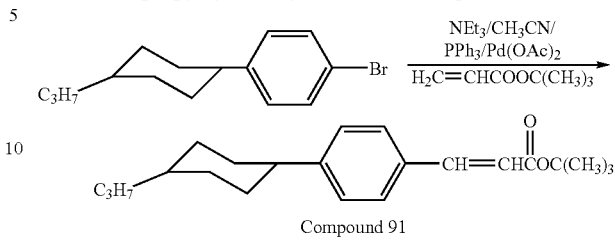

Compound 91

1-(2-tert-butoxycarbonylvinyl)-4-(trans-4'-n-propylcyclohexyl)benzene was obtained in the same manner as in the Example 44, except for using 1-(trans-4-n-propylcyclohexyl)-4-bromobenzene in lieu of 4-(tert-butoxycarbonyloxy)-4'-bromobiphenyl.

$^1$H-NMR(CDCl$_3$) ppm: 0.90(t, 3H, CH$_3$), 0.95-1.50(m, 9H, C$_2$H$_4$ and C$_6$H$_{10}$), 1.55(s, 9H, tert-Bu), 1.80-1.98(m, 4H, C$_6$H$_{10}$), 2.39-2.59(m, 1H, C$_6$H$_{10}$) 6.32(d, 1H, CH=CH), 7.21(d, 2H, C$_6$H$_4$), 7.42(d, 2H, C$_6$H$_4$), 7.56(d, 1H, CH=CH).

Example 92

Synthesis of 1,4-di(2-tert-butoxycarbonylvinyl)benzene (Compound 92)

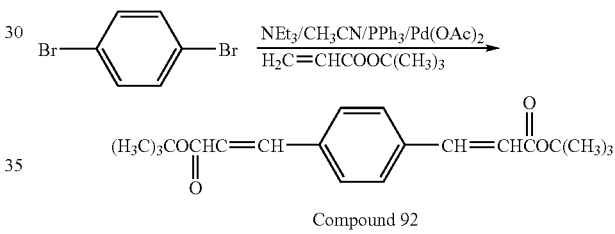

Compound 92

1,4-di(2-tert-butoxycarbonylvinyl)benzene was obtained in the same manner as in the Example 44, except for using p-dibromobenzene and ethanol as the recrystallization solvent instead of 4-(tert-butoxycarbonyloxy)-4'-bromobiphenyl and methanol, respectively.

$^1$H-NMR(CDCl$_3$) ppm: 1.54(s, 18H, tert-Bu), 6.39(d, 2H, CH=CH), 7.51(s, 4H, C$_6$H$_4$), 7.56(d, 2H, CH=CH).

Example 93

Synthesis of 1,4-difluoro-2,5-di(2-tert-butoxycarbonylvinyl)benzene (Compound 93)

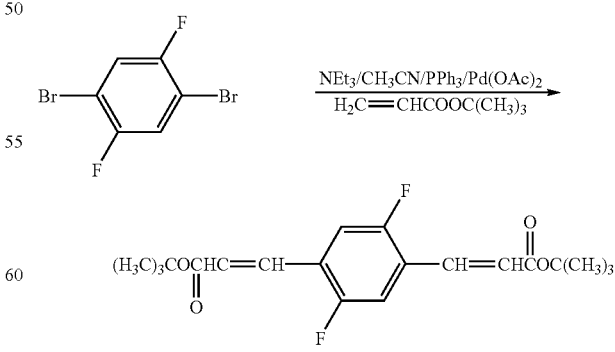

Compound 93

1,4-difluoro-2,5-di(2-tert-butoxycarbonylvinyl)benzene was obtained in the same manner as in the Example 44, except for using 2,5-difluoro-1,4-dibromobenzene and hexane as the recrystallization solvent in lieu of 4-(tert-butoxycarbonyloxy)-4'-bromobiphenyl and methanol, respectively.

$^1$H-NMR(CDCl$_3$) ppm: 1.55(s, 18H, tert-Bu), 6.44(d, 2H, CH=CH), 7.22-7.39(m, 2H, C$_6$H$_4$), 7.59(d, 2H, CH=CH).

Example 94

Synthesis of 2,2-bis[4-(2-tert-butoxycarbonylvinyl) phenyl]hexafluoropropane (Compound 94)

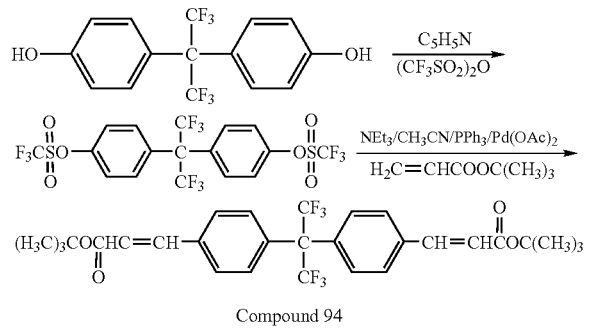

Compound 94

(i) Synthesis of 2,2-bis[4-(trifluoromethylsulfonyloxy) phenyl]hexafluoropropane In 50 ml of dehydrated pyridine (C$_5$H$_5$N) was dissolved 5.0 g (14.9 mmol) of 2,2-bis(4-hydroxyphenyl)hexafluoropropane, and 8.8 g (31.2 mmol) of trifluoromethanesulfonic anhydride was added to the mixture with cooling with ice. The reaction was carried out at a room temperature for 24 hours. The reaction mixture was poured into an iced water, and the resultant mixture was acidified by adding hydrochloric acid. The resultant solid was collected by filtration, washed with water, dried, and recrystallized from hexane to provide 7.07 g (11.8 mmol) of 2,2-bis[4-(trifluoromethylsulfonyloxy)phenyl]hexafluoropropane.

(ii) Synthesis of 2,2-bis[4-(2-tert-butoxycarbonylvinyl) phenyl]hexafluoropropane The reaction was conducted in the same manner as in the Example 44, except for using 2,2-bis[4-(trifluoromethylsulfonyloxy)phenyl]hexafluoropropane synthesized in the step (i) instead of 4-(tert-butoxycarbonyloxy)-4'-bromobiphenyl, and the resultant was purified by silica gel column chromatography (eluent: hexane/ethyl acetate=95/5) to provide 2,2-bis[4-(2-tert-butoxycarbonylvinyl)phenyl]hexafluoropropane $^1$H-NMR(CDCl$_3$) ppm: 1.55(s, 18H, tert-Bu), 6.40(d, 2H, CH=CH), 7.39(d, 4H, C$_6$H$_4$), 7.51(d, 4H, C$_6$H$_4$), 7.57(d, 2H, CH=CH).

Example 95

Synthesis of 4,4'-di(2-tert-butoxycarbonylvinyl)biphenyl (Compound 95)

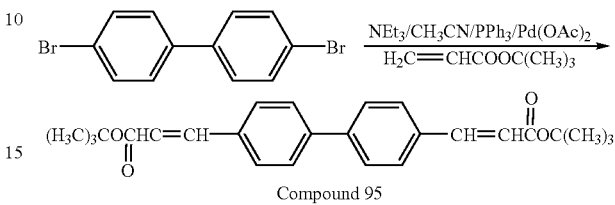

Compound 95

4,4'-di(2-tert-butoxycarbonylvinyl)biphenyl was obtained in the same manner as in the Example 44, except for using 4,4'-dibromobiphenyl and ethanol as the recrystallization solvent in lieu of 4-(tert-butoxycarbonyloxy)-4'-bromobiphenyl and methanol, respectively.

$^1$H-NMR(CDCl$_3$) ppm: 1.55(s, 18H, tert-Bu), 6.51(d, 2H, CH=CH), 7.50-7.68(m, 10H, C$_6$H$_4$ and CH=CH).

Example 96

Synthesis of 4'-n-propyloxyphenyl-4-(2-tert-butoxycarbonylvinyl)benzyl ether (Compound 96)

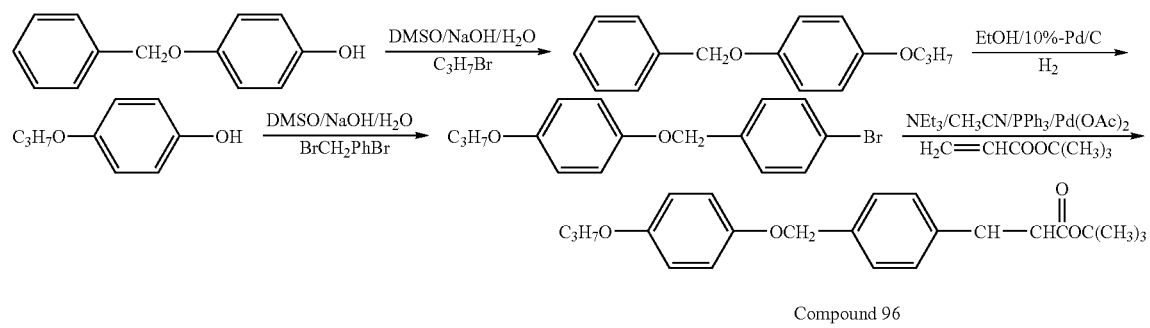

Compound 96

(i) Synthesis of 4'-n-propyloxyphenyl-4-bromobenzyl ether

4'-n-propyloxyphenyl-4-bromobenzyl ether was obtained in the same manner as in the step (i) of the Example 27, except for using 1-(n-propyloxy)phenol synthesized in the step (ii) of the Example 27 and p-bromobenzyl bromide instead of 4-(benzyloxy)phenol and n-propyl bromide, respectively.

(ii) Synthesis of 4'-n-propyloxyphenyl-4-(2-tert-butoxycarbonylvinyl)benzyl ether 4'-n-propyloxyphenyl-4-(2-tert-butoxycarbonylvinyl) benzyl ether was obtained in the same manner as in the Example 44, except for using 4'-(n-propyloxy)phenyl-4-bromobenzyl ether synthesized in the step (i) and hexane as the recrystallization solvent in lieu of 4-(tert-butoxycarbonyloxy)-4'-bromobiphenyl and methanol, respectively.

$^1$H-NMR(CDCl$_3$) ppm: 1.01(t, 3H, CH$_3$), 1.55(s, 9H, tert-Bu), 1.69-1.79(m, 2H, CH$_2$), 3.88(t, 2H, OCH$_2$), 5.01(s, 2HOCH$_2$), 6.36(d, 1H, CH=CH), 6.74-6.92(m, 4H, C$_6$H$_4$), 7.34-7.55(m, 4H, C$_6$H$_4$), 7.58(d, 1H, CH=CH).

Example 97

Synthesis of 2,6-di(2-tert-butoxycarbonylvinyl)naphthalene (Compound 97)

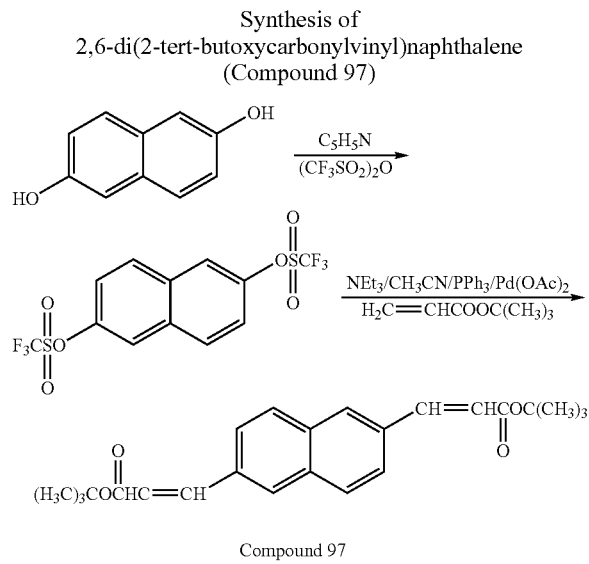

Compound 97

(i) Synthesis of 2,6-di(trifluoromethylsulfonyloxy)naphthalene

The reaction was conducted in the same manner as in the step (i) of the Example 94, except for using 2,6-dihydroxynaphthalene instead of 2,2-bis(4-hydroxyphenyl)hexafluoropropane, and the resultant was recrystallized from methanol to give 2,6-di(trifluoromethylsulfonyloxy)naphthalene.

(ii) Synthesis of 2,6-di(2-tert-butoxycarbonylvinyl)naphthalene 2,6-di(2-tert-butoxycarbonylvinyl)naphthalene was obtained in the same manner as in the Example 44, except for using 2,6-di(trifluoromethylsulfonyloxy)naphthalene synthesized in the step (i) and acetone as the recrystallization solvent instead of 4-(tert-butoxycarbonyloxy)-4'-bromobiphenyl and methanol, respectively.

$^1$H-NMR(CDCl$_3$) ppm: 1.56(s, 18H, tert-Bu), 6.50(d, 2H, CH=CH), 7.62-7.92(m, 8H, C$_{10}$H$_6$ and CH=CH).

Example 98

Synthesis of 4-n-propyl-4'-(2-tert-butoxycarbonylvinyl)biphenyl (Compound 98)

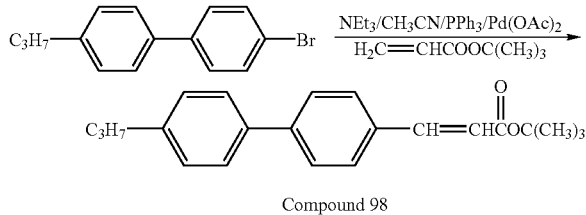

Compound 98

4-n-propyl-4'-(2-tert-butoxycarbonylvinyl)biphenyl was obtained in the same manner as in the Example 44, except for using 4-n-propyl-4'-bromobiphenyl and hexane as the recrystallization solvent instead of 4-(tert-butoxycarbonyloxy)-4'-bromobiphenyl and methanol, respectively.

$^1$H-NMR(CDCl$_3$) ppm: 0.99(t, 3H, CH$_3$), 1.55(s, 9H, tert-Bu), 1.60-1.82(m, 2H, CH$_2$), 2.64(t, 2H, CH$_2$), 6.39(d, 1H, CH=CH), 7.26(d, 2H, C$_6$H$_4$), 7.48-7.68(m, 7H, C$_6$H$_4$ and CH=CH).

Example 99

Synthesis of 4'-n-propylphenyl-4-(2-tert-butoxycarbonylvinyl)benzyl ether (Compound 99)

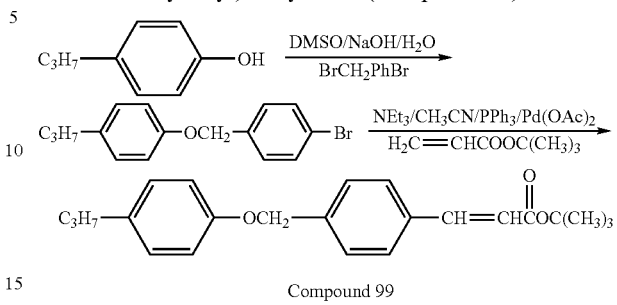

Compound 99

(i) Synthesis of 4'-n-propylphenyl-4-bromobenzyl ether

4'-n-propylphenyl-4-bromobenzyl ether was obtained in the same manner as in the step (i) of the Example 27, except for using 4-n-propylphenol and p-bromobenzyl bromide in lieu of 4-(benzyloxy)phenol and n-propylphenol, respectively.

(ii) Synthesis of 4'-n-propylphenyl-4-(2-tert-butoxycarbonylvinyl)benzyl ether

4'-n-propylphenyl-4-(2-tert-butoxycarbonylvinyl)benzyl ether was obtained in the same manner as in the Example 44, except for using 4'-n-propylphenyl-4-bromobenzyl ether synthesized in the step (i) and hexane as the recrystallization solvent instead of 4-(tert-butoxycarbonyloxy)-4'-bromobiphenyl and methanol, respectively.

$^1$H-NMR(CDCl$_3$) ppm: 0.91(t, 3H, CH$_3$), 1.55(s, 9H, tert-Bu), 1.53-1.719(m, 2H, CH$_2$), 2.52(t, 2H, CH$_2$), 5.06(s, 2H, OCH$_2$), 6.37(d, 1H, CH=CH), 6.88(d, 2H, C$_6$H$_4$), 7.09(d, 2H, C$_6$H$_4$), 7.43(d, 2H, C$_6$H$_4$), 7.52(d, 2H, C$_6$H$_4$), 7.59(d, 1H, CH=CH).

Example 100

Synthesis of 4'-n-pentylphenyl-4-(2-tert-butoxycarbonylvinyl)benzoate (Compound 100)

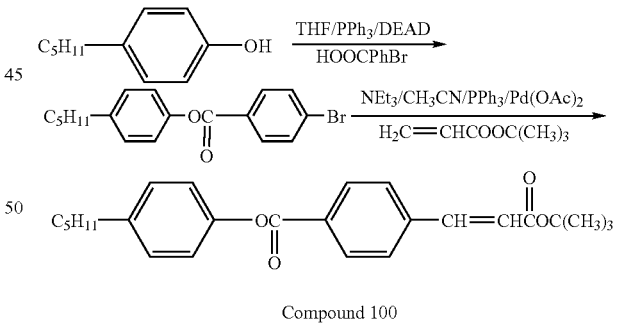

Compound 100

(i) Synthesis of 4'-n-pentylphenyl-4-bromobenzoate

4'-n-pentylphenyl-4-bromobenzoate was obtained in the same manner as in the step (iii) of the Example 24, except for using 4-n-pentylphenol and p-bromobenzoic acid (HOOCPhBr) instead of 4-propyloxybenzoic acid and 4-(tert-butoxycarbonyloxy)phenol, respectively.

(ii) Synthesis of 4'-n-pentylphenyl-4-(2-tert-butoxycarbonylvinyl)benzoate

4'-n-pentylphenyl-4-(2-tert-butoxycarbonylvinyl)benzoate was obtained in the same manner as in the Example 44, except for using 4'-n-pentylphenyl-4-bromobenzoate synthesized in the step (i) and hexane as the recrystallization solvent in lieu 20 of 4-(tert-butoxycarbonyloxy)-4'-bromobiphenyl and methanol, respectively.

$^1$H-NMR(CDCl$_3$) ppm: 0.90(t, 3H, CH$_3$), 1.24-1.48(m, 4H, C$_2$H$_4$), 1.55(s, 9H, tert-Bu), 1.58-1.75(m, 2H, CH$_2$), 2.64(t, 2H, CH$_2$), 6.49(d, 1H, CH=CH), 7.11 (d, 2H, C$_6$H$_4$), 7.23(d, 2H, C$_6$H$_4$), 7.62(d, 2H, C$_6$H$_4$), 7.63(d, 1H, CH=CH), 8.19(d, 2H, C$_6$H$_4$).

Example 101

Synthesis of 4'-n-pentyloxy-4-(2-tert-butoxycarbonylvinyl)biphenyl (Compound 101)

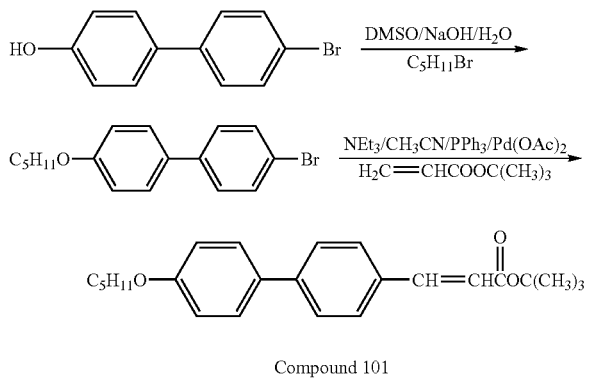

Compound 101

(i) Synthesis of 4'-n-pentyloxy-4-bromobiphenyl

4'-n-pentyloxy-4-bromobiphenyl was obtained in the same manner as in the step (i) of the Example 27, except for using 4'-hydroxy-4-bromobiphenyl, n-pentyl bromide, and ethanol as the recrystallization solvent instead of 4-(benzyloxy)phenol, n-propyl bromide, and methanol, respectively.

(ii) Synthesis of 4'-n-pentyloxy-4-(2-tert-butoxycarbonylvinyl)biphenyl

4'-n-pentyloxy-4-(2-tert-butoxycarbonylvinyl)biphenyl was obtained in the same manner as in the Example 44, except for using 4'-n-pentyloxy-4-bromobiphenyl synthesized in the step (i) and hexane as the recrystallization solvent instead of 4-(tert-butoxycarbonyloxy)-4'-bromobiphenyl and methanol, respectively.

$^1$H-NMR(CDCl$_3$) ppm: 0.94(t, 3H, CH$_3$), 1.30-1.55(m, 4H, C$_2$H$_4$), 1.55(s, 9H, tert-Bu), 1.74-1.90(m, 2H, CH$_2$), 4.00(t, 2H, OCH$_2$), 6.39(d, 1H, CH=CH), 6.98(d, 2H, C$_6$H$_4$), 7.50-7.61(d, 6H, C$_6$H$_4$), 7.61(d, 1H, CH=CH).

Example 102

Synthesis of 2-n-propyloxy-6-(2-tert-butoxycarbonylvinyl)naphthalene (Compound 102)

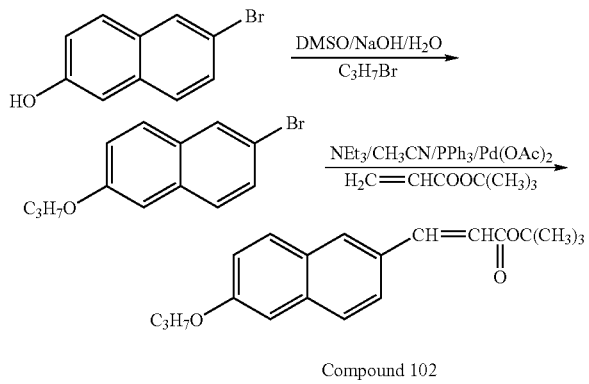

Compound 102

(i) Synthesis of 2-n-propyloxy-6-bromonaphthalene 2-n-propyloxy-6-bromonaphthalene was obtained in the same manner as in the step (i) of the Example 27, except for using 2-hydroxy-6-bromonaphthalene and hexane as the recrystallization solvent in lieu of 4-(benzyloxy)phenol and methanol, respectively.

(ii) Synthesis of 2-n-propyloxy-6-(2-tert-butoxycarbonylvinyl)naphthalene 2-n-propyloxy-6-(2-tert-butoxycarbonylvinyl)naphthalene was obtained in the same manner as in the Example 44, except for using 2-(n-propyloxy)-6-bromonaphthalene synthesized in the step (i) and hexane as the recrystallization solvent instead of 4-(tert-butoxycarbonyloxy)-4'-bromobiphenyl and methanol, respectively.

$^1$H-NMR(CDCl$_3$) ppm: 1.09(t, 3H, CH$_3$), 1.55(s, 9H, tert-Bu), 1.78-1.99(m, 2H, CH$_2$), 4.05(t, 2H, OCH$_2$), 6.43(d, 1H, CH=CH), 7.09-7.20(m, 2H, C$_{10}$H$_6$), 7.57-7.88(m, 5H, C$_6$H$_4$ and CH=CH).

Example 103

Synthesis of 9,9-bis[4-(2-tert-butoxycarbonylvinyl)phenyl]fluorene (Compound 103)

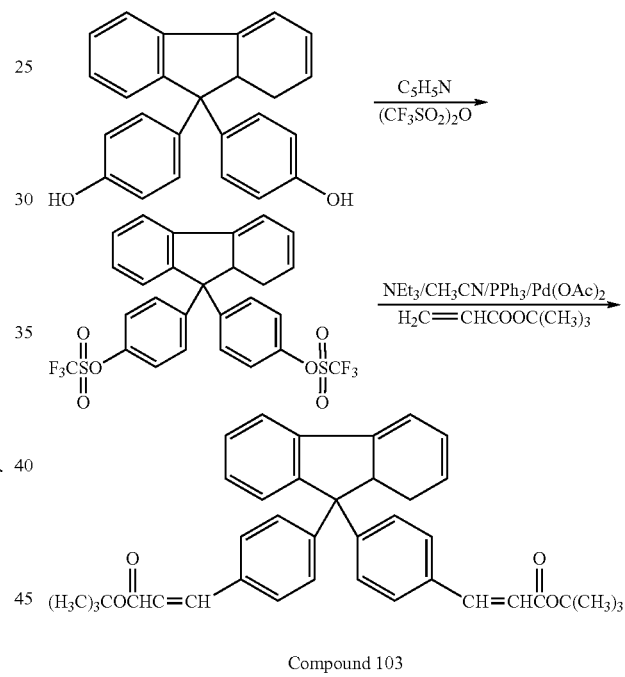

Compound 103

(i) Synthesis of 9,9-bis[4-(trifluoromethylsulfonyloxy)phenyl]fluorene

The reaction was conducted in the same manner as in the step (i) of the Example 94, except for using for 9,9-bis(4-hydroxyphenyl)fluorene instead of 2,2-bis(4-hydroxyphenyl)hexafluoropropane, and the resultant was recrystallized from a mixed solvent of hexane/ethyl acetate to give 9,9-bis[4-(trifluoromethylsulfonyloxy)phenyl]fluorene.

(ii) Synthesis of 9,9-bis[4-(2-tert-butoxycarbonylvinyl)phenyl]fluorene

The reaction was conducted in the same manner as in the Example 44, except for using 9,9-bis[4-(trifluoromethylsulfonyloxy)phenyl]fluorene synthesized in the step (i) and tri-o-tolylphosphine instead of 4-(tert-butoxycarbonyloxy)-4'-bromobiphenyl and triphenylphosphine, respectively, and the resultant was purified by silica gel column chromatography (eluent: toluene) to provide 9,9-bis[4-(2-tert-butoxycarbonylvinyl)phenyl]fluorene.

¹H-NMR(CDCl₃) ppm: 1.53(s, 18H, tert-Bu), 6.29(d, 2H, CH=CH), 7.08-7.45(m, 14H, C₆H₄ and C₁₃H₈), 7.51(d, 2H, CH=CH), 7.78(d, 2H, C₁₃H₈).

Example 104

Synthesis of 1,4-di(tert-butyl)terephthalate (Compound 104)

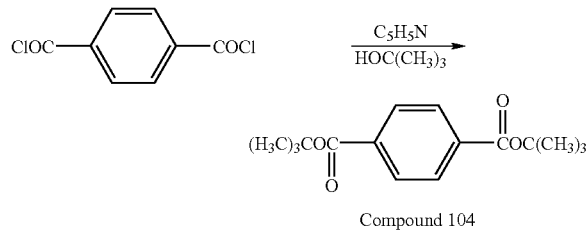

Compound 104

Terephthaloyl dichloride (5.0 g: 24.6 mmol) was dissolved in 50 ml of dehydrated pyridine, and tert-butanol (4.0 g: 54.1 mmol) was added to the mixture. The reaction was carried out at a room temperature for 24 hours. The reaction mixture was poured into an iced water, and the resultant mixture was acidified by adding hydrochloric acid. The resultant precipitate was collected by filtration, washed with water, dried, and recrystallized from methanol to provide 6.1 g (21.9 mmol) of 1,4-di(tert-butyl) terephthalate.

¹H-NMR(CDCl₃) ppm: 1.60(s, 18H, tert-Bu), 8.02(s, 4H, C₆H₄).

Example 105

Synthesis of 1,3,5-tri(tert-butyl)trimesate (Compound 105)

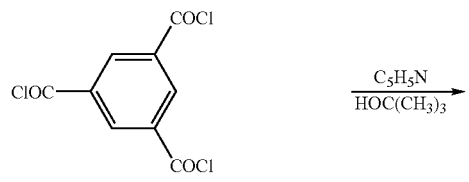

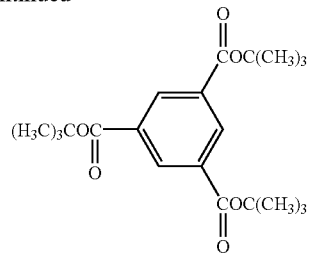

Compound 105

1,3,5-tri(tert-butyl) trimesate was obtained in the same manner as in Example 104, except for using trimesoyl trichloride in lieu of terephthaloyl dichioride.

¹H-NMR(CDCl₃) ppm: 1.60(s, 27H, tert-Bu), 8.72(s, 3H, C₆H₃).

Example 106

Synthesis of 1-[4-(tert-butoxycarbonyl)phenyl]-2-(4-n-propyloxyphenyl)acetylene (Compound 106)

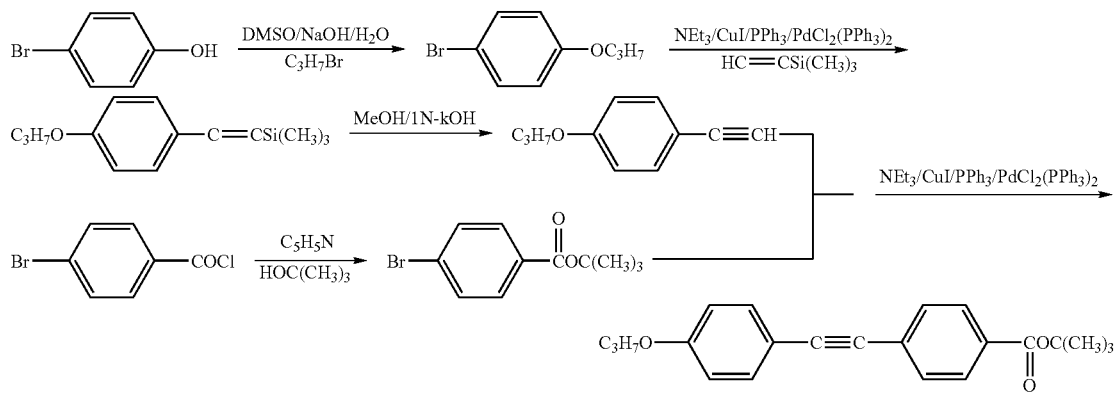

Compound 106

(i) Synthesis of 1-tert-butyl-4-bromobenzoate 1-tert-butyl-4-bromobenzoate was obtained in the same manner as in the Example 104, except for using 4-bromobenzoyl chloride instead of terephthaloyl dichloride.

(ii) Synthesis of 1-[4-(tert-butoxycarbonyl)phenyl]-2-(4-n-propyloxyphenyl)acetylene The reaction was conducted in the same manner as in the step (i) of the Example 31, except for using 1-tert-butyl-4-bromobenzoate synthesized in the step (i) and 4-n-propyloxyphenylacetylene synthesized in the step (iii) of the Example 32 instead of 1-n-propyl-4-bromobenzene and trimethylsilylacetylene, respectively. After completion of the reaction, the reaction mixture was poured into an iced water, and the resultant mixture was acidified by adding hydrochloric acid. The resultant solid was collected by filtration, washed with water, dried, and recrystallized from hexane to give 1-[4-(tert-butoxycarbonyl)phenyl]-2-(4-n-propyloxyphenyl)acetylene.

¹H-NMR(CDCl₃) ppm: 1.06(t, 3H, CH₃), 1.60(s, 9H, tert-Bu), 1.73-1.91(m, 2H, CH₂), 3.95(t, 2H, OCH₂), 6.88(d, 2H, C₆H₄), 7.48(d, 2H, C₆H₄), 7.53(d, 2H, C₆H₄), 7.95(d, 2H, C₆H₄).

Example 107

Synthesis of 1-[4-(tert-butoxycarbonyl)phenyl]-2-(4-n-propylphenyl)acetylene (Compound 107)

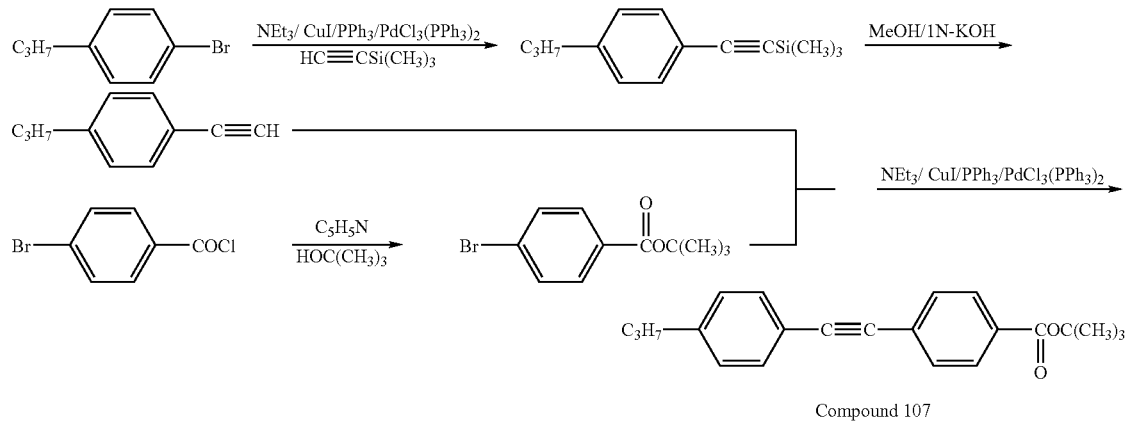

Compound 107

The reaction was conducted in the same manner as in the step (i) of the Example 31, except for using 1-tert-butyl-4-bromobenzoate synthesized in the step (i) of the Example 106 and 4-n-propylphenylacetylene synthesized in the step (ii) of the Example 31 instead of 1-n-propyl-4-bromobenzene and trimethylsilylacetylene, respectively. After completion of the reaction, the reaction mixture was poured into an iced water, and the resultant mixture was acidified by adding hydrochloric acid. The resultant solid was collected by filtration, washed with water, dried, and recrystallized from hexane to give 1-[4-(tert-butoxycarbonyl)phenyl]-2-(4-n-propylphenyl)acetylene.

$^1$H-NMR(CDCl$_3$) ppm: 0.95(t, 3H, CH$_3$), 1.59(s, 9H, tert-Bu), 1.59-1.75(m, 2H, CH$_2$), 2.60(t, 2H, CH$_2$), 7.18(d, 2H, C$_6$H$_4$), 7.46(d, 2H, C$_6$H$_4$), 7.55(d, 2H, C$_6$H$_4$), 7.96(d, 2H, C$_6$H$_4$).

Example 108

Synthesis of 4'-(n-propyloxy)-4-(tert-butoxycarbonyl)biphenyl (Compound 108)

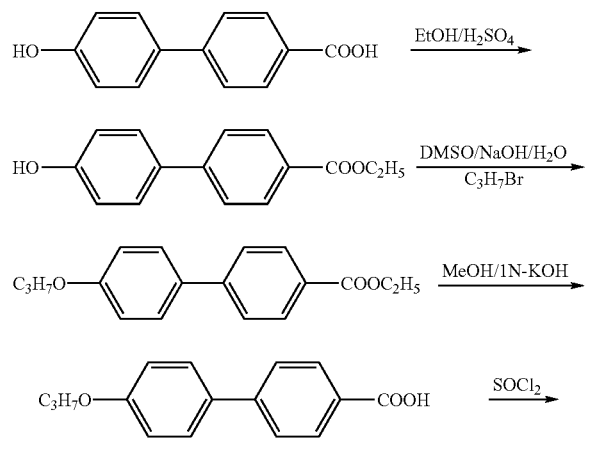

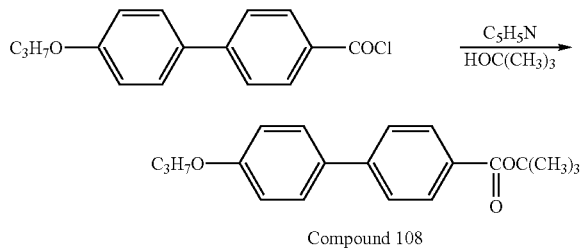

Compound 108

(i) Synthesis of ethyl 4-(4-hydroxyphenyl)benzoate

The reaction was conducted in the same manner as in the step (i) of the Example 33, except for using 4-(4-hydroxyphenyl)benzoic acid and ethanol in lieu of 4-n-propylbenzoic acid and methanol, respectively, and the resultant was recrystallized from toluene to give ethyl 4-(4-hydroxyphenyl)benzoate.

(ii) Synthesis of 4-(4-n-propyloxyphenyl)benzoic acid 4-(4-n-propyloxyphenyl) benzoic acid was obtained in the same manner as in the step (i) of the Example 24, except for using ethyl 4-(4-hydroxyphenyl)benzoate synthesized in the step (i) instead of methyl 4-hydroxybenzoate.

(iii) Synthesis of 4'-(n-propyloxy)-4-(tert-butoxycarbonyl)biphenyl

Thionyl chloride (10 ml) was added to 5.0 g (19.5 mmol) of 4-(4-n-propyloxyphenyl)benzoic acid synthesized in the step (ii), and the mixture was refluxed overnight. After an excess amount of thionyl chloride was removed from the resultant mixture, 4'-(n-propyloxy)-4-(tert-butoxycarbonyl)biphenyl was obtained in the same manner as in the Example 104.

1H-NMR(CDCl$_3$) ppm: 1.07(t, 3H, CH$_3$), 1.61(s, 9H, tert-Bu), 1.78-1.94(m, 2H, CH$_2$), 3.99(t, 2H, OCH$_2$), 6.99(d, 2H, C$_6$H$_4$), 7.55(d, 2H, C$_6$H$_4$), 7.60(d, 2H, C$_6$H$_4$), 8.02(d, 2H, C$_6$H$_4$).

Example 109

Synthesis of 1-tert-butyl 4-(trans-4-propylcyclohexyl)benzoate (Compound 109)

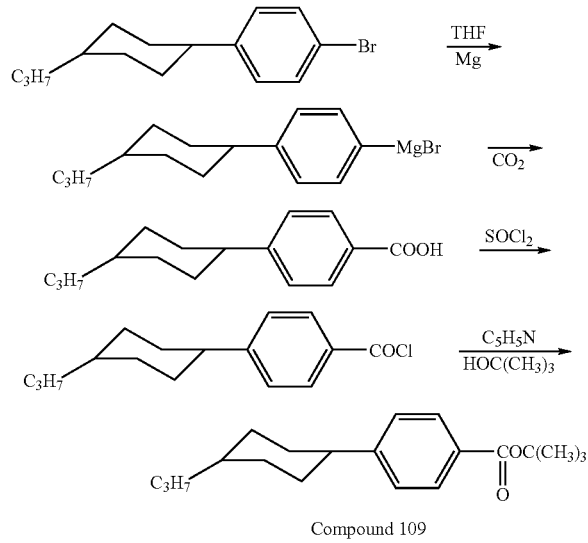

Compound 109

(i) Synthesis of p-(trans-4-propylcyclohexyl)benzoic acid

A Grignard reagent was prepared from a solution of 50 ml of dried tetrahydrofuran in which 0.88 g (36.7 mmol) of magnesium and 10.0 g (35.6 mmol) of 1-(trans-4-n-propyl-cyclohexyl)-4-bromobenzene were dissolved, and the Grignard reagent was put into dry ice. After vaporizing the dry ice, hydrochloric acid was added to the resultant to give a precipitate, and the precipitate was filtered, washed with water, dried, and recrystallized from toluene to give 7.5 g (30.5 mmol) of p-(trans-4-propylcyclohexyl)benzoic acid.

(ii) Synthesis of 1-tert-butyl 4-(trans-4-propylcyclohexyl) benzoate

The reaction was conducted in the same manner as in the step (iii) of the Example 108, except for using p-(trans-4-propylcyclohexyl)benzoic acid synthesized in the step (i) instead of 4-(4-n-propyloxyphenyl)benzoic acid, and the resultant was recrystallized from ethanol to give 4-(trans-4-propylcyclohexyl)-1-tert-butylbenzoate.

$^1$H-NMR(CDCl$_3$) ppm: 0.90(t, 3H, CH$_3$), 0.95-1.55(m, 9H, C$_2$H$_4$ and C$_6$H$_{10}$), 1.55(s, 9H, tert-Bu), 1.84-1.99(m, 4H, C$_6$H$_{10}$), 2.49-2.67(m, 1H, C$_6$H$_{10}$), 7.35(d, 2H, C$_6$H$_4$), 8.06(d, 2H, C$_6$H$_4$).

Example 110

Synthesis of 1-tert-butyl 4-(4-n-propylphenyl)benzoate (Compound 110)

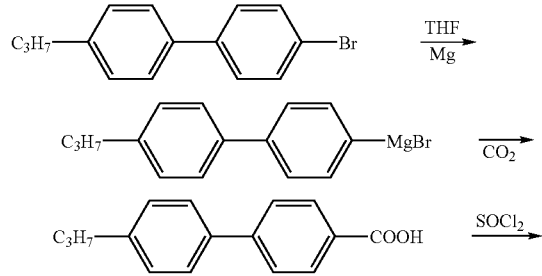

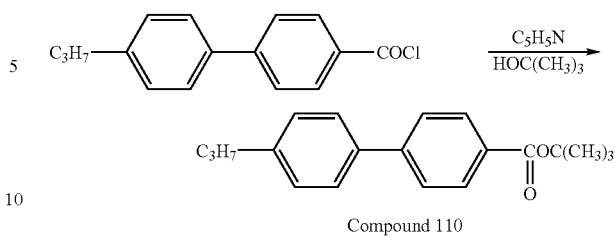

Compound 110

(i) Synthesis of 4-(4-n-propylphenyl)benzoic acid 4-(4-n-propylphenyl)benzoic acid was obtained in the same manner as in the step (i) of the Example 109, except for using 4-n-propyl-4'-bromobiphenyl instead of 1-(trans-4-n-propylcyclohexyl)-4-bromobenzene.

(ii) Synthesis of 1-tert-butyl 4-(4-n-propylphenyl)benzoate

The reaction was conducted in the same manner as in the step (iii) of the Example 108, except for using 4-(4-n-propylphenyl)benzoic acid synthesized in the step (i) instead of 4-(4-n-propyloxyphenyl)benzoic acid, and the resultant was recrystallized from ethanol to provide 1-tert-butyl 4-(4-n-propylphenyl)benzoate.

$^1$H-NMR(CDCl$_3$) ppm: 0.98(t, 3H, CH$_3$), 1.60(s, 9H, tert-Bu), 1.60-1.80(m, 2H, CH$_2$), 2.65(t, 2H, CH$_2$), 7.28(d, 2H, C$_6$H$_4$), 7.55(d, 2H, C$_6$H$_4$), 7.63(d, 2H, C$_6$H$_4$), 8.04(d, 2H, C$_6$H$_4$).

Example 111

Synthesis of 9-[4-(tert-butoxycarbonyloxy)phenyl]-9-[4-hydroxyphenyl]fluorene (Compound 111)

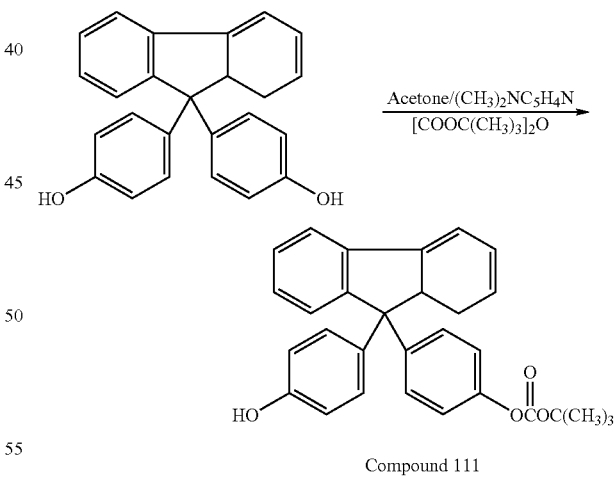

Compound 111

9-[4-(tert-butoxycarbonyloxy)phenyl]-9-[4-hydroxyphenyl]fluorene was obtained in the same manner as in the Example 20, except for using 1/2 mole of di-tert-butyl dicarbonate relative to 1 mole of 9,9-bis(4-hydroxyphenyl)fluorene and being purified with a silica gel column chromatography (eluent: hexane/ethyl acetate=7/3).

$^1$H-NMR(CDCl$_3$) ppm: 1.55(s, 9H, tert-Bu), 6.67(d, 2H, C$_6$H$_4$), 7.00(d, 2H, C$_6$H$_4$), 7.06(d, 2H, C$_6$H$_4$), 7.19(d, 2H, C$_6$H$_4$), 7.22-7.39(m, 6H, C$_{13}$H$_8$), 7.75(d, 2H, C$_{13}$H$_8$).

Examples 112 to 185

Evaluation of the Photosensitive Composition Containing the Photoactive Substance Obtained in the Examples 1 to 111

(1) Preparation of a Photosensitive Resin

To 0.5 part by weight of a polyvinylphenol resin having an average molecular weight of 9,000 in which 35 mol % of hydroxyl groups were protected by 1-ethoxyethoxy group, was added 0.5 part by weight of a polyvinylphenol resin having an average molecular weight of 8,500 in which 37 mol % of hydroxyl groups were substituted with t-BOC (tert-butoxycarbonyloxy) group, and was further added 0.02 part by weight of the photo acid generator (photoactive acid generator) represented by the following formula (A). To the resultant mixture was added 6 parts by weight of propylene glycol monomethyl ether acetate as a solvent and mixed to prepare a positive photoresist.

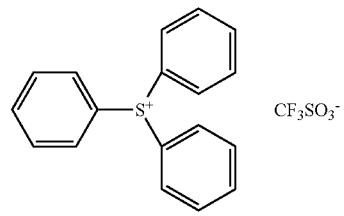

(A)

(2) Preparation of a Photosensitive Resin Composition

The photoactive compounds obtained in the Examples were added to the photosensitive resin solution obtained in the step (1) in the ratio shown in Table 1, and the resultant mixture was filtered by using a fluorine-containing resin (polytetrafluoroethylene) (0.2 μm) to give a photosensitive resin composition. Incidentally, the ratios shown in Table 1 denote those corresponding to solid content excluding the solvent of the photosensitive resin composition.

(3) Evaluation of the Properties (Sensitivity, γ Value, Resolution)

After treating a washed silicon wafer with hexamethyldisilazane, the photosensitive resin composition obtained in the step (2) was coated on the wafer by means of a spin coater in order that a resist layer of 0.4 μm thick after drying was formed, and the wafer was heated on a hot plate at 100° C. for 1 minute. Thereafter, exposure was conducted through a test mask having a line-and-space pattern with different line widths, using a reduced projection exposing machine (manufactured by Canon Inc., FPA-3000EX5, NA=0.63) having an exposing wavelength of 248 nm (KrF excimer laser) with changing the exposure amount in steps. After heating, the wafer at 100° C. on a hot plate for 1 minute, the wafer was paddle-developed with an aqueous solution of tetramethylammonium hydroxide (2.38% by weight) for 1 minute to give a positive pattern.

The positive pattern was evaluated for its properties according to the following manner.

(i) Sensitivity: expressed in terms of such an amount of exposed dose to print just as the same size of the mask with a line width of 0.25 μm that the ratio of the width of the line relative to that of the space becomes 1:1 (the smaller the value is, the higher the sensitivity is).

(ii) γ (gamma) value: changes in the standardized thickness of a residual resist layer (a thickness of the layer in which the initial thickness of the layer was regarded as 1) in the exposed area relative to logarithm of an amount of light exposure, what is called a sensitivity curve, were plotted. A tangential line was drawn at the point of the thickness of a residual resist layer being 0, and the slope of the tangential line was regarded as γ value (the higher the value is, the higher and better the contrast is).

(iii) Resolution: expressed in terms of a minimum width of the lines distinctly formed by exposing at the amount of exposed dose to print just as the same size of the mask with a line width of 0.25 tm that the ratio of the width of the line relative to that of the space becomes 1:1 (the smaller the value is, the higher and better the resolution is).

The results are shown in Tables 1 and 2. Incidentally, as a Comparative Example, sensitivity and resolution of the photosensitive resin composition containing no photoactive compound were also shown in Table 1.

TABLE 1

| | Composition | | | Properties | |
| --- | --- | --- | --- | --- | --- |
| | Photosensitive resin (parts by weight) | Photoactive compound Species | Parts by weight | Sensitivity (mJ/cm$^2$) | Resolution (μm) |
| Comparative Example 1 | 1 | — | — | 53 | 0.24 |
| Example 112 | 1 | Example 1 | 0.11 | 25 | 0.16 |
| Example 113 | 1 | Example 1 | 0.25 | 23 | 0.17 |
| Example 114 | 1 | Example 2 | 0.11 | 33 | 0.16 |
| Example 115 | 1 | Example 2 | 0.25 | 23 | 0.17 |
| Example 116 | 1 | Example 14 | 0.25 | 22 | 0.16 |
| Example 117 | 1 | Example 14 | 0.43 | 22 | 0.16 |
| Example 118 | 1 | Example 17 | 0.05 | 44 | 0.18 |
| Example 119 | 1 | Example 17 | 0.11 | 42 | 0.19 |
| Example 120 | 1 | Example 19 | 0.11 | 25 | 0.17 |
| Example 121 | 1 | Example 19 | 0.18 | 23 | 0.16 |
| Example 122 | 1 | Example 20 | 0.05 | 30 | 0.17 |
| Example 123 | 1 | Example 20 | 0.11 | 33 | 0.17 |
| Example 124 | 1 | Example 22 | 0.11 | 37 | 0.18 |
| Example 125 | 1 | Example 22 | 0.25 | 34 | 0.19 |
| Example 126 | 1 | Example 24 | 0.11 | 42 | 0.19 |
| Example 127 | 1 | Example 24 | 0.25 | 43 | 0.20 |
| Example 128 | 1 | Example 25 | 0.11 | 38 | 0.16 |
| Example 129 | 1 | Example 25 | 0.25 | 41 | 0.17 |
| Example 130 | 1 | Example 26 | 0.11 | 35 | 0.16 |
| Example 131 | 1 | Example 26 | 0.25 | 37 | 0.17 |
| Example 132 | 1 | Example 27 | 0.11 | 35 | 0.16 |
| Example 133 | 1 | Example 27 | 0.25 | 38 | 0.17 |
| Example 134 | 1 | Example 28 | 0.11 | 39 | 0.16 |
| Example 135 | 1 | Example 28 | 0.25 | 41 | 0.17 |
| Example 136 | 1 | Example 29 | 0.11 | 25 | 0.18 |
| Example 137 | 1 | Example 29 | 0.25 | 23 | 0.18 |
| Example 138 | 1 | Example 29 | 0.43 | 21 | 0.18 |
| Example 139 | 1 | Example 30 | 0.11 | 27 | 0.20 |
| Example 140 | 1 | Example 30 | 0.25 | 24 | 0.20 |
| Example 141 | 1 | Example 30 | 0.43 | 23 | 0.19 |
| Example 142 | 1 | Example 31 | 0.11 | 24 | 0.16 |
| Example 143 | 1 | Example 31 | 0.25 | 22 | 0.16 |
| Example 144 | 1 | Example 31 | 0.43 | 20 | 0.15 |
| Example 145 | 1 | Example 32 | 0.11 | 25 | 0.16 |
| Example 146 | 1 | Example 32 | 0.25 | 20 | 0.16 |
| Example 147 | 1 | Example 32 | 0.43 | 20 | 0.16 |
| Example 148 | 1 | Example 33 | 0.11 | 28 | 0.16 |
| Example 149 | 1 | Example 33 | 0.25 | 25 | 0.15 |
| Example 150 | 1 | Example 33 | 0.43 | 22 | 0.16 |

TABLE 2

| | Composition | | Properties | |
|---|---|---|---|---|
| | Photosensitive resin (parts by weight) | Photoactive compound | | Resolution (μm) |
| | | Species | Parts by weight | Sensitivity (mJ/cm$^2$) | |
| Example 151 | 1 | Example 34 | 0.11 | 27 | 0.18 |
| Example 152 | 1 | Example 48 | 0.11 | 25 | 0.17 |
| Example 153 | 1 | Example 48 | 0.25 | 27 | 0.17 |
| Example 154 | 1 | Example 48 | 0.43 | 29 | 0.16 |
| Example 155 | 1 | Example 49 | 0.25 | 18 | 0.20 |
| Example 156 | 1 | Example 50 | 0.11 | 24 | 0.17 |
| Example 157 | 1 | Example 50 | 0.25 | 26 | 0.16 |
| Example 158 | 1 | Example 50 | 0.43 | 28 | 0.16 |
| Example 159 | 1 | Example 52 | 0.11 | 25 | 0.17 |
| Example 160 | 1 | Example 52 | 0.25 | 27 | 0.17 |
| Example 161 | 1 | Example 52 | 0.43 | 27 | 0.17 |
| Example 162 | 1 | Example 53 | 0.11 | 32 | 0.16 |
| Example 163 | 1 | Example 53 | 0.25 | 35 | 0.17 |
| Example 164 | 1 | Example 54 | 0.11 | 22 | 0.19 |
| Example 165 | 1 | Example 54 | 0.25 | 23 | 0.20 |
| Example 166 | 1 | Example 54 | 0.43 | 24 | 0.20 |
| Example 167 | 1 | Example 55 | 0.11 | 24 | 0.20 |
| Example 168 | 1 | Example 55 | 0.25 | 23 | 0.19 |
| Example 169 | 1 | Example 55 | 0.43 | 22 | 0.18 |
| Example 170 | 1 | Example 56 | 0.11 | 27 | 0.18 |
| Example 171 | 1 | Example 56 | 0.25 | 25 | 0.19 |
| Example 172 | 1 | Example 57 | 0.11 | 25 | 0.20 |
| Example 173 | 1 | Example 57 | 0.25 | 27 | 0.19 |
| Example 174 | 1 | Example 57 | 0.43 | 29 | 0.18 |
| Example 175 | 1 | Example 58 | 0.11 | 22 | 0.17 |
| Example 176 | 1 | Example 58 | 0.25 | 20 | 0.17 |
| Example 177 | 1 | Example 58 | 0.43 | 19 | 0.18 |
| Example 178 | 1 | Example 59 | 0.11 | 24 | 0.18 |
| Example 179 | 1 | Example 59 | 0.25 | 26 | 0.17 |
| Example 180 | 1 | Example 59 | 0.43 | 29 | 0.16 |
| Example 181 | 1 | Example 64 | 0.11 | 23 | 0.17 |
| Example 182 | 1 | Example 64 | 0.25 | 25 | 0.16 |
| Example 183 | 1 | Example 64 | 0.43 | 28 | 0.16 |
| Example 184 | 1 | Example 70 | 0.05 | 21 | 0.17 |
| Example 185 | 1 | Example 70 | 0.11 | 20 | 0.16 |

The invention claimed is:

1. A photosensitive resin composition, comprising:
a base resin;
a photosensitizer; and
a photoactive compound usable in combination with the photosensitizer, said compound being represented by the following formula (1):

$$A-[(J)_m-(X-Pro)]_n \quad (1)$$

wherein A represents a hydrophobic unit comprising at least one hydrophobic group selected from the group consisting of a hydrocarbon group and a heterocyclic group, J represents a connecting group, r represents 0 or an integer of not less than 1, X-Pro represents a hydrophilic group protected by a protective group Pro which is removable by light exposure, m represents 0 or 1, and n represents an integer of not less than 1, wherein, the compound is represented by the following formula (4b), (4b)

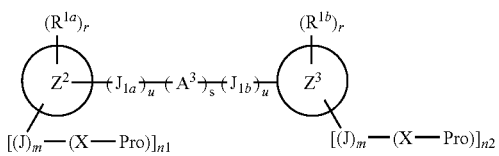

wherein,
$Z^2$ and $Z^3$ are the same or different, each representing a hydrocarbon ring or a heterocycle;
$A^3$ represents a connecting group selected from the group consisting of a direct bond, an alkylene group, an alkenylene group, an alkynylene group, a cycloalkylene group, an arylene group, an oxyalkylene group, an alkyleneoxy group, an ether group, a thioether group, a carbonyl group, a carbonyloxy group, an oxycarbonyl group, an amide group, a urethane group, a urea group and a sulfonyl group;
s and u are the same or different, each denoting 0 or 1;
$J_{1a}$ and $J_{1b}$ are the same or different, each representing a connecting group different from $A^3$;
$R^{1a}$ and $R^{1b}$ are the same or different, each representing a halogen atom, an alkyl group, an alkoxy group, an alkoxycarbonyl group, a cycloalkyl group, an aryl group, an aralkyl group or a silicon-containing group;
each of the factors, n1 and n2, independently represents 0 or an integer of not less than 1, and n1+n2≧1; and
J, r, m, and X-Pro have the same meanings defined above, the protective group Pro is:
(i) a protective group for a hydroxyl group, selected from the group consisting of an alkoxyalkyl group, an acyl group, an alkoxycarbonyl group, a crosslinked cyclic alicyclic group, and an alkylsilyl group; or
(ii) a protective group for a carboxyl group, selected from the group consisting of an alkyl group, a crosslinked cyclic alicyclic hydrocarbon group, a lactone ring group, and a carbamoyl or N-substituted carbamoyl group,
and further wherein at least one of the following conditions (i)-(v) is present:
(i) $A^3$ is, an alkynylene group, a condensed hydrocarbon ring group, an oxyalkylene group, or an alkyleneoxy group and s=1;
(ii) at least one of $R^{1a}$ and $R^{1b}$ is a silicon-containing group, r is 0 or 1 to 6 for the ring $Z^2$, and r is 1 to 6 for the ring $Z^3$;
(iii) $A^3$ is a carbonyloxy group or an oxycarbonyl group, $R^{1a}$ and $R^{1b}$ are each an alkoxy group, s=1, r is 0 or 1 to 6 for the ring $Z^2$, r is 1 to 6 for the ring $Z^3$, and n1+n2=1;
(iv) $A^3$ is a carbonyloxy group or an oxycarbonyl group, J is an alkenylene group or an alkynylene group, s=1, and m is 1; or
(v) $A^3$ is a carbonyloxy group, an oxycarbonyl group, or a sulfonyl group, the protective group Pro is an alkoxyalkyl group, and s=1.

2. A photosensitive resin composition according to claim 1, wherein the protective group Pro is removable by light exposure in association with the photosensitizer.

3. A photosensitive resin composition according to claim 1, wherein in the formula (4b), in the case where the connecting group $A^3$ is direct bonding, an alkylene group, an alkynylene group, an oxyalkylene group, an alkyleneoxy group, an ether group, a thioether group, a carbonyl group, a carbonyloxy group, an oxycarbonyl group, an amide group, a urethane group, a urea group or a sulfonyl group, u=0, or in the case where the connecting group $A^3$ is a cycloalkylene group or an arylene group, u=1.

4. A photosensitive resin composition according to claim 1, wherein in the formula (4b), the hydrophobic unit represented by $Z^2-(J_{1a})_u-(A^3)_s-(J_{1b})_u-Z^3$ is a 9,9-bis(hydroxyphenyl)fluorene.

5. A photosensitive resin composition according to claim 1, which is developable with water or an alkaline developer.

6. A photosensitive resin composition according to claim 1, which is a positive photosensitive resin composition.

7. A photosensitive resin composition according to claim 1, wherein the base resin comprises a resin which forms a hydrophilic group by an action of an acid, and the photosensitizer comprises a photo acid generator.

8. A photosensitive resin composition according to claim 1, wherein the base resin comprises a homo- or copolymer of a monomer having a hydrophilic group; and the hydrophilic group is selected from the group consisting of a hydroxyl group and a carboxyl group, and is protectable by a protective group removable by an action of an acid.

9. A photosensitive resin composition according to claim 1, wherein the weight ratio of the photoactive compound relative to the photosensitizer is 0.01/1 to 100/1.

10. A photosensitive resin composition according to claim 1, wherein the amount of the photosensitizer is 0.1 to 50 parts by weight and the amount of the photoactive compound is 1 to 1000 parts by weight, relative to 100 parts by weight of the base resin.

11. A process for forming a pattern, which comprises applying or coating a photosensitive resin composition recited in claim 1 onto a substrate, exposing the coating layer to light, heat-treating the light-exposed layer, and developing the heat-treated layer to form a pattern.

12. A photosensitive resin composition according to claim 1, wherein the protective group Pro is a hydrophobic protective group, and the photoactive compound forms a hydroxyl group or a carboxyl group by deprotection of the hydrophobic protective group.

13. A photosensitive resin composition according to claim 1, wherein in the formula (4b), in the case where the connecting group $A^3$ is a cycloalkylene group or an arylene group, each of the connecting groups, $J_{1a}$ and $J_{1b}$, is direct bonding or an alkylene group.

14. A photosensitive resin composition according to claim 1, wherein in the formula (4b), in the case where the connecting group $A^3$ is a cycloalkylene group or an arylene group, each of the connecting groups, $J_{1a}$ and $J_{1b}$, is an alkylene group which may have a substituent selected from the group consisting of a halogen atom, an alkyl group, a cycloalkyl group, and an aryl group.

15. A photosensitive resin composition according to claim 1, wherein in the formula (4b), the hydrophobic unit represented by $Z^2$-$(J_{1a})_u$-$(A^3)_s$-$(J_{1b})_u$-$Z^3$ is a hydrophobic unit corresponding to the compound selected from the group consisting of (a) a biphenol; (b) a bis(hydroxyaryl)$C_{1-10}$alkane; (c) a bis(hydroxyaryl)cycloalkane; (d) a bisphenol in which $A^3$ is a carbonyl group, an oxygen atom, an ester group, an alkyleneoxy group, an oxyalkylene group, an amide group or a sulfonyl group; (e) a bisphenol in which $A^3$ is a benzene ring, and $J_{1a}$ and $J_{1b}$ are an alkylene group; and (h) a bisphenol having a fluorene-skeleton; and the summation of n1 and n2 is to 10.

16. A photosensitive resin composition according to claim 1, wherein in the formula (4b), s=1, and $A^3$ is an alkynylene group, an alkyleneoxy group, an oxyalkylene group or a cycloalkylene group.

17. A photosensitive resin composition according to claim 1, wherein in the formula (4b), s=1, u=0, and $A^3$ is a $C_{2-4}$alkynylene group, a $C_{1-6}$alkyleneoxy group, an oxy$C_{1-6}$alkylene group, or a $C_{4-8}$cycloalkylene group.

18. A photosensitive resin composition according to claim 1, wherein in the formula (4b), s=1, u=0, and $A^3$ is an oxycarbonyl group, a carbonyloxy group or a sulfonyl group, and the protective group Pro is an alkoxyalkyl group.

19. A photosensitive resin composition according to claim 1, wherein in the formula (4b), $Z^2$ is a cycloalkane ring, and $Z^3$ is an aromatic hydrocarbon ring.

20. A photosensitive resin composition according to claim 1, wherein in the formula (4b), $Z^2$ is a $C_{4-8}$cycloalkane ring, $Z^3$ is a $C_{6-10}$arene ring, s is 0 or 1, u=0, and $A^3$ is an oxycarbonyl group or a carbonyloxy group.

21. A photosensitive resin composition according to claim 1, wherein in the formula (4b), r is 0 or 1 to 6 for the ring $Z^2$, or r is 1 to 6 for the ring $Z^3$, $R^{1a}$ is a silicon-containing group, and $R^{1b}$ is a silicon-containing group.

22. A photosensitive resin composition according to claim 1, wherein in the formula (4b), r is 0 or 1 to 4 for the ring $Z^2$, or r is 1 to 4 for the ring $Z^3$ and $R^{1a}$ and $R^{1b}$ are the same or different, each representing a $C_{1-18}$alkylsilyl$C_{2-4}$alkenyl group or a $C_{1-18}$alkylsilyl$C_{2-4}$alkynyl group.

* * * * *

UNITED STATES PATENT AND TRADEMARK OFFICE
CERTIFICATE OF CORRECTION

PATENT NO. : 7,534,547 B2
APPLICATION NO. : 10/296831
DATED : May 19, 2009
INVENTOR(S) : Hanabata et al.

It is certified that error appears in the above-identified patent and that said Letters Patent is hereby corrected as shown below:

Column 110, claim 1, is amended to read:

1. A photosensitive resin composition, comprising:

a base resin;

a photosensitizer; and a photoactive compound usable in combination with the photosensitizer, said compound being represented by the following formula (1):

$$A\text{-}[(J)_m\text{-}(X\text{-}Pro)]_n \qquad (1)$$

wherein A represents a hydrophobic unit comprising at least one hydrophobic group selected from the group consisting of a hydrocarbon group and a heterocyclic group, J represents a connecting group, r represents 0 or an integer of not less than 1, X-Pro represents a hydrophilic group protected by a protective group Pro which is removable by light exposure, m represents 0 or 1, and n represents an integer of not less than 1, wherein, the compound is represented by the following formula (4b),

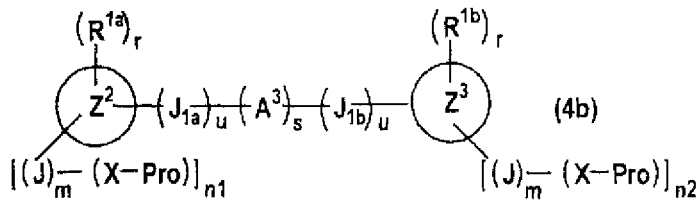

wherein, $Z^2$ and $Z^3$ are the same or different, each representing a hydrocarbon ring or a heterocycle;

Signed and Sealed this
Twenty-eighth Day of December, 2010

David J. Kappos
*Director of the United States Patent and Trademark Office*

$A^3$ represents a connecting group selected from the group consisting of a direct bond, an alkylene group, an alkenylene group, an alkynylene group, a cycloalkylene group, an arylene group, an oxyalkylene group, an alkyleneoxy group, an ether group, a thioether group, a carbonyl group, a carbonyloxy group, an oxycarbonyl group, an amide group, a urethane group, a urea group and a sulfonyl group;

s and u are the same or different, each denoting 0 or 1;

$J_{1a}$ and $J_{1b}$ are the same or different, each representing a connecting group different from $A^3$;

$R^{1a}$ and $R^{1b}$ are the same or different, each representing a halogen atom, an alkyl group, an alkoxy group, an alkoxycarbonyl group, a cycloalkyl group, an aryl group, an aralkyl group or a silicon-containing group;

each of the factors, n1 and n2, independently represents 0 or an integer of not less than 1, and n1+n2≥1; and J, r, m, and X-Pro have the same meanings defined above, the protective group Pro is:

(i) a protective group for a hydroxyl group, selected from the group consisting of an alkoxyalkyl group, an acyl group, an alkoxycarbonyl group, a crosslinked cyclic alicyclic group, and an alkylsilyl group; or (ii) a protective group for a carboxyl group, selected from the group consisting of an alkyl group, a crosslinked cyclic alicyclic hydrocarbon group, a lactone ring group, and a carbamoyl or N-substituted carbamoyl group, and further wherein at least one of the following conditions (i)-(v) is present:

(i)  $A^3$ is[[,]] an alkynylene group, a condensed hydrocarbon ring group, an oxyalkylene group, or an alkyleneoxy group and s=1;

(ii)  at least one of $R^{1a}$ and $R^{1b}$ is a silicon-containing group, r is 0 or 1 to 6 for the ring $Z^2$, and r is 1 to 6 for the ring $Z^3$;

(iii)  $A^3$ is a carbonyloxy group or an oxycarbonyl group, $R^{1a}$ and $R^{1b}$ are each an alkoxy group, s=1, r is 0 or 1 to 6 for the ring $Z^2$, r is 1 to 6 for the ring $Z^3$, and n1+n2=1;

(iv)  $A^3$ is a carbonyloxy group or an oxycarbonyl group, J is an alkenylene group or an alkynylene group, s=1, and m is 1; or (v)  $A^3$ is a carbonyloxy group, an oxycarbonyl group, or a sulfonyl group, the protective group Pro is an alkoxyalkyl group, and s=1.

Column 112, claim 15, is amended to read:

15. A photosensitive resin composition according to claim 1, wherein in the formula (4b), the hydrophobic unit represented by $Z^2\text{-}(J_{1a})_u\text{-}(A^3)_s\text{-}(J_{1b})_u\text{-}Z^3$ is a hydrophobic unit corresponding to the compound selected from the group consisting of (a) a biphenol; (b) a bis(hydroxyaryl)$C_{1\text{-}10}$alkane; (c) a bis(hydroxyaryl)cycloalkane; (d) a bisphenol in which $A^3$ is a carbonyl group, an oxygen atom, an ester group, an alkyleneoxy group, an oxyalkylene group, an amide group or a sulfonyl group; (e) a bisphenol in which $A^3$ is a benzene ring, and $J_{1a}$ and $J_{1b}$ are an alkylene group; and (h) a bisphenol having a fluorene-skeleton; and the summation of n1 and n2 is 1 to 10.

Column 112, claim 17, is amended to read:

17. A photosensitive resin composition according to claim 23, wherein in the formula (4b), s=1, u=0, and $A^3$ is a $C_{2\text{-}4}$alkynylene group, a $C_{1\text{-}6}$alkyleneoxy group, an oxy$C_{1\text{-}6}$alkylene group, or a $C_{4\text{-}8}$cycloalkylene group.